US010314298B2

(12) United States Patent
Murphy

(10) Patent No.: US 10,314,298 B2
(45) Date of Patent: *Jun. 11, 2019

(54) HUMANIZED IL-7 RODENTS

(71) Applicant: Regeneron Pharmaceuticals, Inc., Tarrytown, NY (US)

(72) Inventor: Andrew J. Murphy, Croton-on-Hudson, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/960,642

(22) Filed: Apr. 24, 2018

(65) Prior Publication Data

US 2018/0360007 A1 Dec. 20, 2018

Related U.S. Application Data

(63) Continuation of application No. 15/649,797, filed on Jul. 14, 2017, now Pat. No. 9,974,291, which is a continuation of application No. 15/357,021, filed on Nov. 21, 2016, now Pat. No. 9,737,059, which is a continuation of application No. 14/937,270, filed on Nov. 10, 2015, now abandoned, which is a continuation of application No. 14/551,538, filed on Nov. 24, 2014, now Pat. No. 9,232,776, which is a continuation of application No. 13/795,765, filed on Mar. 12, 2013, now Pat. No. 8,962,913.

(60) Provisional application No. 61/740,074, filed on Dec. 20, 2012, provisional application No. 61/660,976, filed on Jun. 18, 2012.

(51) Int. Cl.
*A01K 67/027* (2006.01)
*A01K 67/02* (2006.01)
*C07K 14/54* (2006.01)

(52) U.S. Cl.
CPC ...... *A01K 67/0278* (2013.01); *C07K 14/5418* (2013.01); *A01K 2207/15* (2013.01); *A01K 2217/052* (2013.01); *A01K 2217/07* (2013.01); *A01K 2217/072* (2013.01); *A01K 2227/105* (2013.01); *A01K 2267/01* (2013.01); *A01K 2267/03* (2013.01); *A01K 2267/0331* (2013.01); *A01K 2267/0387* (2013.01); *A01K 2267/0393* (2013.01)

(58) Field of Classification Search
CPC ............ A01K 67/0278; A01K 2207/15; A01K 2217/052; A01K 2217/07; A01K 2217/072; A01K 2227/105; C07K 2267/0331; C12N 15/8509; C07K 14/5418
USPC .................................................... 800/18, 13
See application file for complete search history.

(56) References Cited

U.S. PATENT DOCUMENTS

| 7,759,541 B2 | 7/2010 | Wolf et al. | |
| 8,962,913 B2 * | 2/2015 | Murphy | ............. A01K 67/0278 800/18 |
| 9,232,776 B2 * | 1/2016 | Murphy | ............. A01K 67/0278 |
| 9,737,059 B2 | 8/2017 | Murphy | |
| 9,974,291 B2 * | 5/2018 | Murphy | ............. A01K 67/0278 |
| 2013/0340104 A1 | 12/2013 | Murphy | |
| 2015/0082469 A1 | 3/2015 | Murphy | |
| 2016/0052986 A1 | 2/2016 | Murphy | |
| 2017/0064932 A1 | 3/2017 | Murphy | |
| 2017/0311581 A1 | 11/2017 | Murphy | |

FOREIGN PATENT DOCUMENTS

| CN | 101302517 A | 11/2008 |
| GB | 2 434 578 A | 1/2007 |
| WO | 01/15521 A1 | 3/2001 |
| WO | 2011/044050 A2 | 4/2011 |
| WO | 2012/112544 A2 | 8/2012 |
| WO | 2013/063556 A1 | 5/2013 |

OTHER PUBLICATIONS

Silva et al. (2011) Cancer Res., vol. 71, 4780-4789.*
Lupton et al. (1990) J. Immunol., vol. 144, 3592-3601.*
Willinger et al. (2011) Trends in Immunology, vol. 32(7), 321-327, and Willinger (2011) PNAS, vol. 108(6), 2390-2395 including Supplement pp. 1-6.*
Willinger (2011) PNAS, vol. 108(6), 2390-2395 including Supplement pp. 1-6.*
GenBank Accession No. NM_000880.3.*
Watanabe M. et al., "Interleukin 7 Transgenic Mice Develop Chronic Colitis with Decreased Interleukin 7 Protein Accumulation in the Colonic Mucosa", J. Exp. Med. 187(3):389-402 (Feb. 2, 1998).
Weissenbach J. et al., "Two Interferon mRNAs in Human Fibroblasts: In Vitro Translation and *Escherichia coli* Cloning Studies", Proc. Natl. Acad. Sci. USA 77(12):7152-7156 (Dec. 1980).
Wheeler M.B. et al., "Transgenic Technology and Applications in Swine", Theriogenology 56:1345-1369 (2001).
Williams I.R. et al., "IL-7 Overexpression in Transgenic Mouse Keratinocytes Causes a Lymphoproliferative Skin Disease Dominated by Intermediate TCR Cells", The Journal of Immunology 159:3044-3056 (1997).
Willinger T. et al., "Human IL-3/GM-CSF Knock-in Mice Support Human Alveolar Macrophage Development and Human Immune Responses in the Lung", PNAS 108(6):2390-2395 (Feb. 8, 2011).

(Continued)

*Primary Examiner* — Anne Marie S Wehbe
(74) *Attorney, Agent, or Firm* — Scully, Scott, Murphy & Presser, P.C.; Elysa Goldberg

(57) ABSTRACT

Genetically modified non-human animals comprising a human or humanized interleukin-7 (IL-7) gene. Cells, embryos, and non-human animals comprising a human or humanized IL-7 gene. Rodents that express human or humanized IL-7 protein. Genetically modified mice that comprise a human or humanized IL-7-encoding gene in their germline, wherein the human or humanized IL-7-encoding gene is under control of endogenous mouse IL-7 regulatory sequences.

6 Claims, 2 Drawing Sheets

Specification includes a Sequence Listing.

(56) References Cited

OTHER PUBLICATIONS

Willinger T. et al., "Improving Human Hemato-Lymphoid System Mice by Cytokine Knock-in Gene Replacement", Trends in Immunology 32(7):321-327 (Jul. 2011).
Zhou Q. et al., "Generation of Fertile Cloned Rats by Regulating Oocyte Activation", Science 302:1179 (Nov. 14, 2003).
Zilberstein A. et al., "Structure and Expression of cDNA and Genes for Human Interferon-Beta-2, a Distinct Species Inducible by Growth-Stimulatory Cytokines", The EMBO Journal 5(10):2529-2537 (1986).
"Rattus Norvegicus Interleukin 7 (II7), mRNA", NCBI Reference Sequence: NM_013110.2 (2 pages) (Aug. 10, 2014).
"Interleukin-7 Precursor [Rattus Norvegicus]", NCBI Reference Sequence: NP_037242.2 (2 pages) (Aug. 10, 2014).
Murphy, D., BAC-based Modifications of the Mouse Genome: The Big and the Backward, a 58-slide PowerPoint® presentation that was used in conjunction with an oral presentation by Dr. Murphy that was given as a lecture at the Wellcome Trust Advanced Course: Genetic Manipulation of ES Cells at the Wellcome Trust, Hinxton, Cambridge, UK on Nov. 3, 2009.
Murphy, D., MFA: the turducken of alleles*, a 76-slide PowerPoint® presentation that was used in conjunction with an oral presentation by Dr. Murphy that was given as a lecture at the Wellcome Trust Course: Genetic Manipulation of ES Cells at the Wellcome Trust, Hinxton, Cambridge, UK, in Nov. 2010.
Dennis, Jr M.B., "Welfare Issues of Genetically Modified Animals", ILAR Journal 43(2):100-109 (2002).
Hofker M.H. et al., "Transgenic Mouse-Methods and Protocols", Methods in Molecular Biology 209:51-58 (2002-2003).
Rybchin V.N., "Fundamentals of Genetic Engineering", Textbook for High Schools, Saint-Petersburg, Publishing House SPbSTU 522:411-413 (2002).
Zhou H. et al., "Developing tTA Transgenic Rats for Inducible and Reversible Gene Expression", International Journal of Biological Sciences 5(2):171-181 (2009).
Russian Office Action dated Oct. 5, 2017 received in Russian Patent Application No. 2014148107, together with an English-language translation.
Alves N.L. et al., "Characterization of the Thymic IL-7 Niche in Vivo", PNAS 106(5):1512-1517 (Feb. 3, 2009).
Aguila H L et al., "Osteoblast-Specific Overexpression of Human Interleukin-7 Rescues the Bone Mass Phenotype of Interleukin-7-Deficient Female Mice", Journal of Bone and Mineral Research 27(5):1030-1042 (May 2012).
Anderson P., "Post-Transcriptional Control of Cytokine Production", Nature Immunology 9(4):353-359 (Apr. 2008).
Carpenter S. et al., "Post-Tanscriptional Regulation of Gene Expression in Innate Immunity", Nature Reviews-Immunology 14:361-376 (Jun. 2014).
Clark J. et al., "A Future for Transgenic Livestock", Nature Reviews-Genetics 4:825-833 (Oct. 2003).
Eisenbarth et al., "Development and Characterization of a Human IL-7 Transgenic Humanized Mouse Model", iwhm2 2nd International Workshop on Humanized Mice, Program & Abstract Book, Sint Olofskapel/Amsterdam/The Netherlands, Abstract #19 (Apr. 3-6, 2009).
Fischer A.G. et al., "Lymphoproliferative Disorders in an IL-7 Transgenic Mouse Line", Leukemia 7(02):S66-S68 (1993).
Foss H-D et al., "Frequent Expression of IL-7 Gene Transcripts in Tumor Cells of Classical Hodgkin's Disease", American Journal of Pathology 146(1):33-39 (Jan. 1995).
Fry T.J., "IL-7 Comes of Age", Blood 107(7):2587-2588 (Apr. 1, 2006).
Fry T.J. et al., "The Many Faces of IL-7: From Lymphopoiesis to Peripheral T Cell Maintenance", The Journal of Immunology 174:6571-6576 (2005).
Fry T.J. et al., "Interleukin-7: from Bench to Clinic", Blood 99(11):3892-3904 (Jun. 1, 2002).
Fry T.J. et al., "A Potential Role for Interleukin-7 in T-Cell Homeostasis", Blood 97(10):2983-2990 (May 15, 2001).

Geiselhart L.A. et al., "IL-7 Administration Alters the CD4:CD8 Ratio, Increases T Cell Numbers, and Increases T Cell Function in the Absence of Activation", The Journal of Immunology 166:3019-3027 (2001).
Goodwin R.G. et al., "Human Interleukin 7: Molecular Cloning and Growth Factor Activity on Human and Murine B-Lineage Cells", Proc. Natl. Acad. Sci. USA 86:302-306 (Jan. 1989).
Guimond M. et al., "Cytokine Signals in T-Cell Homeostasis", J. Immunother 28(4):289-294 (Jul./Aug. 2005).
Jacobs S.R. et al., "IL-7 is Essential for Homeostatic Control of T Cell Metabolism in Vivo", The Journal of Immunology 184:3461-3469 (2010).
Jacob H. et al., "Gene Targeting in the Rat: Advances and Opportunities", Trends in Genetics 26(12):510-518 (Dec. 2010).
Kang J. et al., "Defective Development of $\gamma/\delta$ T Cells in Interleukin 7 Receptor-Deficient Mice is Due to Impaired Expression of T Cell Receptor $\gamma$ Genes", J. Exp. Med. 190(7):973-982 (Oct. 4, 1999).
Kieper W.C. et al., "Overexpression of Interleukin (IL)-7 Leads to IL-15-Independent Generation of Memory Phenotype CD8= T Cells", J. Exp. Med. 195(12):1533-1539 (Jun. 17, 2002).
Kim G.Y. et al., "Seeing is Believing: Illuminating the Source of In Vivo Interleukin-7", Immune Network 11(1):1-10 (Feb. 2011).
Kwitek A.E. et al., "High-Density Rat Radiation Hybrid Maps Containing Over 24,000 SSLPs, Genes, and ESTs Provide a Direct Link to the Rat Genome Sequence", Genome Research 14:750-757 (2004).
Lombard-Platet S. et al., "Expression of Functional MHC Class II Molecules by a Mouse Pro-B Cell Clone", Developmental Immunology 4:85-92 (1995).
Lupton S.D. et al., "Characterization of the Human and Murine IL-7 Genes", The Journal of Immunology 144(9)3592-3601 (May 1, 1990).
Mahajan V.S. et al., "Homeostasis of T Cell Diversity", Cellular & Molecular Immunology 2(1):1-10 (Feb. 2005).
Mazzucchelli R.I. et al., "Visualization and Identification of IL-7 Producing Cells in Reporter Mice", PLOS One 4(11):e7637 (Nov. 2009).
Mazzucchelli R.I. et al., "Interleukin-7 Receptor Expression: Intelligent Design", Nature 7:144:154 (Feb. 2007).
Mertsching E. et al., "IL-7 Transgenic Mice: Analysis of the Role of IL-7 in the Differentiation of Thymocytes In Vivo and In Vitro", International Immunology 7(3):401-414 (1995).
Munitic I. et al., "Dynamic Regulation of IL-7 Receptor Expression is Required for Normal Thymopoiesis", Blood 104(13):4165-4172 (Dec. 15, 2004).
Munoz M. et al., "Constraints to Progress in Embryonic Stem Cells from Domestic Species", Stem Cell Rev and Rep 5:6-9 (2009).
Murphy W.J. et al., "Antitumor Effects of Interleukin-7 and Adoptive Immunotherapy on Human Colon Carcinoma Xenografts", The Journal of Clinical Investigation, Inc. 95:1918-1924 (Oct. 1993).
Niemann H. et al., "Transgenic Farm Animals: Present and Future", Rev. Sci. Tech. Off. Int. Epiz. 24(1):285-298 (2005).
O'Connell R.M. et al., "Lentiviral Vector Delivery of Human Interleukin-7 (HIL-7) to Human Immune System (HIS) Mice Expands T Lymphocyte Populations", PLOS One 5(8):e12009 (pp. 1-11) (Aug. 2010).
Pleiman C.M. et al., "Organization of the Murine and Human Interleukin-7 Receptor Genes: Two mRNAs Generated by Differential Splicing and Presence of a Type I-Interferon-Inducible Promoter", Molecular and Cellular Biology 11(6):3052-3059 (Jun. 1991).
Prelle K. et al., "Pluripotent Stem Cells-Model of Embryonic Development, Tool for Gene Targeting, and Basis of Cell Therapy", Anat. Histol. Embryol. 31:169-189 (2002).
Rathinam C. et al., "Efficient Differentiation and Function of Human Macrophages in Humanized CSF-1 Mice", Blood 118(11):3119-3128 (Sep. 15, 2001).
Repass J.F. et al., "IL7-hCD25 and IL7-Cre BAC Transgenic Mouse Lines: New Tools for Analysis of IL-7 Expressing Cells", Genesis 47:281-287 (2009).
Rich B.E et al., "Cutaneous Lymphoproliferation and Lymphomas in Interleukin 7 Transgenic Mice", J. Exp. Med. 177:305-316 (Feb. 1993).

(56) References Cited

OTHER PUBLICATIONS

Rongvaux A. et al., "Human Thrombopoietin Knockin Mice Efficiently Support Human Hematopoiesis In Vivo", PNAS 108(6):2378-2383 (Feb. 8, 2011).

Samaridis J. et al., "Development of Lymphocytes in Interleukin 7-Transgenic Mice", Eur. J. Immunol. 21:453-460 (1991).

Schluns K.S. et al., "Interleukin-7 Mediates the Homeostasis of Naive and Memory CD8 T Cells In Vivo", Nature Immunology 1(5):426-432 (Nov. 2000).

Shalapour S. et al., "Commensal Microflora and Interferon-γ Promote Steady-State Interleukin-7 Production In Vivo", Eur. J. Immunol. 40:2391-2400 (2010).

Silva A. et al., "IL-7 Contributes to the Progression of Human T-Cell Acute Lymphoblastic Leukemias", Cancer Research 71(14):4780-4789 (2011).

Tan J.T. et al., "IL-7 is Critical for Homeostatic Proliferation and Survival of Nive T Cells", PNAS 98(15):8732-8737 (Jul. 17, 2001).

Tong C. et al., "Production of p53 Gene Knockout Rats by Homologous Recombination in Embryonic Stem Cells", Nature 467:211-215 (Sep. 9, 2010).

Uehira M. et al., "Immunologic Abnormalities Exhibited in IL-7 Transgenic Mice with Dermatitis", J Invest Dermatol 110:740-745 (1998).

Uehira M. et al., "The Development of Dermatitis Infiltrated by γδ T Cells in IL-7 Transgenic Mice", International Immunology 5(12):1619-1627 (1993).

Van De Wiele C.J. et al., "Impaired Thymopoiesis in Interleukin-7 Receptor Transgenic Mice is Not Corrected by Bcl-2", Cellular Immunology 250:31-39 (2007).

Van Lent A.U. et al., "IL-7 Enhances Thymic Human T Cell Development in "Human Immune System" Rag2-/-IL-2Rγc -/- Mice Without Affecting Peripheral T Cell Homeostasis", The Journal of Immunology 183:7645-7655 (2009).

Visse E. et al., "Regression of Intracerebral Rat Glioma Isografts by Therapeutic Subcutaneous Immunization with Interferon-γ, Interleukin-7, or B7-1-Transfected Tumor Cells", Cancer Gene Therapy 6(1):37-44 (1999).

Von Freeden-Jeffry U. et al., "Lymphopenia in Interleukin (IL)-7 Gene-Deleted Mice Identifies IL-7 as a Nonredundant Cytokine", J. Exp. Med. 181:1519-1526 (Apr. 1995).

GenBank Report, "*Homo sapiens* Interleukin 7 (IL7), Transcript Variant 1, mRNA", NCBI Reference Sequence: NM_000880.3 (5 pages) (May 4, 2014).

GenBank Report, "Mus Musculus Interleukin 7 (Il7), mRNA", NCBI Reference Sequence: NM_008371.4 (5 pages) (May 4, 2014).

European Communication dated Dec. 4, 2015 received in European Application No. 14 195 502.1.

Extended European Search Report dated Mar. 18, 2015 received in European Application No. 14 195 502.1.

New Zealand First Examination Report dated Jul. 20, 2016 received in New Zealand Application No. 702943.

Chinese Office Action dated Aug. 28, 2015 received in Chinese Application No. 201380031333.4, together with an English-language translation.

Written Opinion dated Oct. 7, 2013 received in the International Searching Authority from International Application No. PCT/US2013/045788.

Written Opinion dated Mar. 5, 2013 received in the International Searching Authority from International Application No. PCT/US2012/062379.

International Search Report dated Oct. 7, 2013 received from International Application No. PCT/US2013/045788.

International Search Report dated Mar. 5, 2013 received from International Application No. PCT/US2012/062379.

\* cited by examiner

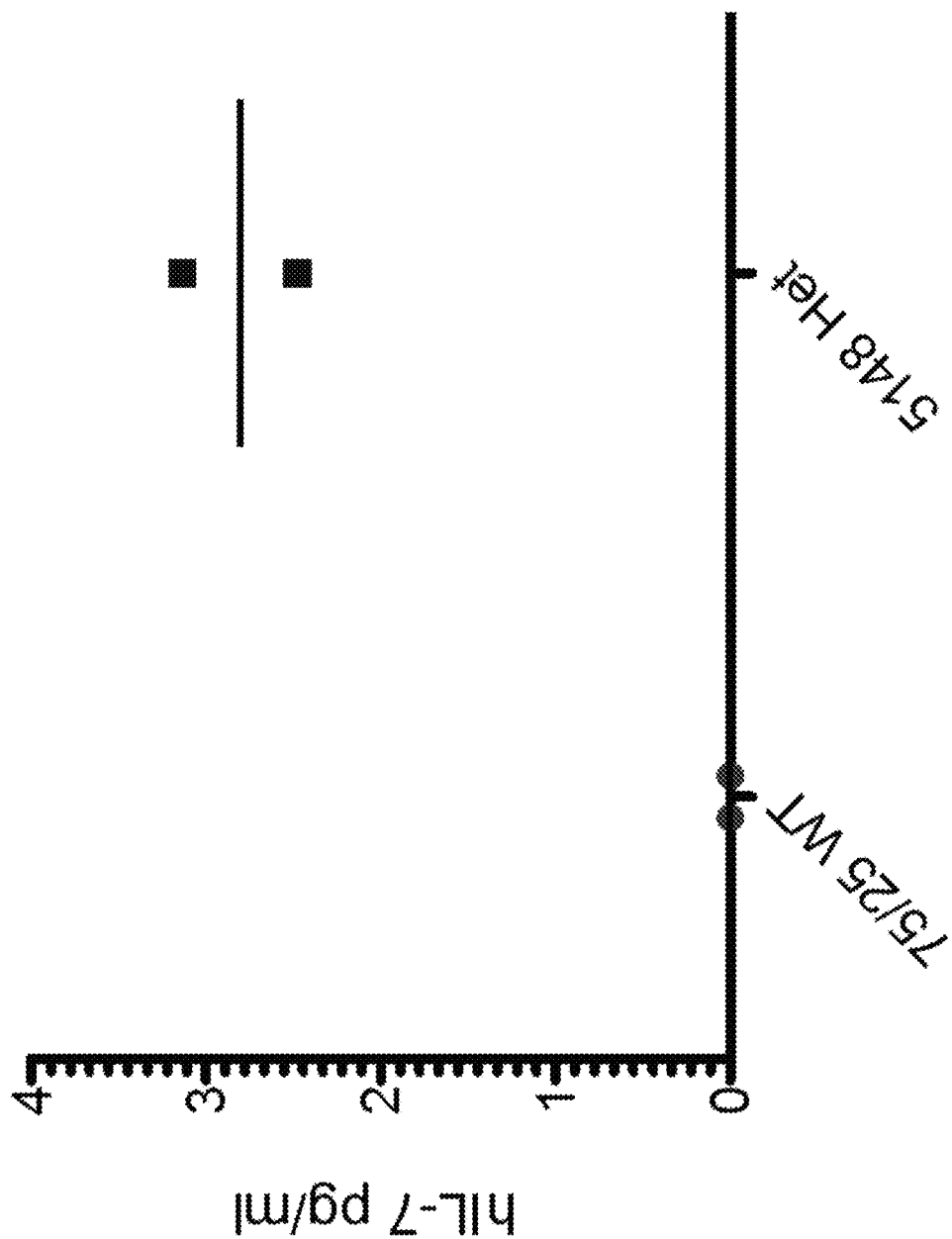

```
SEQUENCE LISTING

<160> NUMBER OF SEQ ID NOS: 15

<210> SEQ ID NO 1
<211> LENGTH: 8777
<212> TYPE: DNA
<213> ORGANISM: Mus musculus
<220> FEATURE:
<221> NAME/KEY: MISC
<222> LOCATION: (1)..(8777)
<223> OTHER INFORMATION: Mouse 5' genomic sequence present in humanized
      IL-7 mouse (from NC0000696)

<400> SEQUENCE: 1
ggcagatcct acggaagtta tggcaaagcc agagcgcctg ggtggccggt gatgcatgcg      60
gcccctcttg ggatggatgg accaggcgtg gcgtgggtga gaggagtcag ctgcctgaac     120
tgccctgccc agcaccggtt tgcggccacc cggtggatga ccggggtcct gggagtgatt     180
atgggtggtg agagccggct cctgctgcag tcccagtcat catgactaca cccacctccc     240
gcagaccatg ttccatggta agcgctgctc tctggtgcgc acaagtaggt gcgcctagcg     300
cgccggggac tctgggacag tccggaggt gccacccgcc cccgcgcctc cgcacgtccg     360
ggaatagccc ggccttgcac tttggacagg ctgagagctt ggcctctccc atggtcagcc     420
actacccgcg ctgagctcgg ttgcccagaa ccattggcac ctgggcgtac aaccctggcg     480
ggcggggagg aacagttccc gaggcggttt tcagatcccc agacccagag cttcagtgcg     540
ggagccgcga cgcggtggcc ccctgcagtc aagactcagt agtcagtggt tttcagccac     600
tttgtcccta gccagtacct cttcaatgca gcccttcctg gcttcctggc tgtgcagtta     660
ctcacaggct gcctggttc agggcgttgc tgggctctcg cagctcagaa cttcatggag     720
aatgaaagag tcgctcccag gatgcgcttt taaaccctaa aggacagatc attggaaaac     780
cccctcttct ccccgcagta agtctgggag tttccgatcc aggctgtaag ttgacttgtt     840
```

```
tgctgggaac ccaagtcctg cggctgagat tgcaaaaggc cagatttat tttccttcta    900
tatatttgct acttaaggga ggcagaactt aagtaccca tgagtacaaa ttcttagctc    960
cctgatcaaa tctaataggc ttgcattagt tttaaataag taaggattta aagtggacaa   1020
gaacagaatt gacagaggct ggaatccatt tgtagctaga actaatagag atgagaacag   1080
aatggagtgt gaggaggtct acctaaggga atgcaggtgt tttaaatact tcctcaagca   1140
agagaaccta tggaggtgca ggatctagcc taaggctctt tccttttgca accccattgc   1200
aaaccattgt attggtttcc ggcccactgt tttaggtaca attacttccc ctctcttagg   1260
tactagcgaa ccaaaaacat ttgagggagt acttatcaga aaccaaataa agatgtggaa   1320
gacctgagag actgcccaag aaaatgatgg aaggctgcca aggtgcccct gcaggagctc   1380
actgtacagc tagagacacc gcatcccgtt cttctttgca atgccctggg ttctgaaatt   1440
gcctttcact ttaacccttg gattacctac aacctggaga gataaaagga caaggaaaa    1500
gcaaggtgt aatttaaacg aggagctttt tcccattgag atacatccat atcgacatg    1560
ccttatttc ttagtaaaga aaatatgaaa atattaaact cacgggagtt aaagtaagtg   1620
gcttttttt ttctttcat tttcggtcca aaatttacta gaggcgtggg taaactccat   1680
caaggctgtg tgctgtgttt ccactttgtt atgtcgggac accaagtaaa caaggattca   1740
ctcgctgacg ctcaattgtg ctgcctcatt atgaatcagc atacatttta tttgtatact   1800
aataaaagga aacaatgaga aacatagagc cttgggaata tggaggaagc ctgaagatct   1860
atctgtaaag gagaattaga aatttcatct cagtgtgtat acttcttgaa caaaaatgga   1920
aagttctttt ataaaaccaa tctcatggcc catgggtatg aagtactgtt atcctgactc   1980
ttgacagata atttgtttt ttaattaatt tattttatt ccttaatctt ttttttaca     2040
gtacagactt tatacctctc ctgttctgcc cccccact gctctcctcc ccatacctcc    2100
tccccagccc ccaccccacc cctgactcca agagaatgcc ctcatccccc atgccactag   2160
gcctcccac tccctggggc ttcaagtttc tcaacagtta ggtgcctctt ctctcactga   2220
ggccagacca ggcagtcctc tgctctatat gtgttgggga cagacaactt tataatatgt   2280
agaaatattt acttttccc ttgaaatagg agcatacgct gtagtttcag agcttggcca   2340
agaagcccct tcatgtagaa gacaatgaat atttgtactt cctctcacta tctgtgcatg   2400
cagttatgtt gtaggaagtg taattcagta gctaatagcg gattccctag acacctcaac   2460
ccgaacatca aatgcagctc ctgaatccct agaaaaattg ttttggagaa ttgttctttg   2520
ggctccagat tctctactgt aaactgctag tgacctgtat atatatat atatatat      2580
atatgtatca tgaaatggct ataaaattga attatttgtt gaaatagact tgggaaagga   2640
cattgaaaga acacttctca aggaggatgg gaaagtcctc aaggtctcaa ccctagacaa   2700
actgttcagg ccacgaagaa atgctgactg acagtggaga aatagacatc cccagagagg   2760
agcatacaaa ttgtttatcc aaacagccag ccctgaagac atatgtgcaa gtaaggttat   2820
acagactggg caggttgact ttatgtattt agggagatag atggatgata gctagctagc   2880
tagctagagc acaacactta atgaaataaa aggtcatgaa tttgaaatag agcaagaaag   2940
gatatatatg agagtttagg ggaagaaatt gattgaggaa ataaaataat gatgttgtaa   3000
tctcaaaaac taaagaaac tgatagatga caggatatga tggactgagg aatccaattt   3060
tattatgtcc actttgacct cataacttaa gcagttgaag attgtatgta ttatttggct   3120
tacatttaaa accaacaaga attttagac agctatcatt ctggtttaac caaattcccc   3180
```

```
actgaaaaca aattctccag tttcaaaccc tgtaagcgat ttaaagacaa tactacaagc    3240
caacacttgt cttgtaatgc ttctacagtt tgttttatct gtgacctaat gaaaagttca    3300
gtggaggctg aggagtgagc tataaatcaa aagtaacaaa atatggtaag tgctgaattc    3360
ggatgccatt gggacaaaag tgttaaataa actttcaaac cagaaaaata ttaacttgtt    3420
acggtgcttg tatgtggaag aaataactgt aaccacagaa caaggtcac actcctgatg     3480 gtggagccag aaacccatgg gatcatacat tatcatacat atcatacatt agagagcctg    3540
gaaggttttc attttagaaa tcagggccag gaagctgaaa tgaaactcag ctatttagtc    3600
agttacacaa aatcctaaat tctctatgct ctaaatctcc ttgtttataa tatatatact    3660
atttatatgt attataaaat attaagtata tattataata tattaaaata tgtatggtac    3720
tgctctggtc tgtcagcagc tactttactt gattgaaata gtctacaaat gaagggctgt    3780
attgtaaaaa tagtatagaa ttgaaaattt cacgtaacac acacatgtat tatcaaagca    3840
agtgtgaagc aatgaaaaag tgctgcccgg tgaggtgtaa ggtcacatca ttctgggaag    3900
cacatatctc agaagaaaac tggcaatctt ggaaagtatg gcaaatgaac ttattgaaac    3960
aggaaatgga ctttgaaatg acttttagat ataggtgcga attaatctct tttcactaac    4020
catcataact ttctccttg agttcaagtc acattccctg tctctttcat ttgcctggtc     4080
cccccaaaaa cataattttt agggacctat aaggcaaaag atgaaataaa agccagttt    4140 ctacaaaaaa tgtagatggc tataatccaa ttgagtagta attgatacct gtgtatccca    4200
gtgaagggca gtcataggag aaggctgatg aatggtatta tgagaaggtg cctttcaaac    4260
agaatagcag cagataagat gttatcaatt gattatgggt atttaaaagt gattgtcatt    4320
ttctccccct cttgaagcag atatagatca gattaggcca gattaaaagt agataaaggc    4380
agttttgtta ggaatcccct ctctggtggg ttcatccatc tcacaggtgg aagtcagtga    4440
agtcacacag ccaggctaaa gcatgggggt tttatagagc ttaagcaggg agtagtgatg    4500
tgccagaagg agctaggatg gtgtccatac gtggtcaaaa actgagcccc tggtgggcac    4560
tctggggtgt gttgcaggaa cccagggatg agacatggcg acttattggc ctagagtttt    4620 ttgttttttgt ttttgttttt cccaagcagg ggttccgggt gcaggcaggg ttggggaaag   4680
gagggtagct tccaagtggg gtttccctgc ttgttcagaa tatgagcagg agttccagcc    4740
taacaccccg acctcttggg gtatagatac agccacactc tgctgaagag ggacgggaga    4800
gttgggagcg ggtgggatca tactcatctg caggcatgct gtaggaccat tcggtggtgt    4860
gttacttaga aacttttatg aatccgttcc tggatgaaga gaaggtagca aggtgctagg    4920
aagatgtgca tgtgcaaggt gctaggaaga ctgaggctag ccatgtgaag agtaacactg    4980
ctagagagaa ttgaatgtgt cttggttgtg ttgtgggaac tctttagaca atttgcggag    5040
tgactctgtc caggtctcca caaggccaga ctcactgatg taagagtggc agggacatgc    5100
agatgccgcc cttaccagtc atgaggatac ttttagggcc attgaagcct ataagaatct    5160
tattaagttt acagagagag agagagagag agagagagag acagacagac agacagacag    5220
acagacacag agacagacag agacagagat tttagacatg ttagacagta gacttatacc    5280
tttttgtcat agtacaggct tcggaaacat taaaatttga ttattattaa agctttgaat    5340
tttgaattct taatataaca gaaacatagc tagggaaga atctgaagca ttttttttaaa    5400 aaaatatatt ttatgtcatt ttttctcttt tgtcttttaa cctttataac ttgcatttat    5460
taactttaaa catcttttat actatgaaag aactttctta catcctttga atttaaactt    5520
ttatatactc agaccaccta tgggttttc tctcttttta tccagatatt gaccatgact     5580
```

```
cgtaggtagc tgatcattga gagcagttat tgcaaagtga gttcctttag ataaaggaat    5640
attgaaaatt ttatattgaa tttttcagtc taataatgag ataaattgta tctagccaaa    5700
gtagtggcat gtcttggaga gtgtcgtttg aggactgatt tttacacatg aagaggactg    5760
ggaaggtagc tgaagtcttg gatcctgatg ttaaatgaat cctcaaaccc accagagtcc    5820
tgagaaggat caattttatc tgagtaagga gggaactgca agagcaagca gtttctgagt    5880
ctattaaaaa tgacacagac ttacaggact ccctggacag tcagtcatcc aggaattctc    5940
tgtggtcagt ggggcatcca ttttggctat caggccaaga aaatctggca gactttgtgt    6000
gtgtgtgtga atcaagacta tgagaaaaag actgccctac cttgtctagg caagtgaatc    6060
agtcaacttc ccagtgtcct acctgtccac agtgtggccc atgtgctgtc aacagtcgca    6120
gcaaagggct ctttatagcg agcaagcttc aggcagaagt tcttctgggc tgtgttcttt    6180
ggaggagatc aggggtgctg tcaagagctg gtgtgtctct gttatgaaaa gcttttttcat  6240 tagccatttt aaatgccata ttttatagac ctctgaagcg tctgaggacc atttgtgtct    6300
ctacagtata tctaaataga caaacgtttg ttttttggct attcaatttt tatttaactt    6360
tgaaaatata gataggaggc taagtaaaac ttattttggt aattaatcat aattataagt    6420
gtagttatga acatattaaa gaatgtgatt attttttgagg taactgataa ctaacttgta   6480
tgttttaata atgtttaaca gcttataata aatgctgtat gttatattta acctgaaggc    6540
agtgttagga cagaaaaggc ttaataagtt ggaaaaatgt ctcagtagcc cttcatgggc    6600
ctaaggaaaa agagtcgctg tggcccaggc ataggtttaa ggaagctgta gttactggag    6660
gaaatggagt gaccattaag ttaaggggtg tgggagaggc tgatgtgctc agtgtatgag    6720
caatgaggtc tcctcacagg acaggctgga ctgtgcagag tggataggggt ggacatggga   6780 gtgagtgtag ccttgcccca ttggcgagga gaaaagccag gttaccagga ggaagaggag    6840 gaggagggggg gggggaagtg gggggaggag gagggctgct gaagctttaa cagagtgcag   6900
gcgaactgaa aggaaggaat cctgcggggt tacaagaacc agagccatgt ggaacacata    6960
gcaggctaaa gaatcggact tcagaattta gaatcaaatt tccagacaag taagtgatcc    7020
atacacactt tgggaggatt agcatggttt ggagcaacca ttgcagttac aaaaggttga    7080
gtgtgtcaaa gagaagaagt gggaagagtc tgggctctgt caatacaggg gtttggggtt    7140
tgggatccag gtccttggag gcaaggggtc ttttggagtg aacatccttg ctagtaggac    7200
gtgagcctta gaacattggc tacagaggaa gggacagggt gtggttccca acaaacctgg    7260
ccagaaggga ttcaggccat ttgcccgcat accaaaagaa atgttaagct taagatccgt    7320
ggagaatttt aacatcaaga atgctctctt gtggccgttt actgaagcga ggccatagaa    7380
caaagtctga gacagtccta atttggacaa cttttgtagc agtcacccca ggaatgtctg    7440
aggatcaggt ttagactccg tgttgcccat ctcctagact tgtggcgacc tatgatacag    7500
tgtcccactt ggtagcctgg ggtaaaacag tgaggagtaa agaaaccttg taaaggatat    7560
ctcagaatcc aaatactagg ccatggcttg gcagaggatc ttggtaagtt caaagttgat    7620
ccttcagatg aagagagaaa gggagagaaa ggagcagacc ccatgcagcc atggtccctg    7680
cccgctgggc tgcaggctca acttctcccg cattttgaac caagatgata ggaattttct    7740
ctccatccat gaagcagatc tagggcagat tgatgagat aaaagtaga tacaggcagg     7800 tttattagaa gacaactctc aagtgggttc accgatctta cacatggaag tcagtcaagt    7860
cctatatctg ggctaaaaag caagggaggt tttatagagt ttaggtgagg aatgatgcca    7920
```

```
tgccagctag gaactgggat ggtgtgcata catggtcaaa aaatgagaaa aaaggagtga    7980
tagctctttc ctgtgcttag cacgatttag ttgcctgtag ttcttttgtc tatagttgta    8040
gctctgtgag attctgtaat ttcgaccaag catactttct ttacatatat atatatatac    8100
actcagctgc taatttatgg tggatttata aataaattta tttataaatt tataatttat    8160
tgccttttta ataccatgta taatagtatg atatattgca tcctatgata tccttacatt    8220
ctttaagttg tttccaatgt caattccttg ggtttagaga atattgtttt agacttttaa    8280
atagagaaga tgcacataaa atgctgaaca ctgggatttt ataacgttaa tttgggaaaa    8340
tcatggtaag tatattttca acataactga gttcagggaa aaatgaaagc aagattcatg    8400
aagatatagg tggcttaacg ttttatgta ccagaagttt ccatcttaat tatttactcc     8460
aagtgatgat tccatttaaa atctccttcc ttttaattaa acagttcact ctgattggca    8520
tgacttactt gatgtagtca taaacaccag ctgagaggtc tcgagtctat tgtgtgaact    8580
ttgcctaaca gggaaggaat ttaaagagag ctatgcttga acagaatcta ggtctttggg    8640
aaaatagata cacaaaataa tgacataagg gaaagagttt gcgaacatga tttaggggc     8700 aaagtaaaac tctgtaaagt ccatcacaaa gaatcgccat agtgcaagca ccaaaaaggt    8760
gaccacactt cacattg                                                  8777

<210> SEQ ID NO 2
<211> LENGTH: 944
<212> TYPE: DNA
<213> ORGANISM: Mus musculus
<220> FEATURE:
<221> NAME/KEY: misc_feature
<222> LOCATION: (1)..(944)
<223> OTHER INFORMATION: Mouse IL-7 downstream (3') genomic sequence
      from the humanized IL_7 mouse (from NC00000696)

<400> SEQUENCE: 2
ccaattgcgt actttggata gtgtctcttt ttaacctaaa tgacctttat taacactgtc      60
aggttccctt actctcgaga gtgttcattg ctgcactgtc atttgatccc agttttattg     120
aacacatatc ctttaacaca ctcacgtcca gatttagcag gagactagga ccctataact     180
ttgttaagag agaaaacact aatttcttgt tttatagtag ggtcttattc gtatctaagg     240
caggctagga ttgcagacat gagccaatat gcttaattag aaacattctt tttatgttaa     300
actcatgtct tttacaagat gcctacatat atcctatgta tatgcctgtt taaatccttt     360
tttgtaaggt ctgctgtctt ccttcagttg taatggaaag aaacactatg ttgtagaggc     420
caaatttctg aaagtgataa gggtttgctt gtactgaatt ctcattctcc ttgctttttc     480
cagccacgtg agcatctagc tatctatacg ctggatgtat ttgaccgatg cctgctccac     540
tggcacattg catgtgtggt agccatgcct tcttgcttct ccttttcccc aaccctata     600 atgctctact cagtggtaca gatagctggg attatcacaa ttttgagaga aacaccaatt     660
gtttaaagtt tgtttcataa tcaccatttg cccagaaaac agttctctca acttgtttgc     720
aacatgtaat aatttaagaa actcaatttt gttaatggac tttcgataac ttccttagat     780
atcccacatc tcctacgtgt cagtccttg tcctgaggaa ctggtaaaat gggtaagccc     840
ttagctagcg aactgaaggc attcgcatgt gtaagataat ctctatacct gcaaggctgt     900
ctggatggct ccctaccaat attgaacaat attctgattt tggc                     944

<210> SEQ ID NO 3
<211> LENGTH: 72752
<212> TYPE: DNA
```

<213> ORGANISM: Homo sapiens
<220> FEATURE:
<221> NAME/KEY: misc_feature
<222> LOCATION: (1)..(72752)
<223> OTHER INFORMATION: The human genomic IL-7 sequence (NC#166E2F2)

<400> SEQUENCE: 3

| | | | | | |
|---|---|---|---|---|---|
| acatccgcgg | caacgcctcc | ttggtgtcgt | ccgcttccaa | taacccagct | tgcgtcctgc | 60 |
| acacttgtgg | cttccgtgca | cacattaaca | actcatggtt | ctagctccca | gtcgccaagc | 120 |
| gttgccaagg | cgttgagaga | tcatctggga | agtcttttac | ccagaattgc | tttgattcag | 180 |
| gccagctggt | ttttcctgcg | gtgattcgga | aattcgcgaa | ttcctctggt | cctcatccag | 240 |
| gtgcgcggga | agcaggtgcc | caggagagag | gggataatga | agattccatg | ctgatgatcc | 300 |
| caaagattga | acctgcagac | caagcgcaaa | gtagaaactg | aaagtacact | gctggcggat | 360 |
| cctacggaag | ttatggaaaa | ggcaaagcgc | agagccacgc | cgtagtgtgt | gccgcccccc | 420 |
| ttgggatgga | tgaaactgca | gtcgcggcgt | gggtaagagg | aaccagctgc | agagatcacc | 480 |
| ctgcccaaca | cagactcggc | aactccgcgg | aagaccaggt | cctgggagt | gactatgggc | 540 |
| ggtgagagct | tgctcctgct | ccagttgcgg | tcatcatgac | tacgcccgcc | tcccgcagac | 600 |
| catgttccat | ggtaagcgct | cttctccctt | gcgcacaagt | tcgcgcgccc | gacgcgccgg | 660 |
| ggcaatccca | gacgcgctgg | gggcccctgc | tcctaggcaa | gtccgggaat | agcccggcct | 720 |
| tgcactttgg | acctgcggag | agcactggct | ctcccatggg | cagccaacag | ccgcgcctga | 780 |
| gtatcctggc | acatagccac | ttgaacctgg | ggcggctgct | gcccctggca | ggctgcgagt | 840 |
| aacagtcccc | aacgcctgct | ttctgtcctg | agagggaacg | ctgcagcctc | cgcgccgctc | 900 |
| agcggtggca | gcccacagcc | ggtctcagaa | gcagccaaag | gctctctgtc | tggcgccctt | 960 |
| cccgtgctcc | tggccgcccc | aagttactca | cgcaggcggc | ccgggttcgg | cgagtagctg | 1020 |
| ggctcttgca | gctcagaact | ccctagagaa | gtgaaagcga | agctcccacg | ggacgcgctt | 1080 |
| ttaaacccta | ggggaacagg | tctccggaaa | acccccatttt | tcccccctga | gtaagactgg | 1140 |
| gagtttccgg | caagggctgt | accttgcgcc | tattgctggg | aaaccagtcc | tggggctggc | 1200 |
| gctgaggaag | gccagcttct | gggttttttt | gttttgttt | ttgttttgt | tgttattttt | 1260 |
| tcctacgggc | gcttcttgat | ggaggcagaa | tgaaataggc | gtgactctaa | cttccagacc | 1320 |
| agtattgaga | cctaatatat | cttatttgtg | cagaatacgg | atttagaatg | gacagggaca | 1380 |
| gaattcagga | gggttggatt | cggatggcag | tcatatatga | ccaatgaaag | agccaaaaaa | 1440 |
| cttactggaa | ttaaaaaaga | ggaaaaagga | ttgtgagggg | aaaagatctg | cttaggaaaa | 1500 |
| ttggaatgct | ttacagtaag | tacttcctca | agcaagaaga | cagctggggg | gagggtgcgg | 1560 |
| gaataggaaa | ctgactgctc | tttcttttga | tggctactcc | gttagatcaa | gacttctttc | 1620 |
| cactctcgtg | ggtaaagaat | caagaattga | cacaaccaag | gagtgccagc | tcagtaacaa | 1680 |
| aacaaagata | gagagagcgg | aaagaatagc | caacgtaatt | atggaggact | tctaaggaat | 1740 |
| gtcctcccgg | agcttaatac | aaaactaaaa | attgagcaca | accctatttt | ccttgcaatg | 1800 |
| cccatagttc | tgcagtttct | tcttctggat | caccccttggt | tctaatcctt | gcaacacctc | 1860 |
| tgctctaaag | tagaaaggta | aactgagaaa | aggaagctag | cgtgtgcatt | tttcagaaaa | 1920 |
| agcctttact | tcctgaagca | cagttatatg | aatcatgggc | tataagtttt | cattagcaga | 1980 |
| caaaatatta | aaattctaat | aataatgatt | ataatgcatg | gcttcctgaa | gtttgtttca | 2040 |
| agaaatttca | ctgaagcttt | gttccattaa | gagtgcacat | aatgttactc | tttacccttt | 2100 |
| gtctttgcca | tttcttttga | gagttgaagt | agttgaggat | ctactatgtg | gtctccaact | 2160 |

```
gtcttatctg gtttgggtaa tttcatcata tttgaggacc aaaaagttga atagcaataa    2220
aaatagactc tactcgggag gctgaggcag gaggattgct tgagcctgga agtcaaggct    2280
gccgtgagcc atgatcttac cactgtcctc cagcctaggc aacagagtga tgccctgtct    2340
caaaaaataa taatagagaa ctaatattag aaaccctgaa caagcataaa ggagaattac    2400
aaactgcatc acgttagtgt ttgaatattt ttttaaaaaa tggaaaaggc catttcatag    2460
aacgaactta cgtgtcatat tcacactcat ctatgtgact tttttttctg cttttaaccc    2520
tgacacataa cctactgtaa caagaacaaa tatttagtct cttttttctga aataaaagca   2580 tatgatgcag tttcacagtt tggccaggaa gtaccttagt gaggttcatg cacaggaaga    2640
tgggttttta tgcaatcccc ttgactacac atatatggtt attttttaag gaagcaatgt    2700
agttcagtgc ctaaaagctg aggttctaga ctcttcaatg tgacagtctt ggatttgaat    2760
tccatatcta tattatgtac aggaattttc tgactaggca tggtggctca agcctgtaat    2820
cccaacactt ggggaggctg aggtgggcag atcaccttag gtcaggagtt cgagaccagg    2880
ctggccaaca tggtgaaacc tcgtctcaac taaaaataca aaaaatttg ccaggcgttg     2940 tggtgggcac ctataatccc agctactcag gaggctgagg gaggagaatc acttgaacct    3000
gggaggctga ggttgcagtg agccgtgatc gcaccattgc actccagcct agatgataga    3060
atgagactcc atatcaaaaa aaaaaaaaag agagagaaaa atacgaaagg aattttccta    3120
catgactgtc tttgtgcccc agattctcca tctataaatg tgaataactt gtagtactta    3180
cctacttctt catgaagtgg ttatggaatt aaattatcag tgaaaatagg tctatgcaat    3240
ggacattcag taaacactgg ttttaaagac tgataaagac tggagttgat ggattgtaga    3300
aaactattta tgttaacttt gaccccata acttaagcag ctgaggattg aatgtattat      3360
ttggcttaca ttaaaaacca acaagaattt ttagacagac ctccttctgg tttaaccaaa    3420
ttccctactg aaaacaaatt ctccaatttc agcctcttca ggggaagtaa gggcaatccc    3480
acaagccacg cttgccttgc gttattccta tggtttatct tttcggtaac ctaatgaaaa    3540
gttcaggatg tgggggagtg tgggtgtgac aacaatgcca aaagcactct caaaccagcc    3600
attcttaata tgttactctc tatgtgatgt aggagaaagg tcttcaatta tggaccaaac    3660
taccaagcta catcattaat gggagagctg ggaacctatg agatgtgggt ccaaggccct    3720
aggtatgttt gcagcattgt ccgtgaggca atttcagatc taaagagttt ctgcatttgg    3780
aggaccaggt agattcttag aataaggtgt ctgcaagatg aaaaagatca tttagtctga    3840
agttttcatt ttagaaaatca ggtaagtgac cttaagagat gctgtgtcat ttacacagtc   3900
acacaaacca ttgtcttggc aagtcaaaag tctcaagttt tgacttgact actcagccta    3960
ggctcagtag atcgtggctc acggccatgg cttacggcca tggctcacgg taagatcatg    4020
gctcatggca gccttgactt ccaggctcaa acaatcctcc tgcctcagcc tcccaagtag    4080
agtctgtttt tattgctatt caacttttg gtcctcaaat atgatgaaat tacccaaacc     4140
agataagaca gttggagacc acatagtaga tcctcaacta cttcaactct caaaagaaat    4200
ggcatagaca aagggtaaag agtaacatta tgtgcactct taatggaaca agcttctagt    4260
gaaatctctt gaaacaaact gcaggaagcc atgcattata attattatta tgagaatttt    4320
aattccaaaa cctctgtgct ttatattgcc atagtctgtc tggggctaat tattcaatga    4380
caacaatggc aacagaaaac actcttaaca ggcaaggcaa attatgtttt aaaattgaga    4440
aagtacgtgt aatatacaaa aagactgaat tttccagcaa ccctcattgg aaagaatgca    4500
```

```
caaaatgcca tccggtgaat aaataggttg atttaaattt gaggagcact taactactga    4560
aaattgaggt gaagaagaca gctaatgctc atagcaagta aaacaacctc atgtattaaa    4620
acaaaaggtg gacctttgga atatttatga taatggtaaa agtatcccct tcactctagc    4680
atttaattat tttattatat tctcctttaa gctcatttca agttatatgt tatataattt    4740
ttcctctatc atctactcct cccgaagtat acctttggga cccctgtaag atgacagaga    4800
aaataaaaag tatgatttca tacaatctat acaaatctga ttacaaggtc agaatctggt    4860
gaataattag caattgatca tccaaatgtc catcagcaga ggtttggata agaaaatgt     4920 ggtatggccg ggcttgtaat tacagcttgt aattctgaca cttaaggagg ctgaggcagg    4980
aagattgctt gagcccagga gttcaagacc agtctgtaca aaagagtaag agccgtctgc    5040
taaaaacaaa tttaaaaaa ttagctgggc atggtgggc acctgtagt cctagctact      5100 cagaacgctg aggtaggagg atcgcttgaa cctaggaatt tgaggcttca gtgagctatg    5160
atcatgccac tgcactccag cctgggcagc agagtgaaac cctgtctcaa aagagaggg    5220 agaaaaaaag aaaatgtggt atatgtatac catggaaatac tactcagcca taagagttaa    5280
gtcgtctttt gcagcaaaat ggatgaaact tgaggccatt atctaagtga aatgactcag    5340
aaagtcaaat gctgcatgtt tttacttata actgggagct aaacagtggt acagatggac    5400
atacagggtg gaataatagg cattggagac tttgaaaggt gggagagtag gaggggata    5460 aggattgaaa aattacctat tgggtaccat gttcactatt caggtgatag atacactaaa    5520
gcccagactt caccactgta cagtatatta aatatgtatt agtaagaaat ctgctctggt    5580
ccccctaaaa tctatgagtg tacatttttt taattgccaa aatattttt ttaaattagc     5640 aattgatcac tgaggatctt taggttgaag gaacaggagt agaagagaga ggcaaaactt    5700
cattcagaag acaaatgtga ttacatgtta tcaatagatt atggccattt ctaatcgaat    5760
cctggtaaag caacaaattc aggttagcat ccaaacctgg cacctactat gtatgtgtta    5820
cagaaagact aacttgcaga acttttggaa tatttataaa tcatatatat atatgaga     5880 ttttatatat aaagttcctg acacatggta ggtactcaac taaaggtaac tagcatcatc    5940
atcattatct gtctcctaag ttaattcatg ctcatcatgc atataggcac ttagtggcag    6000
agttattaat atatttgtat aaataaaatt atcaattttt gtttctctta ctatgttgtc    6060
acatatgcag atgagaagtt agattatgt ttgttttcat aattgctacc cagaaaattt     6120
tctctatttg taacaacatg ggtcacttga tttattggga ggtgttattg attgttttat    6180 atgcacagatc atgatataat agatgacaat gttactggaa actttatgat atccctaaca    6240
gtcttcaggc tgtcacaata ttagttcctt gggtttgaag gagtgttgct tgtactctta    6300
atcgagaaag gcacacaagt gaaatatctt gcattcaagt acaattgaag ttcatttggg    6360
aaattcacag gaaatacatt gtcaacatgc ctcagagttt acaaaagat acaaataaga     6420 cactatggca ggtttatgaa gaaataggtc cctgtatgat cagattttaa tgtttgtggg    6480
aaccactggc tttccatctt tctgcctgaa ataaaccat tatttcagtc cttttgatta     6540
gacaattgct cctaattggg aagagttatc aaaaacagat agaaatcatt ggtttctatc    6600
tgaggatgtg aatttattta cagagttttt ctaacatgac aagaagctgg atagcgctgt    6660
gtttgaaaag aatctgggtc tctggggact cagagacaga agatagtgaa aggataggag    6720
agtagtccca aaatacaaac ataaactttg taagactttt gggaatgtaa acccttcagg    6780
gttcattatt aaaagaaag agtgcactta cagtagttac agtgcaatcc cagggagatt    6840
aacctcccac agtgttgcct ccaagaagca aatagacatg gactaccatc aaggtttaca    6900
```

```
aaaatataca attacgtgca gtacatcata aaattccaac aatatgtaac tcttcgaact    6960
gtagtgcacc tctttacctg tatatgcctt ttcttatggg gatgttcaac ataaattcaa    7020
attgattaac accctggagt gttttttcaga agcagtctat gatttcatca cccttgtttt   7080
gcactttcct aaagagtaat tgcaaaataa aaagtgaaa ggacgctata ctccaaaatg     7140
ctgttccact ttggttgtta cataagttca acttttgagg ttcttcctgt agtatctcca    7200
aaccaagatg tattttaaaa attattagaa attagtggtc cagtccattg aaacccaca     7260
atcaaatgca atacgatata acatttagct cattcttatt tactgtcaaa tttagtttct    7320
tttaggtata tctttggact tcctcccctg atccttgttc tgttgccagt agcatcatct    7380
gattgtgata ttgaaggtaa agatggcaaa caatatgaga gtgttctaat ggtcagcatc    7440
gatcaattat tggtatgtga ttattttgtt ttactcacat tttcatgcat tgggaaaatt    7500
tgaaccttt tggtatgcag ttttataatc aagtattcat ctttcttgac aagaaagtga    7560
agtaactata gaataaaatt taatgagcta ctaactgtat atttttatag ctgacataat    7620
tatgtagctt aaaaataatt ctttcctcga ctctaagatt ctcacaacta ttcatttcag    7680
tcctatttcc ctttagtaa atttcttgta agcataattc agtatcactg cctaaatttc     7740
ctcacctccc atttaccatg ttagtccctg tagaagcatt acattaagag tgggaaaata    7800
acagagtaaa tagttaagac ttatggtgaa tagatgtgta tttatttgg ctgtgtgtag     7860
atgcatagtt atttatatgt gtgtatttta tatctatgtg taatcaataa tttgttatga    7920
gttaaatttt ctattttga tggttaaagc ttttctaatt aatagatttt ataccttaga    7980
gccaacttag gtttctagaa aattcgagca gaaagtagaa aattcccata tgctctctct    8040
ctctctgcac tgtttccctt attatcttac atcagtatgg cacatttatt acaattgatg    8100
agccagcatt gatacattac ataagtgcat agttaacatt aggattcatt ctttatgttt    8160
tatagtttta tgggttttga taatgtata ccatcacata tccgtgatta catatcatac    8220
aaatcatatg gtaaaaatct cctatccacc gactcatcct tctctttctt cccctgaact    8280
cctagtaacc actgatttgt ttatgtctct gtagttttgc cttctttaga atgtcatata    8340
gttagaatca tgcggtctgt atgtggcctc tttagactgg attctttcac ttagcaatgt    8400
gaatcaaagc atcccccatg attttttgtg gtttgatatt tcattttttc ttattgctgg    8460
ataacagtct attgaatgga tataccacaa cttgtttatt ttttcactga ttgaaaaatg    8520
tgtcacagtt gcttccaata tttggaaatt atgaataaaa cttctataaa catatacgtg    8580
cagggttttg tgtggacata agttttcaac tcaggtaaat acctacaagc atgactgctg    8640
gatcatatgg taagactgtg tttagctctg tacaaaactg ccaaactttc ttccaaagtg    8700
gctgtaatat tttgcattct taccagcaat gaatgagatc ctaatgcctt ccatcttcgc    8760
cagcctttgg tattatcagt tttgcagatt ttaaccattt taataggctt gtcatagtat    8820
ctcagtgttg tttcaatttt ccattccata atgacataca atgttgacca tcttttcaga    8880
tacttttgc catttgtata tctgctttgc tgaggtgtct gaactcacat ttttactgaa     8940
atcttaacaa tattgagtct tcttagccat tatccatgcac tatctctttt ttaattttt   9000
tcatcattta attgtattat ctggacagag aacaaatgag tattactgtg acaacatttg    9060
taaataatta tatgtgtgta aaactctgca aaagaagatg caattgaaaa tgcaaacttt    9120
catcagagct ttgttctttt cagcatataa atcctgtaaa tattttatta gacttatacc    9180
taaatatttc atatttagt gctatttaa atggtgtgtt tctaatttca aattttagtt      9240
```

-continued

```
gtttattgct ggtacatagg aaagcaattg attttttgtat attaacctat gtcctgcaac   9300
cttactataa tcacttgttt gttctagaag tctgttgttg attattagga attttctaca   9360
tagacaatca tgtcatctgc aagagttaat ttttccaag gtttcagagc tgtatcaata   9420
caatgtgatt gatttattgt tttaacagat aattagtctc ttttcaatca gattgaaact   9480
gaatagcaaa ggaaaactct ctcaaatgtt cataagatgg gagaaattgt ctaatctgtc   9540
ccccgacttt tactccactg tctcttccac atactcatac tgaagtggca tgatgccttg   9600
aggaatttag tgttatacct cttgtaggaa tatggaaact aaaagagat actgtgctac   9660 actgtacatt gtaatccaga ggttcctgat tttgcccatt gacaagaaaa aaaatagtgc   9720
acagtaaatg gcaattgctc catttagatt tcttgctaat ttggacattg catttgatga   9780
tgctactaaa ttaatctttt gagtcaagat aatatttctc atttaatttt gttatctggg   9840
cagagaacaa actagtgcta gttcaacatt tataaataac tatatgtgta taaaagtgca   9900
aaataatatg ctattaaaaa ttcagtaaaa ggagagtttc atccaacaga ctcatgacac   9960
attttttggg tgggagaata tagaggagct tatctcatta acacacaaaa caagaacaag   10020
tacatcagca gcaataatta tattattttc aaaaaacaaa acatggctac tcttcttaag   10080
gaggttaatt cacaagacat ggaagagaac acagctaatc agtccaactg agtagttcca   10140
tagtaaccat aagaatgttt tctatacata gaaggtgata aatttgaggg aaggagaaag   10200
aaagtctcaa tgaattatta atgtcaacat gactggtaga gcagatttag ttactcattc   10260
attcagtgtg gactagatgc tttgcagaca ttactgtgtt taagtcttgg ggagaccata   10320
atactaatag ttatgaagtg cttgttatgt tctcagtgct ttccatgtgt taactaattt   10380
aatccttaca acagcccttg agaaagacac tcttactacc tccgtttcac aacagaagaa   10440
tctgaggccc agggttatcc agtttataag tgaccgagcc agaatctttg tccatgctct   10500
ctaccccact ctcctacctc ccaaggacaa tctctgtgat agtttattca atcagcaaac   10560
atttatttag ggcctgatat gtacaagtta ctatgaaaaa cccatttgtg taggtgatgt   10620
tgggtttggg tgtggataga atgatggacc aagtacagat cttttttcaa gaagcttaca   10680
ttttggtgag tgttaaagat tggtggtgaa taatgcaagt tacagttttta aaagtaggaa   10740 gagtgacttc ctgtttgtta gatgtctgct tatcatctaa caaatagact ggttgtaaaa   10800
caagctcaga acaaaaaga tgtaaatggt gttctggaag tagtaaagaa gcaatttgg   10860 cctgtgtaga agtttcagca agttatccag aaggtctagc taagatgatt ggtaaaagtg   10920
gctacactaa acaacagatt tcaatgtaga tgaaacatcc ttctactgga acaggcgac   10980 atctagaact ttcatagcta aagaagagaa gtcaatgcct ggcttcaaag cttaaggga   11040 caaactaact ctcttgttag ggacaaatgc agctggtgac tttaagtttt agcaaaatat   11100
tactgctcat tgacaatgca aaactagtca cccaagagtg ctgatggata ttaatgtttt   11160
cataactgct aatataacat ctgtttttca gcccgtgaat caaagagtag tttcaacctt   11220
caagccttat tttttaagcc atgtattttt gaggctatgg ctgccagaga taatgattca   11280
tctaatagat ctgggcaaag aattgaaacc ttgtgaacag cattcattgt tctgtagtag   11340
atgtccttaa aaacatttgt gattcatggg aggaggtcaa aatatccaca ttaacaggag   11400
ttcggaagaa gttgattcca actgtcatag atgactttga ggggttcaag acttcaatag   11460
agaaagtaaa tgcagatatg gtagaaatag caagagaatt agaattagaa gtggagcctg   11520
aagatgtgac tgaaatgctg aaatctcagg ataaactgg aatggatgat gagttgcttc   11580
tcaggcatga gcaaagaaag tggtttcttg aaatgatttt actttgagta aagatgctgt   11640
```

```
gaacattgct gaaatgacaa gaaaaaattt aggatattac acaaaattag ttgttaaagc    11700
aatggaagga tttgagagga ttgcctctaa ttttaaaaga agttctactg tggataaaat    11760
gctttcaaac agtatcacat gctacagagg aatcttttat gaaagaaaga gttaatctat    11820
gtggcaaact tcattgttgc ctcattttaa aaattactac agccacccaa ccttcagcaa    11880
ccaccactct gatcagtcag catccactaa cgttgaagca aggccctcca ccagcaaaaa    11940
agtttacaac accctgaagg ctcagatgat tgttagcatt tttcagcaaa aaattctttt    12000
taaattaaaa tgtatacatt gttattttag acataagact attgtacaca taatagacta    12060
cagtatagtg taaacataac ttttatatgc tgggaaacca aacaaaattg tatgactcac    12120
tgtattgtga tacttgcttt actgcagtgg aaccaaaccc acagtatctc tgaggtatgc    12180
ctgcaataaa ttatgcaatc attatcacta tctaattcta gaatattttc atcattgcca    12240
aaagaaatat tctacccatt agcagtaact ctttattccc catcactagc ctctggcagc    12300
cactattctg cattctgctt tctgtctcta ggaatttgcc tattctggac atttcacatc    12360
tgtcttgtat ataattcata tggatgatat gcagcttttt gtattgatct tgtttgcctt    12420
agtataatgt ttttaaaatt aatccatatg ataacaggag ttagtatttc atttctcttc    12480
atggctcaat aaaattctgt tgtatggata tgccacattt tgtttatcca ttcatcaatt    12540
tctggacatt tgggttttcc attgtttggc tatgcaagtt tttatacaat tgtcttgata    12600
tgttcctagt agtcaaattg ttggattata tggtcactct gttaaacttt tgagaaact    12660 gcaaactgtt tctaaagagg ctgcaccatt tgcgtttcta tcagcagtta aggctctgat    12720
ttttctactt tctcaccaaa gcttgttatc atctaacttt ttattctagc tatctctgtg    12780
ggtgtgaagt agtatctcat agtgatactg attggcattt ccttgatgac taatgatgtc    12840
aagcatcttt tcattattgg ctgttattat cagccatttt atatatcttc ttttggagaa    12900
ttgtttattc aaatctttca cccactttta aattggatta tttgtctttt cattttata    12960 gttgtaagag ttcttatat gctctggatc ttagaccttt atcagatatt atatttttc    13020 ctcccatcat ttgtattgtt ttttattttc ttgatagtgt cctttgaagg acatttttaa    13080
cttttatgaa gtccaattca tttactcttg ttgcccatgt ttttgttttc atatcaaaga    13140
aactattgct taatccaaga caacaaagat ttacatctat gttttattct aagagcttta    13200
tagtttcagt ctcacatgtt ggtctttgat tcatattgag ttaatttatg tacgtggtgt    13260
gaggtagggg tccaacttca ttcttttttca tgtggctata cagttgttcc tgcatctgat    13320
attgaaaatt atattttccc tcattgaatg tctggacacc cttgttgaaa ataaattgaa    13380
ctcaaatgta tgggtttatt tctgacctct ccatggtaat ccattgatat ataatcccta    13440
tgccaggacc agacagtctc aattactgta gcttggtgtt tagttttgaa atcagttttg    13500
tctttcaatt atgtttttat tttcttaaaa tcatttatac tgatgaaatt gctgatattt    13560
attttatgga ttgactacct tttttaggg attagtatat taaatagctt tataatttaa    13620
atgcaatcta aatctctctg gtgatgtcat atctctgagc aattactaaa ccatgtgact    13680
ccatatacta gtaagtatgg tccagtgagt ggcatggaca gaagtaatga cagactgtag    13740
agaagtggtg gggagcttaa gagtattctc ttccttatag ctctcaagat ccgttttcat    13800
tctcccatta gattttgatg atatgctcat catttggtaa gagcacatga taatatatta    13860
agtataatgt tattgattta tttagagaca gagtctcact ccatcaccca ggctggagtg    13920
cactggtgtg ttcttagctc attgaaatct ccacctccca ggttcaagca attcttgtgc    13980
```

```
ttctgcctac caagtagcta ggattacagg catgtgccac cacacccagc taattttttgt    14040 atttttagta gagatgggtt tttgccatgt tggccaggct gttctcaaac tcctgacctc    14100
aagtgatctg cctgcttcag cctctcgaag tgctgggatt acaggcatga gtcactgtgc    14160
ttggcctaag tataactctg taattgtcct atctgtttaa aacatctttc cattcataat    14220
tcccttattt tcttacttt gatatataat tttatttta tgtagtgaca tctatataat    14280
aaaatttcag atggttcaat ttgggcacca aggtgggagg gatcagggac tggtgtgaaa    14340
ttgatacaga aatagttttc ctataaagcc acaaataagt gatacttgga gaagaaagaa    14400
cttgtctttc ccccttgaat aatcttggca tcctcatcaa acatcacttc accagagatg    14460
tatgggttta tttctggact ctccaattcc attttgttca tctgtatatc tgtcctgggt    14520
cagtaccaaa ctgtctttat tactcttct ttggataagt ttgaaatcgg gaaatatgaa    14580
tcattttact tttttttttt ttgagattgt tttggttcat gcataaacta atttgggacc    14640
atcattttcg taataatgtt taaaaatgct tgtggtccat gaacatggga ttttttgttcc    14700 atttatttgt atcttttaaa ttttctttta acaatatttt atagttttca gaatataggt    14760
tttacccttc ttttgttaaa tttattccta agtatcttat gtctctttaa tgctattgca    14820
aatggaattt tttcttttatt ttaaaattat ctatgatttc taactctcca ctccttgtat    14880
acttacctaa gtatgtgtct tatttccccg tactagtcca tatgtatatt aaggacagat    14940
tttatgtttg agtcatcttt gtatctcaca gactattagc ccagcatctt acacgtagta    15000 gttttttcaaa tgtttaatta ataatttatg gattgttaat caacaccata aattaatgaa    15060
aacccagagc taattttgaa taatctagga agcctgtttt tttaacatat gttctttgga    15120
aatttgttat gaattaaata tcaggtactt tttgatatca atatgaacta gttttggatg    15180
ttatacaata tttttatcc ataaaaaatt atttacccta aatataactc acatggttga    15240
actacataac tcttagtcac cacagcaaag gctgtttcaa aatataaagg ctgctagaaa    15300
tggccaaacg ctttctagga ataactcagt ctaattgtag gcaaatacag ggctatccct    15360
ttattttaag ttgtaaactt ataaatctaa tgactaatcg gttataatat actttcacaa    15420
cttccaatat ctttaactgt gactctattc cagaggcttt cacagattca acttctgtct    15480
ttgcactgac agctctcata tagcctgagg tctacatttc tcccattaac tctaggacca    15540
tttaattcaa atatctagta gatatctcta cccagatgta ctatggcacc tcatgcataa    15600
tagtcaacta attgccatca catttagcct gttcctgctt ctgtattctc tatcttaggt    15660
aattttagca ttttcctagt cttcaattc tgaaagccta gaatcatctt tgatggcctt    15720
catctcatcc atcaccaaat tctatagttt aatatatcat cttaacacct gtattatcca    15780
tctattctat agacttctac tactagtctt agttcaagta gttgtcagat ctcaccggga    15840
ccacttctgc agctgtcagt gggccctgac taaccttcct gcctcccctg tgcatctggc    15900 cttttaatg atgcttgagt tatctgtccc gattcaaatc tgttaccatt ttcttctttt    15960
ttaaaaactc tttaatgaag tatctctccc ccagcaccta tcaggatttg gtcttgcatt    16020
tgattggttt gctaacagaa gtagccaaag aaggatcaaa ttctagccaa atattgcttc    16080
aaaaatatgt gtaaataaat ggacaatgtt taaataattg tagttaacaa ataaggaaaa    16140
tgtaaattga ttacaataaa aattagtttt ttaatatcaa tttatgctag agtaaaatat    16200
aaatttcctg tttatatgac tcagtagcat gactaatcag ttgcaattta acaagagaca    16260 ttgctttta agaggcaagg cttttgtgtt tatgaataac tttttctag ttataaaat    16320 taaagaaaaa tagactaatt aaaagataga gactgcctga gtagatttta aaaccctac    16380
```

```
tttacgttgc ctaaaagaaa cctactttaa atataaagat acatatagat tgaaagtaaa    16440
aggatgggga atgatacact atgttaacac taatcaaaat gggagtagct atattcattt    16500
cagtcaaagt caacttcaga gcaaggcgga ctatcatgga tataaagagg gtgcattaca    16560
taataataaa gggccaatta tccaagaaga cataagaatc cttgctctgt acatatctaa    16620
aaacagcatc aaactctgtg aagcaaaaac tgataaactg caagaaatac atgtatctat    16680
tattatagtt ggaaacttca cagccttctg tcagtaattg acagattcag cagggaggaa    16740
atcagtaagg ttacagatga acttgaaagc accataaatc aactggatct aattgacagt    16800
tataaaatac ttcatcaaac aacagcataa tacacatttt tctcagactc acatggaata    16860
ttccccaaaa ttgaacatgt actgagccgt aaaacacacc ttaacaaatt tttataaagt    16920
acaagtcatg cacaacatgc tctcaaccaa aatgtaattg aagtagaaat caataaaata    16980
agaaaaatag gtggaaaatt cccaaatatt tggaaattaa aaacacaatt tttgataaca    17040
tatgggtcaa acaaaatgtc tcaaaagaaa ttttaaaata ttttgaatta aatgaaaaga    17100
aaatagatat ttgcatgata cagtgagagc agtgcttagg gtattaaatg catagaaaga    17160
aaagaaaaag atataaaatc aatagtctaa tcttccacct taggaaaaca gaaatgagaa    17220
agaaaattaa aactaaatta atcagaagaa aataaataat gaaattagag atgaaattga    17280
gaacaagaaa ttagtagagg aaaatcaatg aaaccaaaac tggttctttg aaaagatcaa    17340
taaaattaat aagcctccag ccaggctgac cacgaaaata agaaacaaga cacaaactac    17400
tactatcaga agtgaaaaga gagccatcac tactgattcc atggatatta taagataat    17460 gaggtaaaag tattttgatg gttaattta tgcattaact tatcttggcc aaggaacacc    17520
aaggattgcc agcagccacc aaaatctagg agaaagtcat gaagtggttt caccacagag    17580
cctccaaaag gaaccaaccc tgccaacact ttgatgtcag acttatggct tccagaactc    17640
tgagagacta aatttctgtt gtttttaagcc accctgttca tggacatttg ttatagaagc    17700
cctaggaaac tcaaataaat ggtgacaaaa gtggacaaca tcctgaaaaa aaattcacta    17760
acactccact ttgaagagag gccgtggaaa tgtctactgg ggaaaagcaa gtgaattggg    17820
gaaatgaccc ctaaatatgg tagtctctat gaaaagcaaa acacctcttt ctcagttggg    17880
aggaaacttg aagaccaaat gagcactctt cctcatgca ggccagctca ccatacacca    17940
tgatgcactt taacaaaagg taaattgtta aaaagagagc acagtgttaa taacagggaa    18000
ggctatgcat gtgtggggac agagagtatc tgtgggaaaa aaaacagttt tcttattctc    18060
tccctcaaca acaatcaaca taggagactt ctatgaccaa atgtgtgaga gtttttttcc    18120
tcatattcta agcaaagaat caattctgca aaggacacaa gctggctgtc aattcaatta    18180
tgacactatc tatctgaaga cagcaccaca tagcacaggt tgaggctgtc ttcatgactc    18240
ctccttcccc ctccacccc atttcagatg ccaatcacaa accctaggat gtctaacctg    18300
tgcttctgac caactggctg tacaatgggg atcccacaac ctgctccttg ggtttaacta    18360
atttgctaga gcagctctca gaacttgggg aaatactaat atttatcatt tcttataaag    18420
gatattacaa aggtacagat gaagagattc atgggcaaga tatgggagaa caggtctgga    18480
gctttcttgc cttctctggg catgccaccc tccaaatacc tccacatgtt cagctatttg    18540
taagctctct ggagagttag gcatgactga ttaaatcatt ggccattggt gatcaacata    18600
accttcagcc cctctcctct ccccagaagc tgggggatgg ggccgaaagt cccaaccctc    18660
tatttatgcc ttgttatcct aggggctggg actggggctg gagctggggg ctgcctaggg    18720
```

```
gctgccagat accagtcatc tcattagcac agaaaaagac attcctttgg aggtttcaag   18780
gattttatgg gttgtgtgtc aggaatctgg gacaaagacc aaacatacag tcatacgaca   18840
caatgtttca gtcaatgagg gactgcatat accatgatgg ccccataaga ttataatgga   18900
gttgcaatat tcatattgcc tagtgacatc atatctgtgg taatgtctta gaatgcatta   18960
ctcacatgtt tgtgatgata ctgatgtaaa caaacccatt gcactgccag tcatataaag   19020
gtatagcaca gtagtgttca gtaatgtcct aggccttcac attcactcat ggctcactca   19080
ctgactcatc cagagcaact tgcagttctg caagctccat tcatggaagg tgccctatac   19140
aagtgtacta ttttttaatat tttataccat attttttactg tacctgttct atatttagat   19200
atgtttagac acacaaatac ttaccattgt gttattatta tctatttagt gcatgctatg   19260
caggtttgta gcctgagagc aatagactat accttatagc ctaggtatgt aataggctat   19320
accatttagg tttgggttct atgatgtttg tgcgatgatg aaatcatcta atggcaccat   19380
tacaatgaca catttctcat aatatatccc ctatcattaa gtgacacata actgtatttc   19440
acagtatcac aatgtacatg aggaatctct ataccttctt ctcattttttt tgtggaccta   19500 aaattgctct ataaaatagt ctttaataaa aagagagaaa gaggacagtc cctgtccacc   19560
aacaaaattg accacaggtt ttcccacttc tcagtgcact accattgcca catcccctt   19620 cgcatatagc tgtgttccca ggcttttccaa gagcacacag agcagataat actgtggctt   19680
cacttagaaa ttcaacagag aagtgactgt gataagtgag aagaggatca tgagatatgg   19740
agtcaaataa atatcagcac agagtggtcc actttaaatt taagatgaaa ataacataca   19800
acgatacaga aatgccacag caaaataaaa agactaaaag aaacctagaa tataagcatc   19860
cattctggaa gggggcagac acgaagaaac agaataaaaa ctttcatttg tacttcacgc   19920 catagttttta aagtacacat gaattttaca acagaatatc aaagagtagt tgataaaaga   19980
atagaatgag atgaaaaaat attatacaac caaggaaata cattgaaatc caaaattatg   20040
cactccctcc attttagatg tgacaaaagt gttagcaaca acaagaagaa tgaacaaaaa   20100
atatgaaata gatttgttat aatcaccata aatgcacagt aaaaatacaa ataccaaaca   20160
gttgctgaaa caataaaaga taagaagaga tgatagtgat ccattttatg aataattgtt   20220
cctaccaaag aaaattcatc gaatggaaga ataaaacaac ctatgataga ggaaattttt   20280
tccacaaatt gaggcaaaat ggaatgaaca gtgctaggta gtatatcatg tactataaaa   20340
attgattcaa catgattgtt actaagttat atcttggaaa agtgactgaa tttcaagagc   20400
aaggaagaat aattctaaag gtggaaatgg caagtcagtt ggaggagaat cagagtggct   20460
tcagattttt cacatctaaa tgcaaaagat aatggaataa tgtctacaaa attctgagag   20520
ataaaaatgt ggctcagaat ttgataccta gacaagatgt tgttcaaata taagtgcac   20580 aggcagaaat ttatgtatgt cagaatttag gcaatagaac actcatgagc cttttcaagg   20640
agaagatgga gggggagggg agctactgga tataaaatcc aaccaaccaa gagaaaagtg   20700
aagacactgt agtaaaaggt caattgatag cacaaaattc acttccttgt agaattagag   20760
tagcctcttc aaaatatatt atattctttt attttcctca tggttcttgc tactgtctca   20820
aattatcata ttttttaggac agagactctc tgtcttgata atccttgtat ccccaccatc   20880
tagaatgtta cctggtacag acaagaccct tcataaatat ttattgactg actgagtgaa   20940
tgaacatagt ttcacattaaa aaaaacttaa atgttatttt aaagttataa aattacagtg   21000
tagcataaaa ttatatgtta tatcgtgtat atagtataat tcaaaattat gttgtaaaga   21060
tgttgatata cataagtgac tgtgttagac acttctggct gccatatcaa agaaccatgg   21120
```

```
actttggtac tttggtggct tataaacaag agaaatttat tcctcacagt tctggaggct  21180
ggaagtccag gattggggtg gcatatggtt gggttctggt gaaggacctc ttccaggttg  21240
tggactacca gcttctcata tcttcacgtg gcagaatgtg aaattttcag atggctagag  21300
agctctctgg tgtttctttta taaggcacta ccaccattca ttagaggttc accttcatga  21360
cttaattacc tcccgaaggc ctcactttct aacgacaaca cattgggggt taggatttca  21420
acatatgaat ttcgaggaga cacaaatgtt cagttcataa cagtgacatt ttaaaatcat  21480
tatatgactt atagtcttca ccatattggc tctatcagtg acttctcact attggtttat  21540
gtgctactca tatatttact tgcagtttac ctaatggctc gcttattttt gcttaaccag  21600
gtggtgttta gagttatgct ctcaaaacag aacactctct tctgacagtt tggtttatca  21660
tacttggctg ctttgcttta catatttctt taataaatct ttatctttga tctgcctgtt  21720
accaccccac ttcagctcac tagaatcttc gaatatatcc atctcatact tcatctctca  21780
aattgtctca ttaatcacag gttatatagt tgaaattgat atttaaagtt caagtaaata  21840
gttataaagt acagcatata agcatttgtg attataaatt tacagttgcc acatatgtta  21900
attggtaatt agatcgctgc ttgtaggatg gtatataacc attactgcat attaaccttta  21960 agactaatga gtgagagctg ggccatgatg gctgactaga cacagttgca gttggaggcc  22020
tccaccgaga ataacaaaaa cagcaagtga atcctgtgct ggcaactaag gtatccaggt  22080
tctctcattt ggactgacta ggtggttggt gcaactgaca gaaagcaaag aaatcagagt  22140
ggagtaatgg cccaccctgca gggggtaagt gggactccca tccccagcca agggaggcag  22200
tgagtgattg gccatcctgc ccaggaaacc atatttttcc gtggatgggt gcaacctgca  22260
aatcaggaga ttcccatcat aagcccacac caaaagggcc ttgggttcca agcacagagc  22320
agtgcatatt ctctcagtgg ccactgggct ggggtctgcc taagactaca gagttcctag  22380
agggaagggt agccaccatc gctatggcta cctgctgcct aagatgactg aacttagaaa  22440
aggggcagca accatcactg cagctccagt ctgccttttc ccctgctggt gccagagata  22500
ttgggtggtt cagatccagg aggaattctc cacagtgcaa cacagcagct gtggcagata  22560
atcaccagac tgcctcttta ggctgcaccc ggacccatcc atcttcactg catgtggcct  22620
ccctctggga atttcatcat ctccagccag gggtttacgg acagagctct gatacccctg  22680
ggatggagct tctgggggga ggagcggctg ttgtctctgt ggatcagcag acttagtctt  22740
ttccccgctg gctctgagga atccaggcag ttcagacgag tgggattcca gccagagtgc  22800
ttcattaagt gggtctttga tcctgttctc ctgactgggt gagaccaccc caacaggggg  22860
tcaccagata cccttatatag agacattccc actaacatga agtcaataac cctctgggat  22920
ggagctccca gaggaaggag cagtaagcca tctttgctgt tgcgcagcct ccactggtga  22980
cacccccagg ggtgggagag acccaggcaa atagggtctg gagtgaaccc ccagcaactg  23040
acaggagcct tatggaagag gggcctgact gttaaaagaa aagcaaacag aaagcaacaa  23100
caacaacagc atcaacaaaa aggcacccac agaaaccccca tccaaaggtc agcagcctca  23160
aagatcaaag gtagataacc tcagcaagat gagaaacagt caatgaaaaa acactgacaa  23220
ctcaaaagcc agagtacctc ttcttgaaat gatcgcaaca cctttccaac aaggcacaga  23280
actgggctga ggctgagatg gataaactgg cagaagtagg cttcagaagg tgggtaataa  23340
tgaacttcac tgagccaaag gagcatgtcc taacccaatg caaagaagtt aagaaccatg  23400
ataaaacatt atagaagctg ttaaccagaa taatgtttag agagaaacat aaatgacctg  23460
```

```
atggagctga aaaatacaac acaagaactt cccaatgcaa ccacaggtat caatagctga    23520
atagatcaag tggaggaaag cacttcagaa cttgaggact atcttgctga aataagacac    23580
aaaattagag aaaaaaggca tgaaaagaaa tgaacagaac ctgtgagaac tatgggatta    23640
tgtaaaccca caaacctac gcctgattgg ggtacgtgaa agagatgggg agaattgaac    23700
taacttggaa aacatgcttt aggatatcat ccaggagaac ttcctcaacc tagcaagaca    23760
gggcaacagt caaattcagg aagtacagag agccccagta agatacgcca tgagaagaac    23820
cactccaaga cacatgatca tcagattctc caaggttgaa atgaaggaaa aaatattaa     23880 gggcagccag agagaaaggc caggtcacct caagggaaaa gcccatcgga ataacagcaa    23940
acctctcagc agaaacccta caagccagaa gagattgggg gccaatattc aacactctta    24000
aaagaaaaat gtttctaacc agaatttcat atccagtgaa actaagcttc ataagcaaag    24060
gagaaataaa atcctttcca gacaggcaaa tgctgaggaa atttgtcatc accaggcctg    24120
ccatgcaaga gttactgaag gaagcactaa atatggaaag gaaaaatgat taccagccac    24180
tacaaaaaca cactgaagta cacagaccaa tgatactatg aagcaactac atcaacaagt    24240
ctgtaaaata accagctagc atcatggtga caagatcaac tgcacacata ggaatattaa    24300
ccttaaatgt aaatggccta aatgccccaa ttaaaaggca cagagtggca agctggataa    24360
agagtcaagg tccactagtg agctgtattt aagagacaca tctcatgtac aaagacacat    24420
ataggctcaa aatagtaaaa tctaccgagc aaatggaaaa cagaaaaaat caggggttgc    24480
aatcctagtt tctgacaaaa cagactttaa accaataaag atcaaaaaag ataaaggcat    24540
tacataattg taaagggttc aattcaacaa gaagagctaa catcctaaat atatatgcac    24600
ccaatacagg agcacctaga ttcataaaac atattcttag agacatacaa agagacttag    24660
actcccacag aataatagtg agagaattta acactgcact gtcaatatta gacagatcat    24720
tgaggcagaa aattaacaag gatattcagg aattgaactc agctctggat caagtggacc    24780
tgatagatat ctacagaact ctccacccca aaataacaga atatacattc ttcttggcac    24840
cacatggcac ttactgtaaa atcaaccaca taattggatg taaaacactc ctcagcaaat    24900 gccaagaac tgaaatcaca acaaacagtc tcttagacca cagtgcaatc aaattagaac    24960
tcaattttaa ggaactcact caaaagcata caattacatg gaaattgaac aacccgatcc    25020
tgaatgactc ctcggtaaat aatgaactta aggcacaagt caggaagttc tttgaaatca    25080
atgaaaacaa agaggcagtg tgccagaatc tctggaatgc agctacagca gtgttaagcg    25140
agaaatttat aaaactaaat gtccacatta aaaagctaga aagatctcta gtcaacatcc    25200
taacatcaca atgaaaagaa ctagagaacc aagggcaaac aaaccacaaa gctagcagaa    25260
gacaagaaat aaccaagatc agaaaagaat tgaagcagat gtagacataa aaacccttc     25320 aaaatattaa tgaatccaga agctggtttt tgaaaaaaat taataaaaca gactgctagt    25380
tagactaata aagaagaaaa gggagaagaa tcaaatatac acaataaaac gataagataa    25440
atatcatcac tgaccccaca gaaatacaaa caaccatcag agaataccat aaacacctct    25500
atgcaaataa attagaaaat ctagaagaaa tggataaatt cctggacaga tatatactcc    25560
caagactgaa ccaggaagaa gttgaatcct tgaataggcg aataacaagt tctgaaattg    25620
aggcagtaat aaatagcctg ccaaccaaga aaaccgcgca ccagacagat ttagagctga    25680
attctaccag aggtacaaag aggagctggt accatttttt ctgaaattat tccaaacaat    25740
tgaaaaggag ggactcctca ctaactcatt ttatgaagcc agcatcattc tcacaccaaa    25800
acctggcaga gatactacaa aaaagaaaa cttcaggcca acatctctga tgaacgtcaa    25860
```

```
tacaaaaatc ttcggtaaaa tactgccaaa ccaaatccag gagcacatcg aaaagcttat    25920
ccaccatgat caagttggct tcatctctgg gatgtaaggc tggtgcaaca tacaaaaatc    25980
aataaatgta attcatcaca taaactgaac taaagacaaa aaccacttga ttatctcaat    26040
agatgtagaa aaggcctttg ataaaattca acatccccc atgttaaaaa ctctcaataa     26100
actagatatt gatggaacat acctcaaaat aacaagagcc atttatgaca aacccacagc    26160
caatatcata ctgaatggac aaaagctgga agcattcctc tagaaaacta gcacaagaca    26220
aggatgccca ctctcaccac tcctgttcaa catagtattg gaagttctgg ccagggcaat    26280
caggcaaaag aaacaaataa aggtaggcaa ataggaagac aggaagtcaa actgtttgcc    26340
gatgatgtga ttttatatct agaaaacccc attgtctcag cccaaaagct tcttaagctg    26400
ataagcaact tcagcaaaat ctcagaatac aaaatcaatg tgcaaaaatc acaagcattc    26460
ctatacacca acaatacaca aggagaaagc aaaatcatga atgaactccc atttacaatt    26520
gctaaaaaga ggataaaata cttaggaata cagctaacaa gggcaagtga agacctctca    26580
gggagaaata caaaccactg ctcaagtata tcagagagga cacaaacaaa tgaaaaaaca    26640
tgtcatgctc atggatagga agaatcaaca ttgtgaaaat ggccatactg cccaaagtaa    26700
tttatagatc caatgctact cccattaaat taccattaac attcttccca gaattagaaa    26760
aaactaccat aaaattcata tggacccaga aaagagccag tattgtcaag acaatcctaa    26820 gcaaaagaa caaagctgga ggcaccatgc tacccaactt caaactacat tctacaaggc    26880
tacagcaacc aaaatagcac agtactcata caaaaacaga cacgtagtcc aatggaaaag    26940
aatagagacc tcacaaagaa gaccacatat ctacagccat ccgatctttg acaaacctga    27000
caaaaacaag caatgggaa aggattccct atttaataaa tgtttcctta atattccatt     27060
attttaaaca tttattaagc atctgctaat agtaatctgt caactcaaat ctgaatgatg    27120
tattcccctc ttcaagaact ctagtgactc agagtggaat aacaatttta atgggacttt    27180
gaagaatgta tagttcttaa ggaggcaaaa atgaaaggga atgccatttc atcagagagg    27240
actatttgag tcaaagcttc gaatcctgcc tttccatgca atttgcatg catttatgaa     27300 atggctgtta aagattgtgt gcaagctgtt aaataatgag cacaggtata aaaaagacca    27360
gtttaccaga ctatgaggtt tagttttgaa agagagctag actcttaaat aaagaattgc    27420
aatgcaatgg gataatgctg ataattacag ttgaaaatgt ttagggatac caactaattt    27480
gacctggggg cttggtaatt agatttaagt caatggcccc atgtagctct agaggagatt    27540
tggatgtaga aaagttggaa ggtagggtat ggctagattt tgcaagacct tacataccag    27600
gccgaagaat gtgaacttga tctttaggac tatataataa ggagcgatca ggcttttaaa    27660
ctgcagcagt gtagaattaa atctgggatt tagaaagata attcatatgc gccatataaa    27720
ataaatttgt gatgaaaagc attcagaaag ataggttatt tcagcattcg tagttggcac    27780
tgttgagtat ggcatgtttc ttttttaaaaa ccatagtaaa atttacagat ggcagctgat    27840
gtcctctgaa agtttgggag tatgtgattg atgatattgt cattcaatca gtaattttta    27900
ttacatgaaa atacaatgga aaactcaaag attgataaaa tatagttctt gcattaggaa    27960
caagcaaata aaaggcagta gtgaatgcat ggagtcctta aggtagttt cccaaaagga     28020 agagtaaaac tgaaatggcc cccagcacct ggagagaaaa aggagaaact gcaagttgga    28080
gcaatgagat gaatgctaat gccacaacat aattacaaag tccgtcctag tgaagaagga    28140
aggcactttc agattgccct ttttttatagg tgcctgttgt tgtcaaggcc tgttctcata    28200
```

```
cctggccaga cttccattaa gtctgtgcat tcaactttga ggacaatgat gcgtctaata    28260
ctcccaggcc tgaatagcta ttttatgaaa attactatat tggtattttt atttgttttg    28320
aacccacatc tatgcctgca ttagatatta taaactttat tatctagctt ctttaccatg    28380
tgcagataga ggtgaatctc aactagacaa ccgatgaaga cattgtcgat cacataatga    28440
taatatttgt gcttcagttg ttttttctctt aatggtgctt attatgcagg ttattaattc    28500
aaagaccatc attggtattg aggaatgtga gagtaggaat gtcatttata gagatgaaaa    28560
gtttctattc accatgaaga tcacagatgt tttcatctgc cagggagtaa tttatactgc    28620
atctacttat gttatgaccc gtgtggaccc tgtgtcaata ttgaatctga atatgccact    28680
tgctagctat gtgacattgg ataaattact taatccttct gtgccttagt ttccttattt    28740
ctaaagtggg gataaaatta ggacccatac ttcatagggt tattttaaat aaattaaatg    28800
ggctaatata tgtaaagctc atggaacagt gcctggaact taagcattca acaagtcata    28860
gttcttgtca tattattaat gttagaaata atgtctgcaa caatgctctc taaatttcct    28920
atctcacatc cttaagaaca gatgcaaata aaaacctgta atatttgaaa atggctagaa    28980
attgtgtgat ttatgagagc aaaattcaaa catacacaat atgattttgc attcacttta    29040 gtccctctt atccaacatt tcagcttctg tggtttcagt tacccaaaaa tcaatgaagg    29100
ttcaaaaatc ttctatggaa acttccagaa ataattcgta aattttaaat tgtgtgccgt    29160
tctgagtagc atgatgaaat cttgcactgt ctcactctat cccatccaag gggtgaatca    29220
tccctttgtc tagcagaacc gggctgtgga tgctacctgc ccattagtct catagtagcc    29280
ttttagatta tcagattggc tgcagaggta tctcagtgct tatgttcaag tcattcttac    29340
tttacttcat aatggcccca aaaagcaaga gtagtgatgc tagaatattg tcataattgc    29400
tctatttcat tattaggtat tgttattaat ctcttactgt gcctaattta taaattaaag    29460
ttttatcatt ggtatgtatg cataggaaga aaagtaccgc atatataggg tctggtacca    29520
tgtatggtct caggcatcca ctggtggcct tggaaagtat cctccaagga taaggggtac    29580
tactgtagag aatgtagaag tggctatta ataaccacta atatttatt tagcatggaa    29640 gtgtttgaag taaatcttta cacagaggtc cagtgaagtc ccaagccctg actatcctgt    29700
atcatcctta cgcttacttc taagcgcccc cccagttacc ttatgaaatc ctaggactac    29760
atggaatatg atctatgaaa accactgccc tagtccaatg tactcatttt gcttatgaga    29820
aaattcaagg agaggttaca gtaagtcagt aaaacgctac aggaagaaaa aggactggaa    29880
atgaaatgct ttggtcagag tccccacttt gcccctttgg ctatgagatg ttggacaatt    29940
cagttaactg cttgaaagcc tgattttttcc aattagaatt ttgattttca taatctctga    30000
gatccattcc tgctgtaaaa ctattcaatg tcagaaatgc acacagtcat ccacaaactc    30060
tagtttggtg ttcttttcat tgcactgatg tagaagtatc gactacttag gagaaccaaa    30120
gaatgaatgc cctggatgaa ttccataata accttttctgc catccagag taggatatgt    30180 ataattttgt gacgtatggc actgtaccaa gtacaggtga atatgccgtc aggttttcaa    30240
tagttatgca gtgtgtgtat ttaacatgaa cactgatagc taggcaaatc tgccaattgt    30300
tgaatcatat agttcctgga acaccatttc ttatccccaa acttatataa ccacacctgg    30360
attaaagtaa attaataaaa tactacgttg tgtacctaag gtgtgttggt aaagctggaa    30420
aaggcaactc atgaataaaa aatatatatt acctccagaa aaataaatgt aatgcataca    30480
caactttaca caagttaaag aatggggttta acaactaaga tttgttcatt acccttttcat    30540 gagacattct tttgttctgt attcattaca ttattagatt ttctagtgaa tttcaccaat    30600
```

```
tgattttctc taagttgagc ttcatcagag aaattctgta gaggtatttt cacaaatgaa   30660
aactcacaat cacaagtttt ctaactcttt tgcataaaaa agcactgagg acactttcat   30720
gatgatatta ttctgaaaca ccatatttaa gaatatagtc attttttattc tttgtttgtt   30780 ctttatgtcc taatgttctc tacagtggat tccatcaata ttaattgtta aaatattaac   30840
tttctatttc tgccattgtt ttatgtacca cagagacatg tattagaaaa cacgctatgt   30900
tatgggtgta agttaaatga gaagcacagt gccaataaat tgcacgagaa ttgctttact   30960
tgggctattc ttggtcatag gaaggactgg gaaattaata tagtcacgtt tttatagatg   31020
cagagctttt attaattaac atacagttgt taattagtag tatatgttca cctttgttat   31080
taacataaaa tttagtacaa aacacttttg ggatattaaa ttttggtatt aaatatgtcc   31140
tatttcatac atgttagaat ataattaata tatacttatt gtcatcacaa agaatcaatg   31200
ctaaagtcaa aaaattccag gtactttttt tccttcttgt taacctagca atgttgggca   31260
ttagatgaag aagaggcaag gctacagggt tagataagga tctgcagtct tagtctttgc   31320
aaatacttgg tatctcttgc cttctcaaaa cttaggcatt gaaaattatt ataagtaatg   31380
aaatccaaaa tgttagatag ggtaaacaca gttgaactca caaatatatg ttttttttttc   31440 ttttctctgc tcttttggta gaaaatgtag aacatgatta ataaggttgg agttttttct   31500
ttataatttt tttcacagtg gcgttccaaa ctaaagaatg cttgtttacc taatatggcc   31560
aaattggagc cagtaccttc attcagctag atttaccccca gttgcatatt tgcaatgagg   31620
cagaattcct acagacagcc ttccttctga ttttctgcc tttgttcctc ctcacactgt   31680
gtttctccca taattcacat ctaccctcta cctaattggc ttctccagtc aaagtggata   31740
agcatctcag tcagaaatac attatgagaa cttcccaaac atgtactaat cgccacaaac   31800
caaggctcag atcatgccat atcgctgctc aacaactttc cttaggttac cactcactgg   31860
ctattgcagg actaattcct tatgtgggca ttggagaagg aaaatctgtt ctttacattt   31920
ctagcctact tgccactctg tattgcccct tacacgccca gcaccacaac caaattggat   31980
tacttactgt ttccaaaata tgctccacat ttttgtacct cagtgccttt gctgttttct   32040
cattgtggaa ttttctactt ccctgtcttt gctccacaaa tcttcccgca cccaaattta   32100
aagacagcag gaattgaata acatccttttg ttcaataccg ttcgttatga cattgatgag   32160
aaaaaagtcc atttctggcc ctggaccact gtctgtgtag agttagcaca ttctccccgt   32220
gtctgtgtgg gttttctctg ggtactttgg tttcctccca catcccaaag acgtgcccac   32280
tgggtgaatg ggtatgtcga catggtccta gtctgagtgt aggtgtgtgt gaatgcaccc   32340
tgtgatcgag ggtgtcctat ccaggactgg tccgtgcttt gtaatctgag ctgctgagat   32400
agactccagc cacctgaact agaataagca gtttggaaag tgaccctgaa ctagaataag   32460
cagtttggaa aatgaacaaa tcaatcaatg taaattattg tcaaataaaa atttgttaag   32520
taaatggtca ttatacaaat acacaacaat aaatgatgca agacgaaggt gctcatccag   32580
ctgtgagtca gccttacttg tttgtgattc ttttttaact gtgtggtgga agtgctcctg   32640
acagttttag ctttgcaaac acttatttct tgacttaatc caccaccact atgaccatcg   32700
acactcactg atttacaaaa acatgggtaa ttatcttgtt tttgttaatc tttcttaaat   32760
gtatgtgtag ctcatatttta attcagtgtt taatattaga aatgtttggg gtcttcatttt   32820 agaaatttgg cgatgttttt gtgatgagaa atatgccaca ggatcttaac tctttttat    32880 atcaattaac ctacggtaaa attggtttct ttgtacaaca gtttacttaa agtcgcagtt   32940
```

```
tccaagaacc tatccgtgat gttagatgag gacttactgt gccatttaag gtcaagttca   33000
ggttctactt tattcataac gcaagtcaaa agtagtctta ctgttgcact ttatcttgaa   33060
cactattaag gaaggtatca ttctatattt tatgcataaa atctgaatat gcatatacat   33120
tcaatatttt ttttaaagta gacatgtaaa tgactaagca aacaaaatgt attacaggct   33180
atgtcatgtg gtcagggctt aggattcaga aaataatatg ttgtcttgaa ttttgctagc   33240
acttatattg tcaactcttc tattaaattc tgttgattga aaattttgaa tcaagctcac   33300
attacttata tgacaaattc gggtaataga aaaagcatgg gctttgtaac caggcaaacc   33360
agtatttgca tgctagccct gccaatcatt agttttttcca cttagtgttt ttgtgaatct   33420
ggtttctttg ggattgtgga gtgtaatgat agtgacagtt gttagatatt gcttgcactg   33480
tccattattc taggaagaaa gtttcctgga ataggaaata taactgattg ttttcccaca   33540
ggagaagaag gcacttcctc tcctctttgg ggctagaaat gacttacttt aaaaatctca   33600
gttaagagag gactaaagct gttccaatgt tatgattgta ttcccctaac tatgtgaagg   33660
tacagcagga gcaagccttt catttgtagc agtggctgca acagaaaggg gggcagtttt   33720
tagagcggcc tggcacaggg tattagtttt tgaatcctcc aggctgaaga atgtgtgctt   33780
cctcagcatg tgtaagtatt tgtgtcagta tgctttcatg tataattagt agaaaactga   33840
acataaatgg acttaaacat taaagagtta tttaatggcc tgtataactg aaaagacccc   33900
agttgaatgc tttcaactgt ggcttagaat ttcaacttaa tttctttgca attttttgac   33960
tctgcgtttc tccatgtggc attaatcttc atgttgtggc ttaccagtag ccaccagggt   34020
ttctttattc ttccatatcc agcagaatga taattccttt gcctataatt aactaagttc   34080
ttagatgtac tctgattgga ttatctatga aaaaatcctt atgtcagcgg aagacccagg   34140
tcttaactgc cttagacctt gtttaattga gcaagttgct ttggtcagag agatgggata   34200
acctttattt acttagtatc taagtcttag accaatcaaa actcaagcca gagctggaag   34260
tggtattaac tttcattaaa aaaattactg ctaaataatg gagagagaga aataggaatg   34320
atatgcaatg aaaaccacaa tgtctattgc gttgggaggt tttggagctc caacagccag   34380
gaaacagcta ggaaaacact ttctgacata ataagatctg tcccctctcc acaaatggag   34440
tgggaacatt agtgattccc actagagaag tagctttacc taggaaagtg gtgatttcat   34500
gaagttcgtc atttctatga cagcaagttg tggagaccaa ggagaagaac ctgaagagtt   34560
tattacagaa cacacattag ataacattat gggaattttc agaaattaca tggtgctttc   34620
agaggagttt atctccatca gataggaact taaaggctta aattataata atgtgtgtat   34680
aaaaaaagaa gagtgatttt attatataat cactggatag acaaaactgt aaagatctcc   34740
tataaagcaa aaggaaataa tttgtgtatc tgtctacata ctatcttcct acctatctca   34800
cttgtgtgcg tgtgcgtgtg tatgtgtgtg tgtgtgcgtg tctttgcata ttggtctgtg   34860
tatgcatatg tatatataat taagagaaga tgattgatac catagacaga gcagagagct   34920
aatctataaa taataagtgt ttctgaagag aaaatagccc atcaaaacag aagcaaaagt   34980
tcagaataaa agagagatat atttctgtat taaaatctta aacttgttga ttatgactca   35040
agggtaagag acaaacacta ggatatatca aggtgaattt tttcaaggaa gcatccttcc   35100
agtaagagag gggaaacatg tcgacaaaag gatacaatta ggttagcctc tattttttta   35160
ccaatgttta gctccaattg accaagctct actgaatttt gtgataacta ctaagttttg   35220
ttactgtggg ttcacagtct tagacccagg caaattttat tgaatgtacc aagaataata   35280
aagacacaga taggccagca agggtactgc ttctttattc aataaaaacc tgaccttaag   35340
```

```
attagtccat ttggcttttg ttgccactgc ttttggtgtt ttagacatga agctcttgcc    35400
catgcctatg tcctgaatgg taaagcctag gttttcttct agggttttta tggttttagg    35460
cctaacattt aagtctttaa tccatcttga attattttt gtatcaggtg taaggaaggg     35520
atccagtttc agctttctac atatggctag ccagttttcc cagcaccatt tattaaatag    35580
ggaatccttt ccccattgct tgttttctc aggtttgtca agatcagat tgttgtagat      35640 gtgtggcatt atttctgagg cctctgttct gttccattgg tctatatctc tgttttggta    35700
ccagtatcat gttgttttgg ttactgtagc cttgtagtat agtttgaagt caggtagtgt    35760
gatgcctcca gctttgttct tttggcttag gtttgacttg gcgatgtggg ctctttttg     35820 gttccatatg aacttaaaag tagtttttc caattctgtg aagaaagtca ttggtagctt     35880 gatgggatg gcattgaatc tataaattac ctgggcagt atggccattt tcatgatatt      35940
gattcttcct acccatgagc atggattgtt cttccatttg tttgtatcct ctttatttc     36000 attgagcagt gatttgtagt tctccttgaa gaggtccttc acgtcccttg taagttggat    36060
tcctaggtat tttattctct ttgaagcaat tgtgaatggg agttcactca tgatttggct    36120
ctctgtttgt ctgttattgg tgtataaaaa tgcttgtgat ttttgtacat tgattttgta    36180
tcctgagact ttgctgaagt tgcctatcag cttaaggaga ttttgggctg agacaatggg    36240
gttttctaga tatacaatca tgtcatctgc aaacagggac aatttgactt cctcttttcc    36300
taattgaata ccctttatt ccttctcctg cctaattgcc ctggcagaa cttccaacac      36360 tgtgttgaat aggagtggtg agagagggca tccctgtctt gtgccagttt tcaaagggaa    36420
tgcttccagt ttttgcccat tcagtatgat attggctgtg ggtttgtcat agatagctct    36480
tatgattttg agatacgtcc catcaatacc taagttattg agatttta gcatgaaggt      36540 tgttgaattt tgtcaaaggc ttttctgca tctattgaga taatcatgtg gttttgtct    36600 ttggttctgt ttatatgctg gattacattt attgatttgc gtatattgaa ccagccttgc    36660
atcccaggga tgaagcccac ttgatcaagg tggataagct tcttgacgtg ctgctggatt    36720
cggtttgcca gtgacaaatg ggatctaatt aaactaaaga gcttctgcac agcaaaagaa    36780
actaccatca gagtgaacag gcaacataca aaatgggaga aaattttcgc aacctactca    36840
tctgacaaag ggctaatatc cagaatctac aatgaactca aacaaattta caagaaaaaa    36900
acaaacaccc ccatcaaaaa gtgggcaaag gacatgaaca gacacttctc aaaagaagac    36960
atttatgcag ccaaaaaaca catgaaaaaa tgctcaccat cactggccat cagagaaatg    37020
caaatcaaaa ccacaatgag ataccatctc acaccagtta gaatggcaat cattaaaaag    37080
tcaggaaaca acaggtgctg gagaggatgt ggagaaatag gaacactttt acactgttgg    37140
tgggactgta aactagttca accattgtgg aagtcagtgt ggcgattcct cagggatcta    37200
gaactagaaa taccatttta cccagccatc ccattactgg gtatataccc aaagaactat    37260
aaatcatgct gctataaaga cacatgcaca cgtatgttta ttgtggcact attcacaata    37320
gcaaagactt ggaaccaacc caaatgtccg tcaatgatag actggattaa gaaaatgtgg    37380
cacatataca ccatggaata ctatgcagcc atacaaaagg atgagttcat gtcctttgta    37440
gggacgtgga tgaaattgga aatcatcatt ctcagtaaac tatcacaaga acaaaaagcc    37500
aaacaccgca tattctcact cataggtggg aattgaacaa tgagaacaca gggacacagg    37560
aaggggaaca tcacactctg gggactgttg tgaggtgggg ggaggggag ggatagcttt     37620 aggagatata ccaaatgcta aatgatgagt taatgggtgc agcacaccag catggcacat    37680
```

```
gtatacttat gtaactaacc tgcacattgt gcacatgtac cctaaaactt aaagtataat    37740
aataataaaa taaaaaagat tactccattt gaacaagata ttaataaata tcaataatag    37800
agaaatggtg atataaaaca atcactatta aatgctgcag tatttggtga tttctagata    37860
gctattgtaa atattaaaac acaaaaataa cttgtttcac ctaagcccta agaatataaa    37920
aagtgcgtgg ttatgggagg actgagaaag ctaaaaagat gataaatccc tcccttttcat   37980 tagaatgatt agtggatatg tatactaatt agattggtag agaatataat tttaataatt    38040
attggaaaac actcttaaaa gaattatagt ctttcaaatt acaagaaaaa aggaaaatac    38100
aatgtagtca cttaaatacc aaaattatac caaaattata aaataaagga aaaggaacaa    38160
aaagaaatag aatgactatc tgacaataaa tataaattat gttaaactcc aaaattaacc    38220
tgattgttca cactcacaca cacacactca cttgttcaca ctgtatgcac tatataagag    38280
ataaacacag acacacacac acactcactc acactgtatg cactatataa gagataaacc    38340
taaagtaaaa tatcaaaaat ttttttaatc ccttatataa aattatcaac tgatcattaa    38400
aagacaaaaa acttataaga aagtggataa gaacagacta ttcatagaaa agaagatgca    38460
aattgttaat taacatgaaa tgatgttcat cttcaagtag ttacaaaaat gcaaatgtaa    38520
gctataatga ggcataattt tttacttctc aggattggta aaaatggtaa agactgatga    38580
catctgatcc aaataagaat gtaacagaat ggcctccttt atatgctggt agaagcacaa    38640
attattttaa aaatacatat accatttttat tcagcaaatc tcacttttgg gaactaagtc    38700
tacagaaatg caagcattaa tataaaatga gataacaaac acatacagat acacatacaa    38760
agatgtctgt tacagaattg ttggtaggag caaatatttg actattcatc aataagtatt    38820
gaataatttg tggaacacac ttaatgtgga atattacgca gttataaaac aattgttcta    38880
gtatgtttga cctagaatga cagtcatgat ataaagtgag aatgtacaa aaatcaaagt     38940 gtaatgtata cactgtgatc ctattttta acaaaatgaa aaaggaaaat accctcataa     39000 aacccctatat atgcatgtat atatgtgtat tttctatgcc tgcagaccta acacgcatag   39060
gcataggatg ctgagctgaa agtatagagg tctcatatac tccttgtgcc cacagacaaa    39120
tttccccact atcaacagtt gctatcacag tggtacattt attatgatca atgactctac    39180
acatcattgt cacccaaagt ctatagttta gattaagatt cactcttggt gttgtacata    39240
ctatgggttt tgtcaaatgt cttcaatcca aattatatta cagaatagtt tcactctcct    39300
aacaacttca ctgttcattc tttgtgcctc tcctattcat ccacttgctc cctcttaaat    39360
cttgacaaac cacgaatctt tttactgtct ctagttttac ctttttccaga atgttacata   39420 gttgcactca aactgtatat agccttttttc agtttggctt ctttcactta ataatatgca   39480
tttaagatcc ttccatgttt tcttgttgct ttatagctca tttcatttta gaactgaaaa    39540
aatattccat tgtctggaag caccacagtt tacttattca ttcacctact gaaggacata    39600
ttcattcctt ccaagttttg gtcattatga ataaagctgc tataattatt cacatggggg    39660
ttttgtgtgg ccacaaattt tcaaattctt tgggtatata gcaaggattg ctgcattatg    39720
tcgtaagaga ttgtttagtt ttgtagaaga ccaccaaact gtctttcaaa gtggctgtac    39780
tgtttacctt cccatcagca atgaatgaga attcttttttg ctttcatcc ttgccagcat    39840 ttactgtggt cagtgttttg ggttttggcc attctaatag ggtgtcatgg tatctcattg    39900
ttgttttaat ttgcatttcc ctgatggcat atgctgttga ataacgtttc atatgcttat    39960
ttgctatctg tgtatcttct ttgctgaggt gcttattcag gttttttgcc aatttttat     40020 tgggttgtaa attgtcttat tttagatttt taagagttct gtataatatt ttggataata    40080
```

```
ttatttttacc agatatgtct tttgtaaata tttttttccag tctgtggctt gtaatctcat   40140
tctcctgatg ctgcttttg caaagcagaa gttctgaatt ttaatggagc tcagcttatc   40200
aatcacctct ttcatagatc atgcctttgg tattttattt aaaatgtcat ctcaatgccc   40260
aagttcatca agaatttctc ctatgtcatt ctctaagatt tttataatct tgcattttac   40320
attgaagtct atgatccatt ttgagctaat ttttgtgaaa ggttcaaggt ctgtgtctag   40380
attaatgtta ggggtgtgga tgtgaatgtc cagttgtctt agcaccatt gttgaaaaga   40440
gactgctcca ttttattgcc tttgcccgtt tgtcaaaaat caatggatta tacttaggtg   40500
agtcgatttc tcagctcata ttctggtcca ttgatctatt tgtctgtttt ttcactaatg   40560
ctatagtgtc ttgattactg taagtttatg gtaggttttg aaattgagtg gtgtcagtcc   40620
tctaactttg ctcttttctt tcaatattga atttactctc ctgggtcttt ttcctcttca   40680
cataaacttt agaaccaatt tgtcaatttc tacaaaataa cttcctggga ttctgattgg   40740
aattgcattg agtctgtcca ttcatttgga aagaactgac atcatgacaa tattgagtct   40800
ttctacccat gacctggaat atctctccat ttatttttt cttttttga tattatttat   40860
cagagttttg tagttttcct catatgtatt ttggacattt ttttttagat ttacacttaa   40920
gcattttatt tttagggctg ctaacataaa gtggcaatgg gttttaatt tcaaatttca   40980
cttgttcatt gatggtacat agaaaagtga ttgacttatt tctcttgtat cctgcaactt   41040
ttatataatt gcttattagt tatcagagac tttttacca atttaaaaaa attttctaca   41100
tagacaatta tatcatctgc aaacaaagac tgtattattt tgttcttacc aatctgtata   41160
cattttattt ccttttttgt cttactgcaa tagctaagtt ttgcagtaag atgttgaaag   41220
ctgaagtgaa gggagatagc ttttttttta ttatcaggaa acctacaaat ttcttattat   41280
taagtatgat attagctata ggacttttgt agatgtccett taagttgagg aagtccctct   41340
ctattcctaa tgtgttaaaa ttttttatca tgaatgggtg ttgaatgttg tcaaatgctt   41400
tttctgcatc tattgatatg attgtgtgat ttttcttcat tggcctattg atgtgatgga   41460
ttagattaaa caatattcca atgttaaaac cctttgcat acctgaaatt aaatccactc   41520
aattgtggtg tagatgataa gtgctatccc caatagcaaa ttgaatccaa taatgtataa   41580
aagtatacag ttttatgtgg aggatttttg aatctatgtt catgagaggt acttgtctat   41640
agttttattt tcttgcagtg tctttgattt ttgatattag ggtaatgctg gccttataga   41700
atgagttgag aagtattcct cctgctcctg cttacacaca ctgtcagata gtgtggagca   41760
ttgatacaat attgtcctta actatttgat agaattcagc aataaactca tctgggatta   41820
gtatttttg ttttgtaaca tcattttta tttattttct tgaatagata tagtcctatt   41880
cagagttttc atttctttt gtgtgagttt tggtagattg tgccttttga gtaattgatg   41940
catttcatat aggttatcaa atttgtggat ttagagttgc tcataatatt tgtttattat   42000
ctgtttaatg tctattggat ctaaagtgat gtctctgtat cattttata tgaacaattt   42060
tcacttaata ccaatctaaa tctacttcca aataacatta taccactttta taggaggtac   42120
aagtaattta tggtaataaa atattactaa tttctccctc ctaacctttt atcactgcta   42180
tcattcattt cacttataaa taaacatata agcataattg aatacatggt tgctatcatt   42240
atttgaaggt attaacttt atatcaatta agaataagaa aaacaggctg ggggcgtgaa   42300
gattaaccac cccatgtgcc atcactgca ccaacaaatg ctgtccaggg ggctgcatat   42360
tggccaattc tactcaccac tgacagtgct tgtgtgcagc atctggtggc atgaggacag   42420
```

-continued

```
gtgcacctca ccataatttt cactaacaac cagagcctaa gccaatgaag aactctcaga   42480
caatgctgac attgatcgca tccaaataga acatacagag acgacactac tgtgctagcc   42540
cagaattaaa gccaaaacat cttccccaaa caatactata attacagcta caggaaaagt   42600
ctttctctat gaaagaagcc aatccatgaa attaaaagag aaactgttaa aatagatgca   42660
cagataaggt aaggacatga gaaatatgaa aattcaagaa aaaaatgaca cctctgaagg   42720
aatacaaatac ttcttcagta aaatatccca aagaaatgta aatatgttaa aaagcctgaa   42780
aaagaattca aaataatgtt cttaagaaaa tgcagcgaga tacaagagga cacagataca   42840
aatacaagag gacacaatag aaaaaaaaaa atgcattggg aaggcaattc atgtcttcaa   42900
tgagaatttc aagaaagaga gacagatata aaaaagaacc cggcggcttc tagcccgccc   42960
gccccctcccc cgcgcgtcgg ccctgccgag ccggccggcc ggcctggctc ccctccccgg   43020
ccccgacggg cgggcggact gccctgagga ggcggggagg ggagggctgg accggccggc   43080
gggcgggcga cgatgccgaa cttctgcgct gccgccaact gcacgcggaa gagcacgcag   43140
tccgacttga cttggccttc ttcagcttcc cgcgggaccc tgccagatgc cagaagtggg   43200
tggagaactg taggagagca gacttagaag ataaaacacc tgatcagcta aataaacatt   43260
atcgattatg tgccaaacat tttgagacct ctatgatctg tagaactggt ccttatagga   43320
cagttcttcg agataatgca ataccaacaa tatttgatct taacagtcat ttgaacaacc   43380
cacatagtag acacagaaaa cgaataaaag aactgagtga agatgaaatc aggacactga   43440
aacagaaaaa aattgatgaa acttctgagc aggaacaaaa acataaagaa accaacaata   43500
gcaatgctca gaaccccagc gaagaagagg gtgaagggca agatgaggac atttttacctc   43560
taacccttga agagaaggaa aacaaagaat acctcaaata tctacttgaa atcttgattc   43620
tgatgggaag gcaaaacata cctctggacg gacatgaggc tgatgaaatc ccagaaggtc   43680
tctttactcc agataacttt caggcactac tggagtgtcg gataaattct ggtgaagagg   43740
ttctgagaaa gcggtttgag acaacagcag ttaacacgtt gttttgttca aaacacagc   43800
agaggcagat gctagagatc tgtgagagct gtattcgaga agaaactctc agggaagtga   43860
gagactcaca cgtctttttcc attatcactg acgatgtagt ggacatagca ggggaagagc   43920
acctacctgt gttggtgagg tttgttgatg aatctcataa cctaagagag gaatttatag   43980
gcttcctgcc ttatgaagct gatgcagaaa ttttggctgt gaaatttcac actatgataa   44040
ctgagaagtg gggattaaat atggagtatt gtcgtggcca ggcttacatt gtctctagtg   44100
gattttcttc caaaatgaaa gttgttgctt ctagactttt agagaaatat ccccaagcta   44160
tctacacact ctgctctttc tgtgccttaa atatgtggtt ggcaaaatca gtacctgtta   44220
tgggagtatc tgttgcatta ggaacaatcg aggaagtttg ttctttttc catcgatcac   44280
cacaactgct tttagaactt gacaacgtaa tttctgttct ttttcagaac agtaaagaaa   44340
ggggtaaaga actgaaggaa atctgccatt ctcagtggac agggaggcat gatgcttttg   44400
aaattttagt ggaactcctg caagcacttg ttttatgttt agatggtata aatagtgaca   44460
caaatattag atggaataac tgtatagctg gccgagcatt tgtactctgc agtgcagtaa   44520
cagattttga tttcattgtt actattgttg ttccttaaaaa tgtcctatct tttacaagag   44580
cctttgggaa aaacctccag gggcaaacct ctgatgtctt ctttgcagcc ggtagcttga   44640
ctgcagtact gcattcactc aacgaagtga tggaaaatat tgaagtttat aatgaatttt   44700
ggtttgagga agccacaaat ttggcaacca aacttgatat tcaaatgaaa ctccctggga   44760
aattccgcag agctcaccag ggtaacttgg aatctcagct aaccttttgag agttactata   44820
```

```
aagaaaccct aagtgtccca acagtggagc acattattca ggaacttaaa gatatattct   44880
cagaacagca cctcaaagct cttaaatgct tatctctggt accctcagtc atgggacaac   44940
tcaaattcaa tactttggag gaacaccatg ctgacatgta tagaagtgac ttacccaatc   45000 ctgcacacgct gtcagctgag cttcattgtt ggggaatcaa atggaaacac agggggaaag   45060
atatagagct tccgtccacc atctatgaag ccctccaact gcctgacatc aagttttttc   45120
ctaatgtgta tgcattgctg aaggtcctgt gtattcttct gtgatgaagg ttgagaatga   45180
gcggtatgaa aatggatgaa agcgtcttaa agcatatttg aggaacactt tgacagacca   45240
aaggtcaagt aacttggctt tgcttaacat aaattttgat ataaaacacg acctggattt   45300
aatggtggac acatatatta aactctatac aagtaagtca gagcttccta cagataattc   45360
cgaaactgtg gaaaatacct aagagacttt taaaaacagg cttcttata tttgatattt    45420 ggaagtaaaa gccgtaaggt gtatgtaggc cacttaatca ctaaatatct ttgcctatag   45480
gactccattg aatacattag ccattgataa tctacctgtt taaatggccc ctgtttgaac   45540
tctcaagctt tgaagaccta cctgttcttc cagaagagaa cgttgaaagt tccatgtttc   45600
cttttgcgtg atctctgttg acggcactct ggaattgttt cagttaagtc attttagaca   45660
tagcatttat tatcactgtg gatctctact tgttgggtgt tatgaattct ttgaaaaaat   45720
atattttgaa gaggtgtggg aggaaggaat acatttata aaatgttata gttaagccca    45780
caattgacct ttgactaata ggagttttaa gtatgttaaa aatctatact ggacagttgc   45840
aagaaattac cagagaaaag cttgtgagct caccaaacaa ggatttcagt gtagattttg   45900
tctttctcaa acttaaagaa acaaatgaca aagtttgaat ggaaaagcct gctgttgttc   45960
cacatctcat tgctgtttac attcctttgt ggagcctaca tcttcctaag cttttagca    46020 ggtatatgtt gaacacttct gtttcatggt tgagacagaa tcagaggcca tggatactga   46080
caactgattt gtctggtttt tttttttctgt cttttttcca tgactcttat ctactgcctc   46140
atcttgattt ataagcaaaa cctggaaaac ctacaaaata agtgttgtgg tttatctaga   46200
aaaatatgga aaatattgct gttatttttg gtgaagaaaa tcaattttgt atagtttatt   46260
tcaatctaaa taaaatgtga gttttgttta aagctaaaaa aaaaaaagaa cccagcagaa   46320
atcctggaaa taaataattc agtggatgaa attaaaatat atatatacaa tcaagagttc   46380
aacaatagac taaatcaagc agaagaattt ttgaacttgg tcttttaaaa taacaaagcc   46440
agattaaaaa aaaaggtggg gggggaata aaagaataaa agagaatgaa gaaagcctaa   46500
tgacatatag gacaccataa agcaaacaaa tatttgaatt ttataagttc cataagaata   46560
agaaaatgga aatgccatag acaacctatt tattgaaata atatctgaaa aattcttcct   46620
tcttgtgaag gatatagaca tctagatata gaaagctaaa atatctacta gtagattcaa   46680
taaaaatata agtgttctcc aaggcacatt aaagttacac tgtgaaaggt tgaagacaga   46740
gggagaattt taaaaatagc aagagaaaaa catcaagtca catgttgggg gaaatcccat   46800
cagactagca gcctattact cagtaaaaat cttgcaggcc aggagagcat gagaaactat   46860
attcaaagtg ctgagagaaa aatgccaatg aagaatacta tgcccaggaa agctatcctt   46920
taaaaaggat ggagaaataa catcttttc agacaagtaa aaactgaagg aaattcatca    46980
ctactagatc aaccatacaa taaatgcttc agggagtaca acatctataa gtaaaaggat   47040
gatgtctact atttagaaag cacaagaaag aattaaactc acgggtagag cagatacact   47100
aatgaaagca agaaagaaat caaagcttgt cactacagaa aatgaccaaa ctgtaaagat   47160
```

```
aaatattaaa agaggaaaga gaaacaaagg atatacagaa cattcagaaa acagctatca    47220
aaatgacagt agtaagttct cacctattat taacaacatt gaatgtaaat ggtttaaatt    47280
ctacaattat aaagtataga ctggctgaat gggtagaaaa gaaaacacaa aagacccaat    47340
tatatgctgc caacaagaaa ttcacatcat gggtaaagac actatattag tctgtcctca    47400
tgctgctaat aaagacatac ctgagactgg gtaacttata aaggaaagag gttaaatgga    47460
ctcacagttc cacatgtctg ggaaggtctc acagtcatgg tgtaaaacaa gggaagaaca    47520
aagggatatc ttacatgagg gctggcaata gaacttgtat aaggaaattc tcatttataa    47580
aaccatgaga tctcatgaga cttattcact atcacaagaa cagcatggga aagacccaca    47640
atcatgagtc aattacctcc tactgggtcc ctcccacaac acatgggaat tatgggagct    47700
acaattcaag atgagatttg ggtgaggaca cagccaaacc atatcagaca caaatagact    47760
gaaagtgaag tgacggaaac catatcccat gcatatgaaa gccaaaactt tgcaggagta    47820
gctatactta tatcgacaa agtagactta aagtcaaaga acataacaag agataaagag     47880
gtctagtatg taatgatgaa gggatcaatt cattaacagg atataacaat tgtaaatata    47940
tatggactca acactggagc actaagatat ataaagcaaa tattattaga gctaaagaga    48000
gagatagact ccaatacagt aagagttgga aatttcagca ccccactttc agcactgggg    48060
agatcatcta gagagaaaat caacaaagaa atattggact taatctgtgc tatagaccaa    48120
gtggacctag caggtattta cgtaatattt tatccaacag ctacagaata cacattcttt    48180
tcaccagcac atggaacgtt cttcaggata aaccatatgc tagtccacaa aacaagtctc    48240
aaaaattttt taaaaatcaa aatcatgttg agtaccttcc cagagtacaa tggaataaaa    48300
ctatagatca ataataagag aaattttgga aactgtacaa atacattgaa ataaagcaat    48360
aggcttcaaa gtgatcatta gattaatgaa aaaatgaaga tcaaaatgaa aaaaaatctg    48420
aaacaaatga aaatgtaaac acaacatacc caaacctatg gaatatagta aaagtagtgc    48480
taagagggaa tgttatagca atagccatct acatcaaaaa agtggaaaga tttcaaataa    48540
acatcctaac agtgcaccac aaggaactag aaaagcaaga gggatccaag cccaaaatta    48600
atacaaagaa ggcaaaaata aagagcagaa aaaaaggaaa tagaaactaa aagctaaact    48660
aaactaaata ataaaactat taacaaaaca aaattttatt tcttgaaaag ataaacataa    48720
accacttgga aaataaaata aaaataaaat cctagaaaaa atttaaccaa ggagatgaaa    48780
agataaaaaa taaaccacta gctggactaa ctaataaaga gagaagaccc aaataagtaa    48840
atcagaaaca aataaagcac acattacaac tgataccaca gaaatataaa ggactatcag    48900
agattatttt gagcaactat acactaacaa attggaaaac ctagcggaaa tgaatcaatt    48960
cctaaataca tctaccctgt caagacagaa ccagaaataa ataggaaaca tgaacagacc    49020
aataacgagt aacaagactg aatcaataat aaaattctcc caaaaagaa aagcccagga     49080 ccagatggct ttatttctga gttctaccaa acttttaaag caagacaaat gccaattctt    49140
ctcaagctat tcttaaagaa aaaaacgaaa aggagagaat tcttcttaat tcattctaca    49200
aagccagcat taccctgata gcaataccag ataaagagac aaccaaaaag aaaactacaa    49260
gccaatatgc aaagtttctc aacaaaatac taacaaactg aatctaacaa cacatctaaa    49320
aaataataga acataataaa gtgggattta tcccaaggat gcaagaagg ttcaacatac     49380 acaaatcaat aaatgtgata catcacttca aaagagtgaa gaacaaaaac catatgatta    49440
tctcaactag cacagaaaaa aagcatttga tataattcaa gaactcttta tgatgaaaac    49500
tcttaacaaa ttggcataga aacaaagtat tgcaactcaa taaaggccat atattattaa    49560
```

```
cccacagcta tcatcttaca gaatgaggaa aaactgaaag tctttcttat aataactgaa    49620
taagacaagg atgcccactt ttaccactcc tattcaacat ctcactggaa gccctagcca    49680
gagcaattag gcaagagaaa gaaataaaag atgtccaagt tagaaaagaa gaagtcaatt    49740
gtccctcttt gcagatgaca tgattataca tagaaaaatc taaatactcc accaggaaac    49800
tcttagaact gataaatgaa ttcagtaaag ttgccagata caaaattaac atacgagaat    49860
cagtagcatt ttttatatc ataatgaact agctgaagga gaaatcaaga aagcaatctg    49920
atttacaatt tttgccagga aaataaaata aaaataaaaa cctagaaata aatttaacca    49980
aggaggtgaa gacctctaca atgaaaacta caaaacacta atgaaagact gaagagaata    50040
caaacaactg taaagatata atatgcctat ggattggaaa aattaatatt gttaaaatga    50100
ccatactaca caaagcaatc tacaacttta atgcaatccc tatcataata ccaatgacat    50160
ttttcacaga aagagaaaaa acagtcctaa aatttgtatg gaaatacaaa ggacttgaat    50220
agcaaaagca atactgctca aaagaacaa agctggaggt ctcatactat ataatttcaa    50280
aatatactac aaagctataa ccaaaacaac atagcactgg tataaaaaca gacacataga    50340
ccaagggaat ggaatagaga agccagaaat aaatcaatgt atttacagcc aacttatttt    50400
tggcaaatat gaaagaacat acatgggaaa atgatggtct ctttaataaa tagtgctagg    50460
aaaactggat gttcacaggc agaagaagga aactagaccc ctatctctca ccatatataa    50520
gaatcaactt gaaatggata aaagacttaa acatgaaacc cagaaatata aaccactag    50580 aagagaatat aggagaaatg cttcagaaca tttttaggga aagatattgt ggctgagatt    50640
tcaaaagcac aagtagcaaa aacaaaaga aacaaatgtg actgtattaa actaaaaact    50700
tctacacagc aatggaaata attaacagag tggagagaca acctatagaa tgagacaaaa    50760
tatgtgcaaa ttattcatcc aacaagggat taattttcag aatatataag gaattcatac    50820
agctcaacag caaaacaaaa caacaacaaa aacctgatta aaaagtgagc aaagccttgt    50880
agcatagttt gaagtcaggt agcgtgacgc ctccagcttt gttctttttg cttaggattg    50940
tcttggctat acgggctctt ttttggttct atgtgaaatt taaagtagct ttttctaact    51000
ctgtgaagaa tttcagtgat agcttgttgg gaatagcatt gaatctataa attgctttgg    51060
gcagtatggc cattttcacg acattgattc ttctttccat gagcatggaa tgttttcca    51120 tttgcttgtg tcctctctta tttccttgag cagtggtttg tagttctcct tcaagaggtc    51180
cttcacatcc cttgtaagtt gtattcctag ttattttatt ctctttgtag caattgtgaa    51240
ttggagtttt ctcatgattt ggctctctat tattggttta tagggatgct tgtgattttt    51300
gcacattgat tttgtatcct gagactttgc tgaagttgct tatcagctta aggagttttg    51360
gggctgagac gatgaggttt tctaaatata caatcacatc atctgcaaac agagataatt    51420
tcacatcctc tcttcctatt tgaatatcct ttatttcttt ctcttgcctg attgccctgg    51480
ccagaacttc caatactatg ttgaatagga gtggtgagag agggcatcct tgttttgtac    51540
cagttttcaa aggaaatgta accgaacagc atggtaatgg aaccaaaaca aatatataga    51600
ccaattgaac agaaccgagg cctcagaaat agcatcacac atctcagcc atctttgaca    51660 aacctgacaa aaacaggaaa tggggaaagg tttccctatt taataatgg cgctgggaaa    51720 actggctagc catatgcaga aaactgaaac tggacccctt ccttatgcct tagaacaaaa    51780
attaactcaa gatggattaa agacttaaac atacgaccta aaaccataaa aaccctagaa    51840 gaaacctag gcaataccat tcacgacata ggcatgggaa gacttcatga ctaaaacacc    51900
```

```
aaaagcaatg gcaacaaagg cccaaattga caaatggtat ctatttaaac taaagagctt   51960
ctgcacagca aaagaaacta taatcagagt gaacaggtta cctacagaat gggagaaaat   52020
gtttgcaatt tatccacctg acaaagacct aatatccaga atctacaagg aacttaaaca   52080 aattataag aaaaaaataa acaaacccat caaaaagtgg gcaaaggata tgaacagaca    52140
cttttcaaat ttatgcggcc aacaaacata tcaaaaaaag ttcatcatca ctggtcatta   52200
gagaaatgca atcaaaacc acaaagagat atcatctcac accagttaga atggcgatca    52260
ttaaaaagtc aggaaacaac agatgctgga gaggatgtgg agaaatagga acgtttttgc   52320
actgtttgta ggagtgtaaa ttagttcaac cattgtggaa gacagtgtgg tgattcctca   52380
aggatctaga actataaata ccatttgacc caccaatccc atatacccag aggattttaa   52440
atcattctac tataaagaca cattcacata tatgtttatt gcagctattc acaatagcaa   52500
agacttggaa ccaacccaaa tgcccatcaa tgttagactg gataaagaaa acgtggcaca   52560
tatacaccat ggaatactat acagccataa aaataatga gttcatgtcc tttgcaggga    52620
catggatgaa gcaggaaacc atcattctca gcaaactaac acaggaacag aaaaccaaag   52680
accgcacgtt ctcactccta agtgggagtt gaacaatgag aacatattgg cacagggagg   52740
ggaacatcac acattgggc ctgtcgcagg gtggggaca aggggagaga tagcattaag     52800
agagatacct aatgtagatg acgggttgac gggtgcaaca aaccaccatg gcacatgtat   52860
acctatgtta caagcctgca cgttctgtat cccagaactt caagtataat aataaaacaa   52920
aagtgagcaa aggatgtgaa tagacattta tgaaactaaa acatacaaat ggccaataag   52980
tatgagaaaa aatgctcaag atcactaatc actggaaaaa aatgcaaatc aataccacaa   53040
tgagctatca cacctgtcag aatggctatt atcaaaaaga caaagataa gtgttgatga    53100 ggatgtggag aaaaggaaac cattggaatt gttggtggga atgtgaatta gtacagccat   53160
tattgaaaac agtatgaagt ttcctcacaa aattaaaaat ggaactagca tgtgctcctg   53220
caatctcact accaagcagt tatccaaagg aaaggaaatc agtctattaa agggacacct   53280
gtaacttaat gtttattgca gcagtattca caatggctaa gacatggaat taacttaggt   53340
gtccatcaac aaacaaatgg atgaagaaaa tgtagtatat atacactcaa tgaaataacc   53400
ttcaggtata aaaaaagtat gaaatcctgt cactcacagc aacacagatg agcctggagg   53460
actttatatt aagccaaatc ggtcagtcac agaaagataa acaccacatg ctgtcattta   53520
tatgtgggag ctaaaacata attgagttca tggaagtaga gaataaaatt gtgggtatta   53580
aaggcacaaa agggtaggag ggaggggacg atagggagaa gttggttaac agatgcaaaa   53640
ttataactag ataggaggaa ttagccctgg cattctgcag cactgcaggg tgaacatagt   53700
ttaccataat ttattgtata tgctcagaaa gctagaatag aggatttgga ttgttcataa   53760
cagaaagaaa tgatgaatgt tagagggat ggatatgcta attccctga tttgatcatt      53820 acacattgta tatcacatat ggaaatatat cactgtgtca tccataaata tgtacgacta   53880
ttgtgtcaac taaaaataaa aggaaaaaaa gtaaaaataa gggaaagtat ttattttacc   53940
ttcacttatt ctctgatgtt gttccttcct ttatttagat ccatgtttct aacttatgta   54000
attttccttc ttcctgaata gcttctgcta agatttcttg caaggcaggt ttacttgtaa   54060
caaattctct caattttgt ttgtctgaga aaggctttat tcctccttca cttttgaagg    54120
ctaaattcac agagtacata atttaaacac tggttttta ctcttaacat tttgaatatt    54180
tcattcctct ctcttttgc ttgcatgatt tctgtggtga atttggatgt aattcttatc    54240
tttgctcttc tataagtaag ttgtttcttt tctccacttt gcattctttt ctagatattt   54300
```

```
tcttcatccc ttgattttc tttttctgtc tcttctcctt ttttatattc ccattacatg    54360
tatgctactc cttttgtagt tgtcccacag ttcttagata ttctgttctt ttttatcagt    54420 ttttttttt ttgaattttt gcttctcagt tttggaagtt tctgttgtcc tatcattaga    54480
ctccaagatt ctttcctcag ctatgtgaag tctactaatg agcccatcaa aggcatattt    54540
tctttctgtt tttgatcttt atcatttaa aattatttcc tagaatttta atctctctgc    54600
ttaaatttcc tatctgttct tgtctgttgt ctaattttt cattacagct ctgacagctc    54660
tgagcatatt aatcatagac tttatttatt ttctttttt gagacggagt ctcgctctgt    54720
tgcccaggct ggagtgcagt ggcacgatct cggctcacag aaacctccac ctctcaggtt    54780
cacgccattc tcctgcctca gcctcctgag tagctgggac tacaggtgcc cgccaccatg    54840
tccagctaat ttttggtat ttttagtaga cgggtttt caccgtgtta gccaggatgg    54900
tctcgatctc ctgacctcgt gatctgcctg ccttggcctc tcaaagtgct gggattacag    54960
gcgtgagcca ccacgcctgg cctcaatcat agacttttaa aaagattct gttctgataa    55020 ttccaacctc atggccatag gtaagtctag tccttatgct tgctctggct cttcaaactg    55080
tgtgttttgc cttctagtat gccttgtaat ttttttttc atagctgatt ataatgttct    55140
gagtaaaaga aactgtgata acaggcctt tagtgatgtc acaatacggt gtggaaaaag    55200
gggatgtgtt ctataagcct gtgattaggt cttagtcttt tggcgagcct gtgacctgga    55260
ctgtgaactt tcagtgctgc tctttttt ccctcctta ggtggtacag ggcagccttc    55320
caacatgtga aaaactagag gacccttgag ctgggtattt ttttcccag gcagatcaga    55380 ctctgataaa acctcagaag gttaggctct ggtaaaatag tcacccttga gtttaggccc    55440 tttaaggag aacagactat tcagcttttt agaaattagt atttttttt tgagacaggg    55500 tcttactgtc acccaggctg gagtgcagtg atataaatca tggctcactg cagccttgac    55560
ctcctgggtt caagtgatgc tcctatttca acctgagtag ctgggaccac cagcatgtgc    55620
caccatgcat ggctaattt tttgtaattg tttgtaaaga taggatctca ctatgttgtc    55680
caggctggtc tcaaacttct gggctcaagt gatcctccca cctctggctt attttataat    55740 agtttttcc cctcctccta ccagaagcac aagaggactt tctcatctga tacttactgt    55800
gaggacctag tagttagagc tcctaaagat caaactcata aaagtatata gcccccacaa    55860
ctatgactgg gtaccttgg agtttttaat tctctaagtt gtttcacact gagccttcag    55920
caatttgcca attacagttt aattttttct accccacaa tggttgctat ggaggtttct    55980
gctcatggat ctctgcttca gtaagttgtg gttctatctg tttctctaat ttggggatcc    56040
tctctttctc tccaacttta gggcagtggt ttgccctgtg acctcacttc tctgatctaa    56100
gaagagttgt tgattttttt ttaatgggtt tagcttttta cttttaagta tggattggca    56160
acttctaagc ttcttatatg ccaaatggaa aagtagaagt tctcaaaaca actatttat    56220 actaatattt tattgattta tatagtatta agtattataa ttaaatgcta agtataactt    56280
agtgttaagg aattgactta gtcaataagc aactgaaatg gtgggagaaa atatacacga    56340
gtacataaga aactaaacta ctagtttgga gtcttcattg ttctctgggc attagtgaat    56400 atgtttgac agaaggaata gaaactattg atcatccaga aagtcagtta aatgacagtt    56460
aaacttctgg tagataagtg tgttcaagtg tctacatatg cattcacatt taaatatagg    56520
cttctacata gtacctttt ctcttaatgt tttattatag attaccact tgtttatgaa    56580 cattacctga aaacaaatat atctgcttaa tatttattt tattttccat catctatttt    56640
```

```
accattccat tattagcttt cttttctatt ttagctgttt tctttatgta gataaatttt    56700
gaacaagact caatttactt gaccttttaa ttggcattta ctatggacca ccacttcctc    56760
aaaacaatcc attctcttgg ctttccttct aactctctgg ctttactatt tgtctatttg    56820
acatctgttc ctgaatcttt gaaagtcagc tcaaacgtca tctgttaaaa acctaacaca    56880
taatttatac actccacctc ttcttctatt tcctatctca atggcaacac aatactgatg    56940
gtaaccagct taccatagtt aggcttataa tttttgaatt tacaatgggc ttattggaat    57000 gtaaaccat  tgtaagttaa ggagcatctg actcttttgt tgtactcacc agacaactca    57060
agaatgatcc ttgatatgtc catcttgctt aattttattt tcaaatcac  attaaatttg    57120 cttatttctc aaatctattc atgtatttct agattctctc ttactatcaa gtgcaataaa    57180
taattatgtt aagcactgac tatgtaatag cctcataaag attcacccat atactttctt    57240
gaatctctcc aaaccatctg gcatatggct gttaatatga ccattgaaaa aagtaaacta    57300
gaaaaactgt tcccatgttt gtaagtacaa atacattaat tattgctttt aggattgata    57360
caaaacttct taaaatatcc ttaaggccac acataatttg gtctcttcca gctctggctt    57420
tatgtcaaac cagttctgtc tcttcctctc tcagccatat tcctactttc ccttgctctc    57480
ttctttctag ccacatacag gccatgatcc ctctctcttc aaagtagtca cctatactat    57540
ttgctactga atcccccttt tccctaaggt acttatgatt gagatctctt gtgaagtatc    57600
cttctccggg aagtattcat tgaggttttt aagtaaaatc ttcttgtata ggcttcatgg    57660
cagcatatat cttgtattca taacagttct caagttggga attgattgct gttattggat    57720
taatgttttt gccaccaaat aataaacttc ttgagggaag gagccacgta tgattttgat    57780
ccctgttgta ttcctaatac taaatggcac atggtaaatg ctcaaatatt tgatcaaaga    57840
ataaatgact ttaattttaaa ctaagaatta actaataagt catactataa tctgctaagc    57900
tacctgacaa atggtaaaaa ttgtagcaat tgagatagaa ttccaggaac aatatacacc    57960
tttttcaaat ttcatacaga gtagattttc taaaaaataa gcagcgcatt ttaaaaggcc    58020
ccctaaataa ggcttcagat ggcacaaggc catggatagg ttgtcatagt gatgatcaga    58080
aatgaaaaat atttctactt tacttgaggt aaggagtttg aggacagcct ggccaacatg    58140
gtgaaaccca gtgtctacta aaaatataaa cattagctgg ctttggtggt gcatgcctgg    58200
aatccagtta cttaggaagc tgaggcagga gaattgcttg aacccaggag gcagaggttg    58260
cagtgagccg agaccatgcc actgcactcc agcctgggca acagacccca tctcaaaaaa    58320
aaaaaaaaaa aaaagcaat  gaagtatatt tctataggga ccaactttat ttatagcaag    58380
agacatgaga ctgaatatat tctatgccaa aactttccaa tccttagaat cagccctaca    58440
aaaagaaaga aaaagaaaca gaaaggaagc agcaatcagc tatgagcaat aattagacat    58500
tcgtttgcta gctctagcac atgtgaccat gaagagtaac tgtgaaccat attgactttc    58560
tctcctgaaa agaaaaatat gaaaaaaatt cagaagaaaa ctgtcctatc acaaagaata    58620
cagaaattgg gtaagaatga acagctgttt catttcatta cctttgccct tttccacctt    58680
tatttttgga caattagttg atctaaaaag caatagttct ctatcagtca gtttttgcta    58740
caaacacata cacacacaga aagagagaaa ggcatacagt aatatgcatt taccttaggt    58800
tcacaggtat gcagtttggc tgagttcgat tacctccatg tgtttcattc taagtcataa    58860
gatggaagga gcagctgtat gggagtttta acatatgcac aaagatactc cacctttacaa   58920 gaggtacagc ttaaattccc tcctcttgag tgtggattag aattagtgac tcactgcaag    58980
caactgaata atgaggaaat ggcagtgtgt gacttccatg taataaaaga catggcttcc    59040
```

```
tccttgcttt ctcttacatt gatacttggg ggaaagtcag caactatctt ggaaggatat   59100
tgaagaaagc ctgtggagaa actcatgtgg tgagaaattg aggcattctg ccaataccty   59160
catgaatagg tcatcttggg aatagatcct ctaatcctga tggagtccag atgactacag   59220
acatgaccaa catcttgact gcctcctcat gaaagatgaa ctagaagctc ccggttaggc   59280
agcttccaaa ttcttgatcc acagaaactg tactgaaagc atcaatttct taccacatgt   59340
cttttggaca aactcaacat taatggacag aggagcatac ttctctatag taggctaaat   59400
aatggccacc cagataaaaa aattctaatc tgaaatgta taaggtaaag gaatctacag    59460
atgtgattga attaagaatg ttggtgtgat aagtttattt tggattatct tggtgggccc   59520
taaatgctat cacaagttcc ttctaagaga aaagcaggag aagacttgac acccacacaa   59580
agaaggtgat gtgaagatgg aggcagagac tggagccact aggccacaag ccaaggaaca   59640
ctaaggaatg ctggcagaca ccagaagata gaagaggcaa acaatgcatg ctctcccaga   59700
gcctctagaa atgtgagata taagttttt attgttttga gcctccaaat tttttggtaat   59760 ttgttacatc agccatatgg aatgaaaaca tcctctcatt tgttgagttt agatgttaaa   59820
tactggctga acaataatct actctacttt agcatctttt caaaaataat cacaaaattt   59880
aaaaggaaaa ttatgcactg gtactagcaa aataaatgaa caaatgaatt aacacaaaat   59940
aggcaaaagg aaaatgaagt atctagacca aagtttaatt atccatgaaa gcaatggaaa   60000
atgtgaagtc tctaagaaac caatgtaaaa agagctaaaa acaatatagt atgaaagaaa   60060
ccagaaagaa acaaatgttc tttggatttt ggagaaatac agagactaaa ataaaaacca   60120
gaaatgaata ctccattaaa acaggcatat gaaagacagg atgggtaaaa accacacaaa   60180
acgaaattgt gtgtttgtgt atatatacgt gtgtacacac atacacgaaa agaaaaagtt   60240
caatagaaga ttcatttttt atgtaattag tgtttctaaa aagatactt aaaatgtaat    60300 ttaaaaattc aaagatagaa gaaaactatg ctgaaattaa agaagatata attctacaaa   60360
tgtaaagaac attatgtatt ttaagaactt gaaagaaaag gagtgggaa gtggccaaga    60420 tggccaacta gaagcagctc gtgtgagtgg ctctcacaaa gagggacaaa agggcgagta   60480
aatacagcac cttccactga acatccaag tactcgcact gggactaatc aaggaaacaa    60540
cttgacccat ggagaacata gaaaacaaag gcaggacgac agcccacctg ggcacgacac   60600
ccagccaggt gaacctcccc tgcccagaga atcggtgagt gaatgtgtga ccctggaaac   60660
cacactcttc ccacgaatct ttgcaacctc gagttgggag atccctctt gaacccactc    60720 catcagggct ttcagtctaa tacacagaga tacgggagtc ttggcagaga agctgctcag   60780
gcacatgttg gagaaccagg aactgtagat attccaccgtt caggcttccc ggcaaaagta   60840
actgcaactc cagaaaagca ggagattaga tccttgtgca tacccttagg aaagaggctg   60900
aatccagtgg gccaagcagc gatggtctgt aggccctact tccatggtgc ctcaaaggat   60960
aagacacatt ggcttggaat tccagccagc caccagcagc agtgttgtgc ctacctggga   61020
cagagttccc agggagaggg gaaggccacc atcttcactg tttgggcaag tcacctttt    61080 cagcctgcag actttgaaga gtccaaaccg atcgggcaga agggatcccc caacacagca   61140
caattgctct accaacacgt ggccagactg cttctttaag caggtccctg agccatccct   61200
ccttattggg caggacctcc caaccagggc ctccagccat cccgctggt gttctctggc    61260 ctacagagat ttgaaaactc cctgggacag aggtctcaga gggaggggtg ggctgacatc   61320
tctgctattt gggtactgaa cctgtccagc ctgtgggctt tggagagccc aagccaacag   61380
```

```
gcggtgaagc gttacccag cactgcgcag ctgctctaca aaagcatggc cagactgctt    61440
ctataagtgg gtccccaatc ctcttcctcc tgactgggca agacctccca accaggatct    61500
ccagccacct cctgcaggtg cgttccacct ggcaacaggt tcatacctcc ctgggccaga    61560
gctcttagaa gaagtggcag gctgccatct ttgctgtttt gcagccttca ctggtgatac    61620
cttcagctac cggaaaatcc aaggcaacta gggactggag tagacccca gcaaaccaca     61680 gcagccctat ggaaaattgg ccaaattgtg ccaggggaa aaaaaaggt aggcaacgtc      61740 gaacattgaa ggtagattag ataagctcac agaaatgaga aagaatcaga gcaagaatgc    61800
tgaaacctca aaaagcctga gtgccctctt tcctccagct gacctcatta cctctccagc    61860
aagggttcaa aatagccagt atagagaagt acttaatcct cctgataggg ctgaaaaaca    61920
cactacaaga atttcgtaat gcaatcacaa gtattaatag tagaatagac caaacagagg    61980
aaagaatttc agagcttaat gaaatatggc aggcagacaa atgtagagaa aaagaatga     62040 aaaggaatga acaaaacctc cgagaaatat ggaataccat atcacaccag tcagaatggc    62100
tataattaaa aagtcaaaaa ataacatgct ggcaaggttg tgaagaaaaa ggaatgctta    62160
tacactgttg gtgggaatgt aaatcagttc agccattgtg gaagatggta tggcaatttc    62220
tcaaagacct aaagacagat atactattca acccagcagt cccattactg ggcatataac    62280
caagggaata taaatcattc tgttataaag acacatgcac atgtatgttc attgcagcac    62340
tattcacaat ggcaaagaca tggaatcaaa ctaaatggcc atcaataatg gactggataa    62400
agaaaatgtg gtacgtatac accatggaac actatgcagc cacaaaaaag aatgagatca    62460
atgagatcat gtcctttgca gggacatgga tggagctgga ggccattatc cttagcaaac    62520
taatgcagga acagaaaacc aaataccaca tgttctcact tataagtggc agctaaatga    62580
tcagaacaca tggacacata caggggaaca atacacactg gggcttttg gaggatggag    62640 ggtaggaaga gggagaggat caaaaaacaa ttaatggata ctaggcttaa tacctgggtg    62700
atgaaataat ctatacaaaa aaacccatg acacaagttt acctatgtaa caacctgca     62760 cttgtaccc tggacttaaa ataaatgttt aaaaaataga gaaagaaaaa gacactaaaa    62820
acatgaaaag atatgaaagc atataactca ctgtaaagat aaagcataaa attcaccata    62880
aagataaaat atagtcaaat tcagagggct gtaatgaatt tgtatgtaat taagtgtata    62940
ctgtaattat agtttataag ttacttttcc tctactataa gagttaaaag acaaagtat     63000 taaaaataa cttcacctaa aaaagaaac ttagccaatg tcatgtttta tactagaaaa      63060
tactgcagtt cagtcttata atcctggctt ttctcttctg attttccata tttataaaat    63120
atttgaagaa atttgtttct tatgtacatc ttgacatatg tgatatatga tttgtttctt    63180
tttatttttt atttttttct gagacagagt cttgctctgt tgcccaggct ggagtgcagt    63240
ggcgtgatct cagctcactg caagctccgc ctcccaggtt caagcgattc tcctgcctca    63300
gcctcccaag cagctgagat tacaggcatg tgccaccaca cccggctaat tttttttttt    63360
ttttttgtat tttagtagga gatgggtttt caccatgttg gccaggctgg tctcgaacta    63420
ctgacctcac gatctaccca ctttggcctc ccaagggct gggattacag gcataaggca     63480
ccatgcctag ctgtgatttg tttcttattt gcatctggac atatgtgaca tgtgaataag    63540
aaacaattat tgggactttg gtcaagtaat tctattcttt gttaaatcaa aagatggcca    63600
tctaagtttc ttttcaacac catgtatcta taattcttac tctgagccat tcttctgata    63660
gggcatgaat gaaaagaatt ttagaaagca acagtaattg gcaatcatat agatctatat    63720
tagatgcatt aataaaatgt actaaggtcg atgaattaat aactgtgacc tctataggag    63780
```

```
tcaaccttttt aagggtatag taacacattt acattccata tcaagcatta ggtaaaaaat    63840
aatcaactgg tataacatta tctttctgtg gatctgccaa aaataagttt tattaataac    63900
ctagaacagc cacctaacca atatggcttt ttaaatattc atgtgtcatg caatttgcta    63960
acatgttgca agaaattggc attcattatg tgacatattg tctcatacga tatttttggt    64020
gaattggaag ataacatata gagtagctac acgtttcacc ttctttttg aaggatgaca    64080 tggtaaaaat taaatactct atgttttatc aaagaaaaaa ttatgtatga gttattgtcc    64140
ttggggtatg gggaagtcaa catgaaaatg acttaatagg caaatattaa ttatccacta    64200
aattttcagg aatatgtaca atggcaatgt gaagatagtt attgaaaatg tatcttttac    64260
acttgagatg tatgtattca gacacttctt gcagataaag ctgatagtat atacatttta    64320
aaatcagggt aaacccagac atcatcatgc ttttcacagg tgataagagt aatgaatact    64380
tttctgagag gcagatgagg attcaaagcc catgactaaa tcctgccatt gctccacttc    64440
ttatcctgtt tctctggaga cattacatag gctaagattg ctttcagtcc cagaagctct    64500
gatagcatgg agttgctagt ttgctggaca gagctagtcc aacccggtgc ataagaaaat    64560 ctgaaaacctt aggaggtttt tcctaatatc aactaaatta ttgatttaga taatctctac    64620
cttcttctac tacattcctt gtaaatgaaa aaaaaatag cgcacatatc agtctgcttt    64680
ctcactccta tgtttataat acacacatat aattacactg tctcaggaaa attctacctc    64740
aaccatccca gaaaattgga ttgctaaaaa tgttgtgaac aaatttcaac cttaattctc    64800
actgtcaatt tcaaagtact aatgcagatg gttttatatt ccttgcacat ccaattaatt    64860
agttgtgact gttgaaaata ctatgttgat tataagcctg tagtctcagc tcaactgaaa    64920
agagtgtaaa acagacaact gatatgaagg ggtaaagggt ttaggtatgt tatacatttg    64980
tgattctttc tcttatgtgt tgagctttgt atggatccct tcattctaat ataaattcct    65040
tttcttgtta tttgttgatg gcaggaaatt tgactgaata acctcttaag ttcatctcaa    65100
cttaatgact tcacatttta taatactttg tctataaagc ataacttcta aaataggtac    65160
ttctatttcc ctagatgagc cagattctct tagagaattc tgggattcaa ttatgggatc    65220
tgggaggggc tctaaatatg ggaggatttg tgtatacact tatttatcct tcaactatag    65280
aaaatgattc ctcatgctta gtcagctgag ccaggcaaaa cttatttcc ttaaaatgca    65340 catataaata tcgatatta taagattatt attttttata attacaagat attagaaaag    65400
tactcagttt taaccatatt attttatgtt atttattaca ggacagcatg aaagaaattg    65460
gtagcaattg cctgaataat gaatttaact tttttaaaag acatatctgt gatgctaata    65520
aggtaatgat aattatttgg agtttgtcat tcaagcttga ttttatagaa gcttctattt    65580
tttgtgcctc tgttagacaa ttatatgaat actattaata tttgcagcct gatcacataa    65640
ttcccattga ttaaatcata ctatggccca attttatatt tttgttttac aaatagtcct    65700
gtgcttatta aataacaagt tttttttgtt tcaccattct attttttacc ttgaaaatac    65760
tagaattgtc gaattcaaag acacacctat ctcttatttt ctttctttct ttctttcttt    65820 gtttttttt ttggaggcag agtttcgctc tgtcaccagg ctggagtgta gtggcgcaat    65880
ctcagctcac tgcaaactcc gcctcctggt ttcaagcgat tctcctgcct cagtctcccg    65940
agtaactggg tctacaggca tgcaccacca cacccaacta attttttgtat ttttagtgga    66000 gacgggggttt caccatgctg gccaggatga tctcgatctc ctgacctcat gatccgcctg    66060
cctccgcctc ccaaagtgct gggattacag gcgtgagcca cggtgcctgg cctctaaatt    66120
```

```
tcttatacag aaaaatactt gttaatgtga atgcttgcac acatacaaat ataagtcatt   66180
ggtataattt agttggaagc gtcttgaaaa tttttctttc aatatttgct tatctctaaa   66240
tgattaccac atctagttgg tataatatta cactttaaaa aacctaaaaa gtttatatca   66300
tttctcccta cagaaacaag tgtgctattt catagtcttt taaaaactca cagtagctaa   66360
gttagcctca tggcatctca aaccataaaa ttcttttttt taaatttctt aatttaaata   66420
tctgcaaaac ttatgtttta ggtgactaca gtcctttatt ttcttattat cagctattct   66480
tccatagctc aaaagatgca agaaatacta agaaaaaacc acacatacct cttataatac   66540
attgttgctt ccagaagtct tctccttcgg ttatcatgtt taaaattgaa taatcttcta   66600
atatgttcac acataagcga taagatcaca taagcataat agagaaaaca aactttaaaa   66660
gtcaagataa ttattaaacc aagttctaag aacttcatgc tgtcacctag gagccaaaca   66720
gttttagttc tgttacttgt caatcacatg attaactgga atagaaagct ggggtggagg   66780
cggggcatta cctagcaaca tagctcaagc tctaggctcc ttaagaaagc ttataatttc   66840
ttaatatttt atttgaacca tggcccttct gacttttttcc tataatagga aggtatgttt   66900
ttattccgtg ctgctcgcaa gttgaggcaa tttcttaaaa tgaatagcac tggtgatttt   66960
gatctccact tattaaaagt ttcagaaggc acaacaatac tgttgaactg cactggccag   67020
gtaagctaag gactatttac tttgaataaa aatattaaat actcctgtgc caagatacca   67080
ctattctctg atgatcacat ccattatcat agaatcctaa gtgtttatta tcatctaaag   67140
ttgaagtatg tttactcaat cctagaagag gaaaggctca gtttggaaat acctatttat   67200
ctcttggcta gagtgaattg tttgtgaaag gggagtaaaa aataaataaa taaattcttc   67260
attgccataa taacttccaa ggatactagg gtgatatatt gggtggggaa tggtaaattt   67320
ctatatctaa aacttattaa tagctttaat ccatatatgt acacatttac aagaactcct   67380
agtcaataaa acaggaaatc aaatgtattt aacaaatatc tttataggct taaactagac   67440
ataaacatgt ccaacaattt tcccttcttt aaataatttt gatacaaata gggctaatat   67500
tttcctactt ttctactagt ggttatgaac taaaacaaca aaaccaaata tggaagacat   67560
catctagaga ctagacagca gtttccttat ctacaaaatg cagaaaaaca tatctacatt   67620
gtgggatttg aaaggattaa atggcataac acatgtaaag tgcttagtac taaaaagttt   67680
tcaatattta atacagtgct ttatttttatt tgtattattt acctcttttt ggattttacc   67740
agctgccaca caaaccaaa agtttatttt atggttttaa atattttctt aaataacatt   67800
tttatgactt aaaaaagaat tttgttttgt ttgagcacta gtagtttccc atagaaggta   67860
aaatggtaag attatctttg aatcctattg acagtgataa aaatgtagat tatctattat   67920
ataacttgga tagcctcatt tatcattgct ttatgtactt gatggaagca agtctcctct   67980
tagtgtgctg gatttgccaa acttatttcc aaacttgcgt ccttacgttt gtcccctaga   68040
gagcatttct actttttttt tctataaatt ggatctattt tgttctatgc cttcaaggct   68100
cggctcaaga ttcatgaaga cttcctactc tagtctacca tttcttcatt cctacttaac   68160
agcggtttca aagtactgtc taatgcagat aggttttatg ttgcttgcac atccaattaa   68220
ttagttgtga ctgttgaaaa tactgtgttg attataagcc tccactcttg gttcaactga   68280
aaagagtgta aaacggaaaa ctgatatcac ctcttggtct actaagaggt aaaggtctta   68340
ggtatgttat atatttgtga ttcttttctct tatgtattga gctttatatg gatcatcatg   68400
ttccaaaatt aactgtagag aaagaaaata tgcaaataat ttaaatcttt gaaattaaat   68460
tatattacat tgattaactt gatacaagtc acctttttct tgaaataaca aggcaagatg   68520
```

```
ttaaagcagt cagctacact gaattttctt catgagccag gcacgctaca agcttttttac   68580 tattgtttta tttcattttg tttctgataa gtgaagctta ataaaatgta tggccaggat   68640
ttaacaattt cttgttaact ttattttttat attgattaaa attcaagttt tatctctgct   68700
actataccct actatgttaa ttttttcatac ctcacagtag ttaacacagt actaggcaga   68760
cctacaaaat tatggattct gggtattcag aagactgaac tatcttgctt cttcctttac   68820
cctgatattc catttctaaa tcatattaat atttttacttt cttaacaata agaaatttaa   68880
agtagagtct caaatagatt agatgagctg aaggcaatat gaaaattagc aattacaaac   68940
aactggagga gcaatgaaga aatattcaat attataaatg tgactttgtt tttaaggtta   69000
aaggaagaaa accagctgcc ctgggtgaag cccaaccaac aaagagtttg gtgagaataa   69060
ttgtataatt ttccttatgg ttcatcaggt ttttactcaa cttaattcct aattttttcat   69120 tttgaattgt ttccttctta tagctggttt tgaataatt tattataaca ttgataaaag   69180
gagaagcgag gtgcccctca aaatttgat tcctttaaat tgcatttta aacccactat   69240 tttaaaatag aagctgttag ggcaaataca aaagcatgat tttttttttt tttagaagaa   69300
gcagcattaa aatattgcag ctagcacgta aagaaatga acaaataatt tatataggag   69360
aaaataaact agatgacaaa tacatgaaga aaaaagcca tccctgttag tttgtaaaga   69420
aataaaaatt aaacaataag gacttatctt atatatacct cttttattag tgtagattgt   69480
acagtataaa taatatataa tagtatataa acatatattt atacatatac tactagacat   69540
tattagataa attatacaat aatatggaaa atatttatga atgacttaat aaggcagaat   69600
acttaaatgg atctgactaa actttaaaat gatataggta ctaattaagt tgaggcatgg   69660
aaaaatgagc acacctggtt cataaaagtg atggattctt cttttatatt tccattattt   69720
gaccaatagc tacatggcaa catggaaatt ccttactctt ttcagaaaag caaagtgagc   69780
ctgtacactc tgagatttag gaaattctag ggattctatg caaagtggaa catctgaagt   69840
gaatacagaa gctaaaagca atataatcac cctgaaggct tttcactaag agaatttgga   69900
aagtttagaa aagaaaggtt gggtgcggtg gctcacgcct gtaatcccag cactttgggg   69960
gtccgaggtg ggcggatcac aaggtggaaa gatcaagacc atcctggcca acatggtgaa   70020
accccgtctc tactaaaaat acaaaaatta gctgggcgtg gtgcacgcct gtagtcccag   70080
ctactcagga ggctgaggca ggagaatcac ttgaacccag gaggtggagg ttgcagtgag   70140
ccgagatcgc gccactacac tctagcctgg gcaacagagt gggactccgt ctcaaaacaa   70200
aaaacaaaaa acagagcaaa aaaaaaaaaa caaaaaaaaa aaaaaaagaa aagaaaagat   70260
aactattttc ccaggatgca ggggtaaaac caagattctc tgttttttac ttttttagtga   70320 atgcttattc tcggtgtgca aggaaaagta tgaaattttc acatctgtat atttcaaatc   70380
tgcttaggca aatcaacttc aacttgtact taaaaaaatt gtccaggacc ccctattgaa   70440
aacaatatga aagtttgcc tttatatttc cctttgagat ctgttgttta atctttgaaa   70500
tgtattcttt aaaaagtatg tgctagtgtt actaaataca tgacaaaaag agatctgaat   70560
ttgtggccaa attaaaaata ggacagagga gctcaagatt cagtcattat atttacttga   70620
catatattta tttacttgac cttagcagct tatttatctt ctttgcggat cagtttcttc   70680
atctgtgaaa tgagttcaaa tcatcaagtt catatgatga ttaagcaaat aaaatgaagt   70740
aaattatgtt aaacactgag cacaatatat gactgagaga atacccaata acttgttatc   70800
taaattatct agttacccaa taactagtta taatagtttt tatattgctt gcacatccat   70860
```

| | |
|---|---|
| ttacttgcta gtgattgttg aaaacactat gttgatttta accctgaagt ctgggctcaa | 70920 |
| ctgtgaagag tgtaaaacaa acaactgata tcacctcctg gtctaggaag gggtaaaagt | 70980 |
| cactggtatg ctttatattt gtgatcaact agttgttatc taagtgaaga attactctac | 71040 |
| cctgcactat tcccattctc acaggtcaga ggactcagag aaatataact gagtctatac | 71100 |
| agagttactc ctttatatgt ctgttcatgc caagtatctc tttcttccta caggttgtac | 71160 |
| aggtagccct ttttaagatt cttgtcaggt gctaaaacct agcttatgag gcaggcatct | 71220 |
| gacatactct ggtgaaggtt agttgttgga ggagacctta gggtacaagt tccatcagct | 71280 |
| atatccttat tatctttggc aaaataatct gagtattttc aatgttgatt attcttccca | 71340 |
| ctaaaaatac atttttctac attaaagaaa ctcaactgag taacctacaa ttacctttct | 71400 |
| catgaaattc caaacagtgt tattatgtcc actgttaaac tgtgaaaatg gcggtcagct | 71460 |
| gatatagctc tttggagaat cctaagtctt taatcacacc aaccttgaat tttctacatg | 71520 |
| tcagttatca caaagatagt tagaaatcat cgtctttaaa atgtcacaca ggattctacc | 71580 |
| ttttcattgc accagttttt cagtataaag taatatgatg aaaaatagta ttttaaaata | 71640 |
| tatatttttg taaaaatgtg aagtttaaac ttttaaaact ctattctcta ggaagaaaat | 71700 |
| aaatcttttaa aggaacagaa aaaactgaat gacttgtgtt tcctaaagag actattacaa | 71760 |
| gagataaaaa cttgttggaa taaaattttg atgggcacta agaacactg aaaaatatgg | 71820 |
| agtggcaata tagaaacacg aactttagct gcatcctcca agaatctatc tgcttatgca | 71880 |
| gtttttcaga gtggaatgct tcctagaagt tactgaatgc accatggtca aaacggatta | 71940 |
| gggcatttga gaaatgcata ttgtattact agaagatgaa tacaaacaat ggaaactgaa | 72000 |
| tgctccagtc aacaaactat ttcttatata tgtgaacatt tatcaatcag tataattctg | 72060 |
| tactgatttt tgtaagacaa tccatgtaag gtatcagttg caataatact tctcaaacct | 72120 |
| gtttaaatat ttcaagacat taaatctatg aagtatataa tggtttcaaa gattcaaaat | 72180 |
| tgacattgct ttactgtcaa aataatttta tggctcacta tgaatctatt atactgtatt | 72240 |
| aagagtgaaa attgtcttct tctgtgctgg agatgtttta gagttaacaa tgatatatgg | 72300 |
| ataatgccgg tgagaataag agagtcataa accttaagta agcaacagca taacaaggtc | 72360 |
| caagatacct aaaagagatt tcaagagatt taattaatca tgaatgtgta acacagtgcc | 72420 |
| ttcaataaat ggtatagcaa atgttttgac atgaaaaaag gacaatttca aaaaaataaa | 72480 |
| ataaaataaa aataaattca cctagtctaa ggatgctaaa ccttagtact gagttacatt | 72540 |
| gtcatttata tagattataa cttgtctaaa taagtttgca atttgggaga tatatttta | 72600 |
| agataataat atatgtttac ctttaatta atgaaatatc tgtatttaat tttgacacta | 72660 |
| tatctgtata taaatatttt tcatacagca ttacaaattg cttactttgg aatacatttc | 72720 |
| tcctttgata aaataaatga gctatgtatt aa | 72752 |

<210> SEQ ID NO 4
<211> LENGTH: 78
<212> TYPE: DNA
<213> ORGANISM: Unknown
<220> FEATURE:
<223> OTHER INFORMATION: Mammal

<400> SEQUENCE: 4

| | |
|---|---|
| tgcaagcacc aaaaaggtga ccacacttca cattggcgat cgcgggtttc tatctgagga | 60 |
| tgtgaattta tttacaga | 78 |

```
<210> SEQ ID NO 5
<211> LENGTH: 152
<212> TYPE: DNA
<213> ORGANISM: Unknown
<220> FEATURE:
<223> OTHER INFORMATION: Mammal

<400> SEQUENCE: 5
gttatgtgct gatgggcttt atttgatcta cagaagatgc tctggtgaca ccctcagtgt      60
gtgttggtaa caccttcctg cctcgagata acttcgtata atgtatgcta tacgaagtta     120
tatgcatggc ctccgcgccg ggttttggcg cc                                    152

<210> SEQ ID NO 6
<211> LENGTH: 153
<212> TYPE: DNA
<213> ORGANISM: Unknown
<220> FEATURE:
<223> OTHER INFORMATION: Mammal

<400> SEQUENCE: 6
gtatgctata cgaagttatg ctagtaacta taacggtcct aaggtagcga gctagcccaa      60
ttgcgtactt tggatagtgt ctcttttaa cctaaatgac ctttattaac actgtcaggt      120
tcccttactc tcgagagtgt tcattgctgc act                                   153

<210> SEQ ID NO 7
<211> LENGTH: 24
<212> TYPE: DNA
<213> ORGANISM: Unknown
<220> FEATURE:
<223> OTHER INFORMATION: Mammal

<400> SEQUENCE: 7
ttgcattctt ttccaaataa gtgg                                             24

<210> SEQ ID NO 8
<211> LENGTH: 25
<212> TYPE: DNA
<213> ORGANISM: Unknown
<220> FEATURE:
<223> OTHER INFORMATION: Mammal

<400> SEQUENCE: 8
ttccaggatg aataggataa acagg                                            25

<210> SEQ ID NO 9
<211> LENGTH: 30
<212> TYPE: DNA
<213> ORGANISM: Unknown
<220> FEATURE:
<223> OTHER INFORMATION: Mammal

<400> SEQUENCE: 9
atccatcatc actccctgtg tttgtttccc                                       30

<210> SEQ ID NO 10
<211> LENGTH: 19
<212> TYPE: DNA
<213> ORGANISM: Unknown
<220> FEATURE:
<223> OTHER INFORMATION: Mammal

<400> SEQUENCE: 10
agctgactgc tgccgtcag                                                   19
```

```
<210> SEQ ID NO 11
<211> LENGTH: 31
<212> TYPE: DNA
<213> ORGANISM: Unknown
<220> FEATURE:
<223> OTHER INFORMATION: Mammal

<400> SEQUENCE: 11
tagactttgt agtgttagaa acatttggaa c                              31

<210> SEQ ID NO 12
<211> LENGTH: 33
<212> TYPE: DNA
<213> ORGANISM: Unknown
<220> FEATURE:
<223> OTHER INFORMATION: Mammal

<400> SEQUENCE: 12
atttttgtaa tgcaatcatg tcaactgcaa tgc                            33

<210> SEQ ID NO 13
<211> LENGTH: 22
<212> TYPE: DNA
<213> ORGANISM: Unknown
<220> FEATURE:
<223> OTHER INFORMATION: Mammal

<400> SEQUENCE: 13
ctcactctat cccatccaag gg                                        22

<210> SEQ ID NO 14
<211> LENGTH: 21
<212> TYPE: DNA
<213> ORGANISM: Unknown
<220> FEATURE:
<223> OTHER INFORMATION: Mammal

<400> SEQUENCE: 14
atgggcaggt agcatccaca g                                         21

<210> SEQ ID NO 15
<211> LENGTH: 29
<212> TYPE: DNA
<213> ORGANISM: Unknown
<220> FEATURE:
<223> OTHER INFORMATION: Mammal

<400> SEQUENCE: 15
tgaatcatcc ctttgtctag cagaaccgg                                 29
```

HUMANIZED IL-7 RODENTS

CROSS-REFERENCE TO RELATED APPLICATIONS

This application is a continuation of U.S. patent application Ser. No. 15/649,797, filed Jul. 14, 2017, which is a continuation of U.S. patent application Ser. No. 15/357,021, filed Nov. 21, 2016, now U.S. Pat. No. 9,737,059, which is a continuation of U.S. patent application Ser. No. 14/937,270, filed Nov. 10, 2015, which is a continuation of U.S. patent application Ser. No. 14/551,538, filed Nov. 24, 2014, now U.S. Pat. No. 9,232,776, which is a continuation of U.S. patent application Ser. No. 13/795,765, filed Mar. 12, 2013, now U.S. Pat. No. 8,962,913, which claims the benefit under 35 U.S.C. § 119(e) of U.S. Provisional Application No. 61/740,074, filed Dec. 20, 2012 and U.S. Provisional Application No. 61/660,976, filed Jun. 18, 2012, all of which are hereby incorporated by reference.

FIELD

Non-human animals (e.g., mammals, e.g., rodents such as mice, rats, and hamsters) that comprise a genetic modification comprising a replacement, at an endogenous locus, of a non-human IL-7 gene sequence with a human IL-7 gene sequence. Rodents and other non-human animals that express human IL-7 or humanized IL-7 from a locus under control of endogenous non-human regulatory sequences, or from an endogenous non-human IL-7 locus that comprises endogenous non-human regulatory sequences.

BACKGROUND

Transgenic mice that have randomly inserted transgenes that contain a human IL-7 sequence are known in the art. However, most if not all of these transgenic mice are not optimal in one aspect or another. For example, most mice transgenic for human IL-7 exhibit abnormal levels and/or ratios of certain cells, including T cells, that are likely due to a dysregulation of immune cell development, e.g., T cell development.

There remains a need in the art for non-human animals that comprise human IL-7-encoding sequences, wherein the human IL-7 encoding sequences are at an endogenous non-human IL-7 locus, and for non-human animals that express human IL-7 under the control of endogenous non-human regulatory elements. There is a need in the art for non-human animals that express human IL-7 in a manner that is as physiologically relevant in the non-human animal as possible. There is a need in the art for non-human animals that express a human IL-7, wherein the non-human animals lack a significant abnormality in peripheral cells, and/or in ratios of T cell subtypes.

SUMMARY

Genetically modified non-human animals, cells, tissues, and nucleic acids are provided that comprise a human IL-7 genomic sequence at an endogenous non-human IL-7 locus. The non-human animals express a humanized IL-7 protein from a modified locus regulated by one or more endogenous non-human regulatory sequences of the modified endogenous IL-7 locus. In various embodiments, the non-human animals are rodents, e.g., mice, rats, hamsters, etc. In a specific embodiment, the rodent is a mouse or a rat.

In various embodiments and aspects, the non-human animals comprise a modified IL-7 gene in the germline of the non-human animal at a modified endogenous IL-7 locus, wherein the modified endogenous IL-7 locus comprises a humanization of at least a portion of the endogenous IL-7 gene. In various embodiments, the mice are heterozygous or homozygous with respect to the modified IL-7 locus, In one embodiment, a non-human animal is provided that comprises a lack of a first endogenous IL-7 allele and a humanization of a second endogenous IL-7 allele, In various embodiments and aspects, the humanization is of one or more exons and/or introns. In various embodiments and aspects, non-human animals having a modified IL-7 locus are provided wherein one or both of an endogenous non-human 5'-untranslated region and an endogenous non-human 3'-untranslated region are retained in the modified animal, In one aspect, a genetically modified rodent is provided that comprises a replacement at an endogenous rodent IL-7 locus of an endogenous rodent IL-7 genomic sequence with a human IL-7 genomic sequence.

In one embodiment, the genetically modified rodent comprises a first rodent regulatory sequence upstream (with respect to the direction of transcription of the IL-7 gene) of the human IL-7 genomic sequence and a second rodent regulatory sequence downstream of the human IL-7 genomic sequence. In one embodiment, the first rodent regulatory sequence comprises a rodent promoter and/or enhancer, and the second rodent regulatory sequence comprises a 3'-UTR.

In one embodiment, the rodent is a mouse and comprises an endogenous mouse IL-7 gene locus having a mouse exon 1 and human exons 2, 3, 4, 5, and 6. In one embodiment, the endogenous mouse IL-7 gene locus comprises, from upstream to downstream with respect to the direction of transcription, mouse exon 1, at least a portion of a first mouse intron, and a contiguous human genomic fragment comprising human exon 2 through human exon 6. In one embodiment, the mouse further comprises a contiguous sequence of endogenous mouse DNA comprising an complete endogenous mouse IL-7 upstream (with respect to the direction of transcription of the IL-7 gene) promoter and regulatory region, wherein the contiguous mouse DNA is upstream of the human genomic fragment; and further comprises a contiguous sequence of endogenous mouse DNA 3'-UTR downstream of the human genomic fragment.

In one embodiment, the mouse comprises a mouse sequence that is at least 90%, at least 95%, at least 96%, at least 97%, at least 98%, or at least 99% identical with a sequence selected from SEQ ID NO:1, SEQ ID NO:2, and a combination thereof. In a specific embodiment, the mouse comprises a mouse sequence selected from SEQ ID NO:1 and SEQ ID NO:2.

In one aspect, a genetically modified mouse is provided that comprises a replacement at an endogenous mouse IL-7 locus of an endogenous mouse IL-7 genomic sequence with a human IL-7 genomic sequence to form a modified locus, wherein the human IL-7 genomic sequence comprises at least one human exon, and the modified locus comprises a mouse sequence selected from a sequence of SEQ ID NO:1, SEQ ID NO:2, and a combination thereof.

In one embodiment, the replacement comprises a human genomic fragment comprising exons 2 through 6, and the human genomic fragment is linked to mouse exon 1 to form a modified endogenous mouse IL-7 locus, wherein the modified mouse IL-7 locus comprises a mouse sequence selected from SEQ ID NO:1, SEQ ID NO:2, and a combination thereof.

In one aspect, a genetically modified rodent is provided that comprises an IL-7 gene that comprises a rodent exon 1 and at least a portion of a rodent intron 1, and a human IL-7 gene sequence of human IL-7 exons 2, 3, 4, 5, and 6, wherein the rodent comprises a sequence selected from a rodent upstream IL-7 regulatory sequence, a rodent IL-7 3'-UTR, and a combination thereof.

In one aspect, a genetically modified mouse is provided that comprises a sequence selected from SEQ ID NO:1, SEQ ID NO:2, and a combination thereof; wherein the mouse lacks an endogenous sequence encoding exons 2 through 5 of a mouse IL-7 protein, and the mouse comprises a nucleic acid sequence at an endogenous mouse IL-7 locus wherein the nucleic acid sequence encodes human IL-7 exons 2, 3, 4, 5, and 6.

In one aspect, a genetically modified rodent is provided that expresses a human or humanized IL-7 protein from an endogenous rodent IL-7 locus that is modified to express at least one human IL-7 exon. In one embodiment, the rodent IL-7 locus is modified to express a human or humanized iL7 protein encoded by a sequence comprising at least two human IL-7 exons. In one embodiment, the rodent IL-7 locus is modified to express a human or humanized IL-7 protein encoded by a sequence comprising at least three human IL-7 exons, In on embodiment, the rodent IL-7 locus is modified to express a human or humanized IL-7 protein encoded by a sequence comprising at least human IL-7 exons 2, 3, 4, 5, and 6 (i.e., 2 through 6), In one embodiment, the rodent IL-7 locus is modified to express a human IL-7 protein.

In one aspect, a genetically modified rodent is provided that expresses a human or humanized IL-7 protein from an endogenous mouse IL-7 locus that is modified to comprise at least human IL-7 exons 2 through 6 in place of mouse IL-7 exons 2 through 5.

In one aspect, a genetically modified rodent is provided that expresses a human or humanized IL-7 protein from a humanized endogenous rodent IL-7 locus comprising a humanized endogenous rodent :IL-7 coding region, wherein the humanized endogenous rodent IL-7 locus comprises all endogenous rodent regulatory elements that are present in a wild-type rodent upstream of a wild-type rodent IL-7 coding region and that are downstream of the wild-type rodent IL-7 coding region, In one aspect, a genetically modified rodent is provided that expresses a human or humanized IL-7 protein from a humanized rodent IL-7 locus that comprises rodent regulatory regions upstream and downstream of a nucleic acid sequence encoding the human or humanized IL-7 protein, wherein the human or humanized IL-7 protein is expressed in an expression pattern that is about the same as the expression pattern of a rodent IL-7 protein in a wild-type rodent. In one embodiment, the level of serum expression of the human or humanized IL-7 is about the same as the level of serum expression of a rodent IL-7 protein in a wild-type rodent.

in one aspect, a genetically modified rodent is provided that expresses a humanized IL-7 protein, wherein the lymphocyte population of the rodent is characterized by its B cell population that is about the same in number as a population of B cells in an age-matched wild-type mouse. In one embodiment, the modified rodent is characterized by a population of mature B cells that is about the same in number as a population of mature B cells in an age-matched wild-type mouse. In one embodiment, the humanized IL-7 protein is identical to a human IL-7 protein. In one embodiment, the humanized IL-7 protein comprises human sequence encoded by at least exons 2 through 6 of a human IL-7 gene.

In one aspect, a genetically modified rodent is provided that expresses a humanized IL-7 protein, wherein the lymphocyte population of the rodent is characterized by a population of T cells that is about the same in number as a population of T cells in an age-matched wild-type mouse. In one embodiment, the modified rodent exhibits a population of mature T cells that is about the same in number as a population of mature T cells in an age-matched wild-type mouse. In one embodiment, the modified rodent exhibits a population of peripheral T cells that is about the same in number as the population of peripheral T cells in an age-matched wild-type mouse. In one embodiment, the humanized IL-7 protein is identical to a human IL-7 protein. In one embodiment, the humanized IL-7 protein comprises human sequence encoded by at least exons 2 through 6 of a human IL-7 gene.

In one aspect, a genetically modified rodent is provided that expresses a humanized IL-7 protein, wherein the lymphocyte population of the rodent is characterized by a T cell population that exhibits a CD4:CD8 ratio that is about the same as the CD4:CD8 ratio in the T cell population of an age-matched wild-type mouse. In one embodiment, the humanized IL-7 protein is identical to a human IL-7 protein. In one embodiment, the humanized IL-7 protein comprises human sequence encoded by at least exons 2 through 6 of a human IL-7 gene.

In one aspect, a genetically modified rodent is provided that expresses a humanized IL-7 protein, wherein the rodent comprises a characteristic selected from a lack of a propensity to develop a chronic colitis; lack of over-expression of IL-7 in colonic mucosal lymphocytes; normal, or wild-type, expression of IL-7 in colonic mucosal lymphocytes; lacks a severe dermatitis; lacks a dermatitis characterized by a massive dermal infiltration of mononuclear cells; exhibits a CD4:CD8 ratio in its I cell population that is about the same as the CD4:CD8 ratio of an age-matched wild-type mouse; exhibits an expression pattern of human IL-7 that is about the same as an expression pattern of mouse IL-7 in a wild-type mouse; and a combination thereof.

In one aspect, a genetically modified rodent is provided that expresses a humanized IL-7 protein, wherein the rodent lacks a propensity to develop a chronic colitis.

In one aspect, a genetically modified rodent is provided that expresses a humanized IL-7 protein, wherein the rodent does not exhibit over-expression of IL-7 in colonic mucosal lymphocytes.

In one aspect, a genetically modified rodent is provided that expresses a humanize IL-7 protein, wherein the rodent does not exhibit a dermatitis characterized by a massive dermal infiltration of mononuclear cells.

In one aspect, a genetically modified rodent is provided that expresses a humanized IL-7 protein, wherein the rodent does not exhibit a lymphoproliferation into dermis.

In one aspect, a genetically modified rodent is provided that expresses a humanized IL-7 protein, wherein the rodent does not exhibit B and/or T cell lymphomas at a higher frequency than an age-matched wild-type mouse.

In one aspect, a genetically modified mouse is provided that expresses a humanized IL-7 protein, or a human IL-7 protein, wherein the mouse is no more prone than a wild-type mouse to developing a pathology selected from colitis, chronic colitis, severe dermatitis, pathological and/or massive infiltration of the dermis by mononuclear cells, lympoproliferation of the dermis, B cell lymphomas, T cell lymphomas, reduction in the number of mature B and/or T cells, reduction in the number of peripheral B and/or T cells, abnormal numbers of CD4+ T cells, abnormal numbers of CD8+ T cells, and a combination thereof In one aspect, a genetically modified non-human animal is provided, comprising in its germline a replacement of at least one non-human IL-7 exon with at least one human IL-7 exon to form a human or humanized IL-7-encoding gene, wherein the replacement is at an endogenous non-human IL-7 locus, wherein the human or humanized IL-7-encoding gene is under control of endogenous non-human regulatory elements, In one embodiment, the genetically modified non-human animal is a rodent. In one embodiment, the rodent is selected from a rat and a mouse.

In on embodiment, the human or humanized IL-7-encoding gene comprises human exons selected from the group consisting of human exon 1, human exon 2, human exon 3, human exon 4, human exon 5, human exon 6, and a combination thereof. In one embodiment, the human or humanized IL-7-enconding gene comprises no more than five human exons.

In one embodiment, the genetically modified non-human animal is a rodent that is a mouse and the modified locus comprises a replacement of mouse exons 2, 3, 4, and 5 with a human genomic segment comprising human IL-7 exons 2, 3, 4, 5, and 6.

In one embodiment, the human or humanized IL-7-encoding gene comprises a cDNA encoding a human or humanized IL-7 protein.

In one aspect, a genetically modified non-human animal is provided, comprising in its germline a transgene comprising a nucleic acid sequence encoding a human or humanized IL-7 gene, wherein the human or humanized IL-7 gene is flanked upstream and downstream with endogenous non-human regulatory sequences.

in one embodiment, the genetically modified non-human animal is a rodent. In one embodiment, the rodent is selected from the group consisting of a mouse, a rat, and a hamster.

In one embodiment, the genetically modified non-human animal comprises a human exon selected from the group consisting of human exon 1, human exon 2, human exon 3, human exon 4, human exon 5, human exon 6, and a combination thereof. In one embodiment, the human or humanized IL-7 gene comprises at least five human exons.

In one aspect, a method is provided for making a non-human animal with a human or humanized IL-7-encoding gene, comprising modifying the germline of the non-human animal to comprise a human or humanized IL-7-encoding gene flanked upstream and downstream with endogenous non-human IL-7 regulatory sequences.

In one embodiment of the method, the modification is at an endogenous non-human IL-7 locus.

In one embodiment of the method, the non-human animal is a rodent. In one embodiment, the rodent is selected from the group consisting of a mouse, a rat, and a hamster.

In one aspect, a genetically modified non-human animal is provided that is genetically modified to express human IL-7 in an expression pattern that is the same expression pattern as observed for a wild-type non-human animal of the same genus and species. In one embodiment, the non-human animal is a rodent. In a specific embodiment, the rodent is selected from a mouse and a rat.

In one embodiment, the level of human IL-7 expressed in the non-human animal is about the same as the level of non-human IL-7 in a corresponding wild-type mouse. In one embodiment, the non-human animal is a rodent. In a specific embodiment, the rodent is selected from a mouse and a rat.

In one aspect, a DNA construct is provided, comprising from 5' to 3' with respect to direction of transcription, a nucleic acid sequence homologous to a mouse IL-7 5' noncoding sequence, a human genomic fragment encoding a human IL-7 protein but not comprising a human regulatory sequence upstream or downstream of sequence encoding the human IL-7 protein, and a nucleic acid sequence homologous to a mouse IL-7 3' noncoding sequence.

In one aspect, a DNA construct is provided, comprising from 5' to 3' with respect to direction of transcription, a nucleic acid sequence that comprises a region of homology to a mouse IL-7 exon 1 sequence, a human genomic fragment encoding a human IL-7 protein but not comprising a human regulatory sequence upstream or downstream of sequence encoding the human IL-7 protein, and a nucleic acid sequence homologous to a mouse IL-7 3' noncoding sequence.

In one aspect, a genetically modified rodent cell is provided, wherein the rodent cell comprises a replacement at an endogenous rodent IL-7 locus of a gene sequence encoding a rodent IL-7 with a human genomic sequence encoding a human IL-7.

In one embodiment, the human genomic sequence comprises a contiguous human nucleic acid sequence spanning human IL-7 exons 2 through human IL-7 exon 6.

In one embodiment, the genetically modified rodent comprises a mouse IL-7 promoter at the endogenous rodent IL-7 locus, In one embodiment, the cell is selected from a pluripotent cell, an induced pluripotent cell, a totipotent cell, an ES cell, and an ovum.

In one embodiment, the cell secretes human IL-7. In one embodiment, the cell that secretes human IL-7 is selected from an epithelial cell (e.g., an intestinal epithelial cell), a hepatocyte, a keratinocyte, a dendritic cell, and a follicular dendritic cell. In one embodiment, the rodent cell is a bone marrow dendritic cell. In one embodiment, the cell that secretes human IL-7 is a thymic stromal cell; in a specific embodiment, the thymic stromal cell is a cortical epithelial cell.

In one aspect, a rodent embryo is provided, wherein the embryo comprises at least one rodent donor cell (e.g., an ES cell, a pluripotent cell, a totipotent cell, etc.) comprising a replacement of an endogenous rodent IL-7-encoding nucleic acid sequence with a nucleic acid sequence encoding a human IL-7 at the endogenous rodent IL-7 locus. In one embodiment, the donor cell is a mouse ES cell and the embryo is a host mouse embryo that is a pre-morula, a morula, or a blastocyst.

In one aspect, a rodent tissue that comprises a humanized. IL-7 gene at an endogenous rodent IL-7 locus is provided, wherein the rodent tissue is selected from thymic, splenic, epidermal, and intestinal.

In one aspect, a genetically modified mouse is provided that comprises a DNA sequence that encodes a human IL-7, wherein the mouse does not express a mouse IL-7, and wherein the mouse exhibits a T cell population that is about the same size as the T cell population of a wild-type mouse.

In one embodiment, the mouse exhibits a peripheral T cell population that is about the same size as a peripheral T cell population of a wild-type mouse.

In one embodiment, the T cell population is a mouse T cell population.

In one embodiment, the mouse is not more prone than a wild-type mouse to develop a B cell tumor comprising a pro-B or a pre-B cell.

In one embodiment, the mouse is not more prone than a wild-type mouse to develop a lymphoid tumor.

In one embodiment, the mouse does not exhibit a lymphoproliferative disorder in the absence of a known lymphoproliferative causative agent.

In one embodiment, the mouse does not exhibit a pathologic infiltration of T cell in a skin layer. In one embodiment, the mouse does not exhibit a symptom of alopecia.

In one embodiment, the majority of T cells of the genetically modified mouse are about the same in size distribution as in an age-matched wild-type mouse. In a specific embodiment, the genetically modified mouse does not exhibit an enlargement of T cell In one aspect, a rodent is provided that expresses a humanized or human IL-7 protein from an endogenous modified rodent IL-7 locus, wherein the serum concentration of human IL-7 in the rodent is physiologically normal.

In one aspect, a humanized rodent is provided that expresses a humanized IL-7 gene in the serum of the rodent at a physiologically normal concentration.

In one embodiment, the rodent is selected from a mouse and a rat.

In one embodiment, the physiologically normal serum concentration of human IL-7 is less than 10 picograms/mL. In one embodiment, the physiologically normal serum concentration of human IL-7 is less than 5 picograms/mL. In one embodiment, the physiologically normal serum concentration of human IL-7 in the rodent is about 2 picograms/mL to about 4 picograms/mL. In one embodiment, the physiologically normal serum concentration of human IL-7 in the rodent serum is about 2.4 picograms/mL to about 3.2 picograms/mL.

In one aspect, a method for making a human IL-7 protein is provided, comprising inserting into the germline of the non-human animal a human or humanized IL-7 coding gene under control of endogenous non-human regulatory elements, allowing the non-human animal to make the human or humanized IL-7, and isolating from the non-human animal (e.g., a mammal, e.g., a rodent such as, e.g., a mouse or rat or hamster) human or humanized IL-7.

In one aspect, a method for making a human IL-7 protein is provided, comprising isolating from a non-human animal as described herein (e.g., a mammal, e.g., a rodent such as, e.g., a mouse or rat or hamster).

In one aspect, a method is provided for making a non-human animal that comprises a human or humanized IL-7 gene in its germline, comprising inserting into the germline of the non-human animal a human or humanized IL-7-encoding nucleic acid sequence or fragment thereof, wherein the human or humanized IL-7-coding nucleic acid sequence or fragment thereof is under regulatory control of endogenous non-human regulatory elements. In one embodiment, the human or humanized IL-7 gene is at an endogenous non-human IL-7 locus (i.e., inserted between upstream and downstream non-human regulatory elements at the endogenous non-human IL-7 locus, wherein the human or humanized IL-7-coding nucleic acid sequence replaces the wild-type existing non-hunman IL-7 coding sequence in whole or in part). In one embodiment, the non-human animal is a mammal, e.g., rodent. In one embodiment, the rodent is selected from a mouse, a rat, and a hamster.

In one aspect, a method is provided for isolating from a non-human animal a T cell that has been exposed to a human or humanized IL-7 protein, comprising a step of isolating a T cell from a non-human animal as described herein. In one embodiment, the non-human animal is a mouse or a rat. In one embodiment, the T cell is a non-human T cell, e.g., a rodent T cell, e.g., a T cell of a mouse or a rat. In one embodiment, the T cell is selected from a T cell in the thymus and a peripheral T cell.

In one aspect, a method for identifying an agent that is an antagonist of human IL-7 is provided, comprising a step of administering an agent to a genetically modified rodent as described herein, determining an effect of the agent on a human IL-7 mediated function in the rodent, and identifying the agent as an IL-7 antagonist if it antagonizes the function of human IL-7 in the genetically modified rodent.

In one embodiment, the agent comprises an immunoglobulin variable domain that binds IL-7. In one embodiment, the agent specifically binds human IL-7 but not rodent IL-7. In one embodiment, the agent is an antibody.

In one aspect, a method for determining whether an agent reduces IL-7-mediated peripheral T cell population is provided, comprising a step of administering to a genetically modified rodent as described herein an IL-7 antagonist for a period of time, measuring peripheral T cell population number of the rodent at one or more time periods following administration, and determining whether the IL-7 antagonist reduces the peripheral T cell population.

In one aspect, the genetically modified non-human animal is heterozygous for a human or humanized IL-7-encoding gene. In one embodiment, the non-human animal is unable to express an endogenous IL-7 protein. In a specific embodiment, the non-human animal comprises a knockout of both endogenous IL-7 alleles.

Each of the aspects and embodiments described above and below may be used together, unless otherwise stated and unless otherwise clear from the context.

BRIEF DESCRIPTION OF THE FIGURES

FIG. 2 depicts human IL-7 concentration in serum of wild-type mice that has a genetic background of 75% C57B6 and 25% 129/svJ (75/25 WT) and mice heterozygous for a humanized endogenous IL-7 locus as described herein (5148 Het).

DETAILED DESCRIPTION

Figure 1:
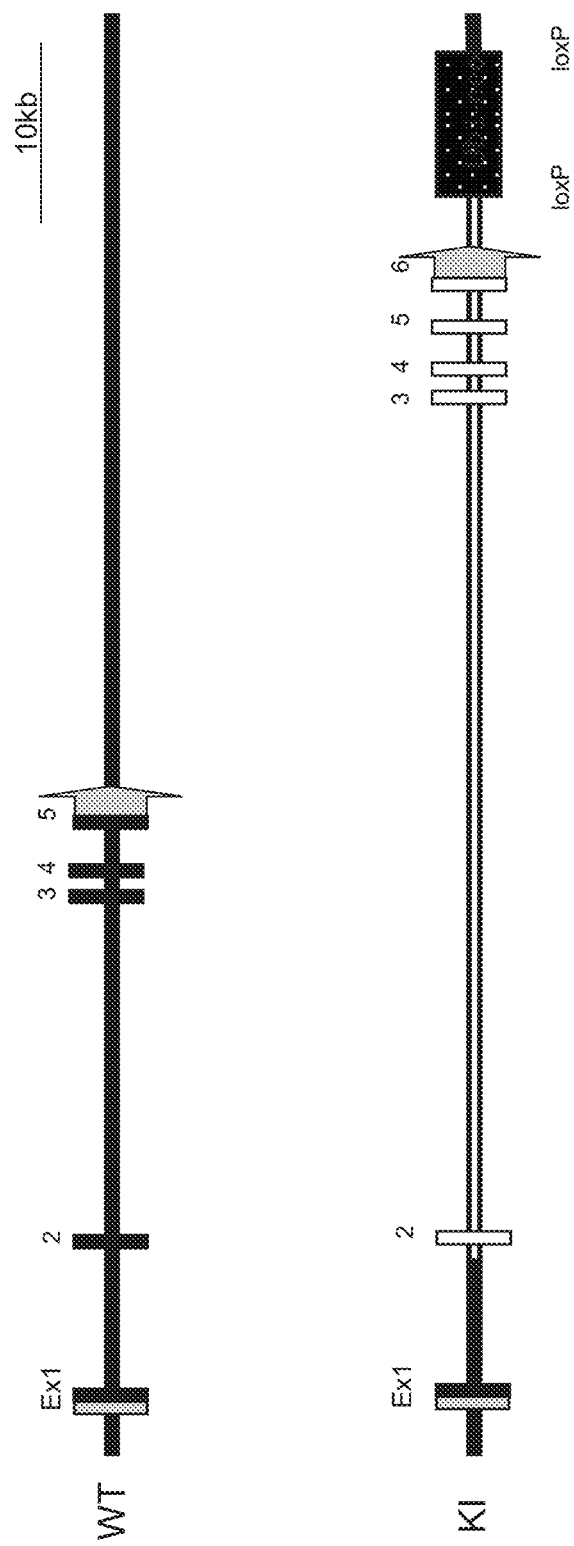
FIG. 1 depicts (not to scale) a schematic of a wild-type mouse IL7 gene locus (top) and a humanized endogenous mouse IL-7 locus (bottom) Open symbols indicate human sequence; closed symbols indicate mouse sequence; shaded items indicate untranslated regions; stippled region indicates other sequence.

In various embodiments, non-human animals are described that comprise the genetic modification(s) described herein. The genetically modified non-human animal may be selected from a group consisting of a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

In one aspect, the non-human animal is a mammal. In one aspect, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae e.g., mole rates, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse.

In various embodiments, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In another embodiment, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In one embodiment, the mouse is a mix of a BALB strain and another aforementioned strain.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more strains selected from the group consisting of Wistar, LEA, Sprague Dawley, Fischer, F344, F6, and Dark Agouti.

Genetically modified non-human animals that comprise a replacement of a non-human IL-7 gene sequence with a human IL-7 gene sequence are provided. Rodents that comprise a humanization of an IL-7 gene, at an endogenous rodent IL-7 locus, are provided. Methods for making rodents, e.g., mice, that comprise a replacement of an endogenous IL-7 gene or fragment thereof (e.g., a fragment comprising one or more exons) with a humanized IL-7 gene, or fragment thereof (e.g., a fragment comprising one or more exons), at the endogenous IL-7 locus. Cells, tissues, and mice are provided that comprise the humanized gene are provided, as well as cells, tissues, and mice that express human IL-7 from an endogenous non-human IL-7 locus.

IL-7 is a cytokine that is essential for development of immature B and T cells and, to some degree, mature T cells; IL-7 knockout mice display a severe depletion of mature B and T cells (von Freeden-Jeffry U. et al. (1995) Lymphopenia in interleukin (IL)-7 gene-deleted mice identifies IL-7 as a nonredundant cytokine, J. Exp. Med. 181:1519-1526). The depletion is apparently due to a block between pro-13 and pre-B cells, and a block in T cell proliferation (rather than a block in T cell differentiation; ratios of T cell types in IL-7 KO mice are about normal) that results in a depressed population of T cells and mature B cells (Id.). IL-7 is produced by epithelial cells in the thymus and intestine, in keratinocytes, liver, and dendritic cells—but not by normal lymphocytes (reviewed, e.g., in Fry T. J. and Mackall, C. L. (2002) Interleukin-7: from bench to clinic, Blood 99(10): 3892-3904).

Simply put, IL-7 increases T cell number and enhances T cell function (see, e.g., Morrissey, J. J. (1991) Administration of IL-7 to normal mice stimulates B-lymphopoiesis and peripheral lymphadenopathy, J. lmmunol. 147:561-568; Faltynek, C. R. et al. (1992) Administration of human recombinant IL-7 to normal and irradiated mice increases the numbers of lymphocytes and some immature cells of the myeloid lineage, J. Immunol. 149:1276-1282; Risdon, G. J. et al. (1994) Proliferative and cytotoxic responses of human cord blood T lymphocytes following allegenic stimulation, Cell. Immunol. 154:14-24). Functional enhancement of T cells can be achieved by a short duration of IL-7 exposure, whereas increases in T cell number reflect a proliferative effect that is achieved with a longer duration exposure (Geiselhart, L. A. et al. (2001) IL-7 Administration Alters the CD4:CD8 Ratio Increases T Cell Numbers, and Increases T Cell Function in the Absence of Activation, J. Immunol. 166:3019-3027; see also, Tan J. T. et al. (2001) IL-7 is critical for homeostatic proliferation and survival of naive T cells, Proc. Natl. Acad. Sci. USA 98(15):8732-8737).

IL-7 is necessary for both early and late stage T cell regulation. IL-7 is not expressed by T cells, which must encounter IL-7 that is released by non-thymic cells in the periphery and that is believed to be responsible for peripheral T cell proliferation and maintenance (reviewed, e.g., in Guimond, M (2005) Cytokine Signals in T-Cell Homeostasis, J. Immunother. 28(4):289-294). IL-7 starvation results in severely impaired T cell development and survival of naïve T cells. IL-7 also appears to be necessary for the survival of mature T cells; mature T cells acquired through adoptive transfer into IL-7-deficient mice enter apoptosis where the mice lack an IL-7 gene, but not in mice that express IL-7 that lack an IL-7R gene (Schluns, K. S. et al. (2000) Interleukin-7 mediates the homeostasis of naïve and memory CD8 T cells in vivo, Nat. Immunol. 1(5):426-432. Loss of IL-7 function results in a SCID-like phenotype in mice (Puel, A. and Leonard, W. J. (2000) Mutations in the gene for the IL-7 receptor result in T(−)B(+)NK(+) severe combined immunodeficiency disease, Curr. Opin. Immunol. 12:468-473), presumably due to T cell atrophy and death caused by diminished growth rate likely mediated by glycolytic insufficiency in the absence of IL-7 stimulus (Jacobs, S. R. et al. (2010) IL-7 Is Essential for Homeostatic Control of T Cell Metabolism In Vivo, J. Immunol. 184:3461-3469).

The human IL-7 gene comprises 6 exons that extend over 33 kb and is located on chromosome 8 at 8q12-13. Mouse IL-7 comprises 5 exons (there is no counterpart in mouse to human exon 5) and is about 80% homologous to the human gene; analysis of non-coding sequences of the human and the mouse genes revealed a paucity of recognizable regulatory motifs responsible for transcription and regulation of gene expression (Lupton, S. D. et al. (1990) Characterization of the Human and Murine IL-7 Genes, J. Immunol. 144(9): 3592-3601), suggesting that regulation of IL-7 expression may be complex. However, mouse BAC fragments comprising a reporter gene at the hIL-7 locus have been expressed in mice to successfully ascertain expression patterns of IL-7 in mice (see, e.g., Avles, N. L. et al. (2009) Characterization of the thymic IL-7 niche in vivo, Proc. Natl. Acad. Sci. USA 106(5):1512-1517; Mazzucchelli, R. I. (2009) Visualization and Identification of IL-7 Producing Cells in Reporter Mice, PLoS ONE 4(11):e7637; Repas, J. F. et al. (2009) IL7-hCD25 and IL7-Cre BAC transgenic mouse lines: new tools for analysis of IL-7 expressing cells, Genesis 47:281-287). In at least one case, a BAC-based replacement of an IL-7 exon with a reporter required the entire 43 kb IL-7 locus as well as 96 kb of 5' flanking sequence and 17 kb of 3' flanking sequence in the hope of faithfully recapitulating IL-7 expression of wild-type mice (Repass, J. F. et al. (2009)). In any case, data from the different studies on reporter expression driven by putative IL-7 regulatory elements vary somewhat from one another and from earlier observations, supporting an inference that IL-7 regulation might not have been faithfully recapitulated in these reporter mice (IL-7 reporter transgenic mice are reviewed in Kim, G. Y. et al. (2011) Seeing Is Believing: Illuminating the Source of In Vivo Interleukin-7, Immune Network 11(1):1-10). Human IL-7 is functional on mouse cells, but mouse IL-7 is not functional on human cells.

Transgenic mice that express abnormally or poorly regulated human IL-7 exhibit a panoply of pathologies or syndromes. Mice transgenic fur a murine IL-7 cDNA under control of mouse Ig heavy chain enhancer, κ light chain enhancer, and light chain promoter) to target expression in the lymphoid compartment) exhibit significantly enhanced numbers of B cell precursors and an overall expansion of all subsets of thymocytes in the thymus and peripheral T cells (Samaridis, J. et al. (1991) Development of lymphocytes in interleukin 7-transgenic mice, Eur. J. Immunol. 21:453-460).

Transgenic mice that express IL-7 from a mouse cDNA under control of an SRα promoter develop a panoply of pathologies, including a chronic colitis that histopathologically mimics chronic colitis in humans, and is characterized by at least a transient over-expression of IL-7 in colonic mucosal lymphocytes (but not colonic epithelial cells) and its apparent accumulation in mucus of goblet cells of the colonic mucosa (Watanabe, M. et al. (1998) Interleukin 7 Transgenic Mice Develop Chronic Colitis with Decreased Interleukin 7 Protein Accumulation in the Colonic Mucosa, J. Exp Med. 187(3):389-402; Takebe, Y. et al. (1988) sR alpha promoter: an efficient and versatile mammalian cDNA expression system composed of the simian virus 40 early promoter and the R-U5 segment of human T-cell leukemia virus type 1 long terminal repeat, Mol. Cell Biot. 8(1):466-472). Constitutive expression of mouse IL-7 driven by the same promoter in transgenic mice also develop a severe dermatitis characterized by gross deformities and a massive dermal infiltration of mononuclear cells that are mostly TCRγə cells (Uehira, M. et al. The development of dermatitis infiltrated by γə T cells in IL-7 transgenic mice, Intl. Immunol. 5(12):1619-1627). Transgenic mice expressing a murine IL-7 cDNA driven by a murine heavy chain promoter and enhancer also exhibited dermatitis and lymphoproliferation into the dermis, but reportedly of TCRαβ cells and cells that express Thy-1, CD3, and CD5 but lack CD4 and CD8 (CD4+/CD8+thymocytes are virtually absent from these transgenic mice); these mice also developed B and T cell lymphomas, presumably associated with a prolonged lymphoproliferation observed in these mice (see, Rich, B. E. et al. (1993) Cutaneous lymphoproliferation and lymphomas in interleukin 7 transgenic mice, J. Exp. Med. 177:305-316).

Dysregulation of the IL-7 gene is associated with a variety of pathological states. Mice expressing transgenic mouse IL-7 under control of the MHC class II Eα promoter are highly prone to lymphoid tumors (see, e.g., Fisher, A. G. et at (1995) Lymphoproliferative disorders in IL-7 transgenic mice: expansion of immature B cells which retain macrophage potential, hit. Immunol. 7(3):414-423; see, also, Ceredig, R. et al. (1999) Effect of deregulated IL-7 transgene expression on B lymphocyte development in mice expressing mutated pre-B cell receptors, Eur. J. Immunol. 29(9): 2797-2807). T cell sizes are also larger in the transgenic mice, and a polyclonal T cell expansion is observed (predominantly CD8+, indicating a perturbed regulation in these mice) (Mertsching, E. et al, IL-7 transgenic mice: analysis of the role of IL-7 in the differentiation of thymocytes in vivo and in vitro, Intl. Immunol. 7(3):401-414). Other transgenic mice that over-express mIL-7 (by about 25-50-fold) through the MHC class II Eα promoter appear grossly healthy (but for a low incidence of B cell tumors) and exhibit a 10-20-fold increase in T cell number over wild-type mice, characterized by large numbers of CD8+cells that are also $CD44^{hi}$ and $CD122^{hi}$ (Kieper W. C. et al. (2002) Overexpression of Interleukin (IL)-7 Leads to IL-15-independent Generation of Memory Phenotype CD8+ T Cells, J. Exp. Med. 195(12):1533-1539).

Mice that constitutively express mouse IL-7 from a cDNA under control of the MHC class II Ea promoter selectively expand IL-7-responsive early B cells, and are a good source of tumors comprising pro-B and pre-B cells. Mice that express IL-7 driven by a human K14 promoter develop a lymphoproliferative response that results in T cell infiltrates of skin that resemble alopecia.

Mice transgenic for IL-7R display large reductions in double negative (CD4-CD8-) precursor cells in thymus, presumably due to depletion of IL-7 by the large number of double positive thymocytes in the transgenic mice, suggesting that IL-7 levels must be exquisitely controlled to promote normal thymocyte development (see, e.g., Malek, T. R. (2004) If -7: a limited resource during thymopoiesis, Blood, 104(13):2842).

As early as the cloning of human IL-7, it has been known that human IL-7 can induce proliferation of murine pre-B cells (Goodwin, R. G. et al. (1989) Human interleukin 7: Molecular cloning and growth factor activity on human and murine B-lineage lines, Proc. Natl. Acad. Sci. USA 86:302-306). Although expressed in certain chronic lymphocytic leukemia cells, expression of mouse IL-7 in tumor cells implanted in mice induce inflammation and reduced tumorigenicity, yet paradoxically mice transgenic for IL-7 are prone to lymphomas (reviewed in Foss, H.-D, et al. (1995) Frequent Expression of IL-7 Gene Transcripts in Tumor Cells of Classical Hodgkin's Disease, Am. J. Pathol. 146 (1):33-39). Thus, it is desirable to obtain mice that express human IL-7 (but not mouse IL-7) from endogenous mouse IL-7 loci in a physiologically relevant fashion, in particular but not limited to mice that comprise human or mouse tumors, e.g., lymphocytic tumors.

Mice that express human IL-7 in a physiologically relevant manner are also useful for evaluating anti-tumor properties of putative therapeutics (including human IL-7 and analogs thereof) in xenograft models of human solid tumors in mice. For example, SCID mice implanted with HT29 human colon adenocarcinoma and tested under a variety of conditions (e.g., ablation of native T cells and addition of human T cells; addition of recombinant human IL-7, etc.) (see, Murphy, W. J. et al. (1993) Antitumor Effects of Interleukin-7 and Adoptive Immunotherapy on Human Colon Carcinoma Xenografts, J. Clin. Invest, 92:1918-1924). That study found that human IL-7 when administered with human T cells resulted in a significantly prolonged survival than in the absence of human IL-7 (Id.).

Thus, mice that express human in particular mice that are capable of supporting a xenograft (e.g., a human tumor), such as, e.g., immunodeficient mice, have a specific and a well-established utility. IL-7 signaling has been shown to be necessary for development and survival of human T-cell acute lymphoblastic leukemias (T-ALL) in vitro and in vivo. (Touw, I. et al, (1990) Interleukin-7 is a growth factor of precursor B and T acute lymphoblastic leukemia. Blood 75, 2097-2101) T-ALL is an aggressive hematological cancer with poor prognosis; the understanding of mechanisms driving proliferation and survival of T-ALL cells remains relatively poor due to lack of xenograft models that can support the growth of patient derived tumors in vivo. Thus, an immunodeficient animal expressing human IL-7 can serve as an invaluable in vivo system for testing pharmaceutical compositions against such T-cell related malignancies, e.g., testing the efficacy of a pharmaceutical composition to target IL-7-mediated signaling in a mouse that expresses human IL-7 and has an implanted T-cell derived tumor, wherein the tumor requires IL-7 signaling for development and survival.

EXAMPLES

Example 1

Humanizing the Mouse IL-7 Locus

Mouse ES cells were modified to replace mouse IL-7 gene sequences with human IL-7 gene sequences at the endogenous mouse IL-7 locus, under control of mouse IL-7 regulatory elements, using VELOCIGENE® genetic engineering technology, to produce a humanized locus as shown in FIG. 1.

Targeting Construct. Bacterial homologous recombination (BHR) is performed to construct a large targeting vector (LTVEC) containing the human IL-7 gene for targeting to the mouse IL-7 locus using standard MR techniques (see, e.g., Valenzuela et al. (2003) High-throughput engineering of the mouse genome coupled with high-resolution expression analysis, Nature Biotech. 21(6):652-659). Linear fragments are generated by ligating PCR-generated homology boxes to cloned cassettes followed by gel isolation of ligation products and electroporation into BHR-competent bacteria harboring the target bacterial artificial chromosome (BAC). Mouse BAC bMQ-271g18 is used as the source of mouse sequence; human BAC RP11-625K1 is used as the source of human sequence. Following a selection step, correctly recombined clones are identified by PCR across novel junctions, and by restriction analysis. A large targeting vector (LTVEC) containing the homology arms and human IL-7 gene sequences was made. Mouse ES cells were electroporated with the LTVEC constructs, grown on selection medium, and used as donor ES cells to make humanized IL-7 mice.

The mouse IL-7 gene (mouse GeneID: 96561; RefSeq transcript: NM_008371.4) is modified by deleting exons 2 through 5 (deletion coordinates NCBIM37:ch3:7604650-7573021; minus strand) and replacing them with human IL-7 (EntrezGeneID:6023, RefSeq transcript NM_000880.3) exons 2 through 6 (replacement coordinates GRCh37Lch*:79711168-79644608; minus strand). The human genomic IL-7 sequence is provided in SEQ ID NO:3 (NC#166E2F2). The mouse genomic IL-7 locus is known and reported as a 41,351 nt sequence under accession number NC0000696 (hereby incorporated by reference); relevant 5' and 3' sequences of the mouse IL7 genomic locus are provided in SEQ ID NO:1 (5' flanking) and SEQ ID NO:2 (3' flanking).

The LTVEC comprising the humanized IL-7 gene had a 48 kb upstream mouse targeting arm flanked upstream with a NotI site, and a 77 kb downstream mouse targeting arm flanked downstream with a NotI site. The LTVEC was linearized with NotI for electroporation.

Following construction of the LTVEC, nucleotide sequence of the LTVEC was obtained across the mouse/ human 5' junction, which included, from 5' (mouse) to 3' (human), the following sequence with the mouse/human junction nucleotides in uppercase: 5' —tgcaagcacc aaaaaggtga ccacacttca cattggcgat cgcGGgtttc tatctgagga tgt-gaattta tttacaga—3' (SED ID NO:4).

Nucleotide sequence of the LTVEC across the junction of the human insertion and the 5' end of the cassette (see FIG. 1) was determined and included the following sequence having, from 5' to 3', human sequence/restriction site/loxp/ cassette sequence with the human sequence/restriction site junction nucleotides in uppercase: 5'—gttatgtgct gatgggcttt atttgatcta cagaagatgc tctggtgaca ccctcagtgt gtgttggtaa cacct-tcctg CCtcgagata acttcgtata atgtatgcta tacgaagtta tatgcatggc ctccgcgccg ggttaggcs cc—3' (SEQ ID NO:5).

Nucleotide sequence of the LTVEC across the junction of the end of the cassette and the beginning of mouse sequence was determined and included the following sequence having, from 5' to 3', cassette sequence/restriction site/mouse sequence with the junction nucleotides in uppercase:

5'—gtatgctata cgaagttatg ctagtaacta taacggtcct aagg-tagcga gctagCCcaa ttgcgtactt tggatagtgt ctcttttaa cctaaatgac ctttattaac actgtcaggt tcccttactc tcgagagtgt tcattgctgc act—3' (SEQ ID NO:6).

Following electroporation of the ES cell, a loss of native allele assay (see, e.g., Valenzuela et al. (2003)) is performed to detect loss of endogenous IL-7 sequence due to the targeting. Primer pairs, fragment sizes, and TAQMAN™ probes are as shown in Table 1. The C1 probe binds the mouse IL-7 genomic sequence (NC0000696) at nts 9,635-9,664; the C2 probe binds the mouse IL-7 genomic sequence (NC0000696) at nts 39,793-39,825. For a gain of allele assay, the C3 probe binds the human IL-7 genomic sequence (NC#166E2F2) at nts 29,214-29,242.

TABLE I

LTVEC Primers and Probes

| Primer | Position | Sequence (5' to 3') | SEQ ID | Size (bp) |
|---|---|---|---|---|
| Primer Pair C1 | Forward | ttgcattctt ttccaaataa gtgg | 7 | 81 |
| C1 | Reverse | ttccaggatg aataggataa acagg | 8 | |
| C1 TAQMAN™ probe | | atccatcatc actccctgtg tttgtttccc | 9 | |
| Primer Pair | Forward | agctgactgc tgccgtcag | 10 | 125 |

TABLE I-continued

LTVEC Primers and Probes

| Primer | Position | Sequence (5' to 3') | SEQ ID | Size (bp) |
|---|---|---|---|---|
| C2 | Reverse | tagactttgt agtgttagaa acatttggaa c | 11 | |
| C2 TAQMAN™ probe | | atttttgtaa tgcaatcatg tcaactgcaa tgc | 12 | |
| Primer Pair C3 | Forward | ctcactctat cccatccaag gg | 13 | 74 |
| C3 | Reverse | atgggcaggt agcatccaca g | 14 | |
| C3 TAQMAN™ probe | | tgaatcatcc ctttgtctag cagaaccgg | 15 | |

Example 2

Humanized IL-7 Mice

Generating humanized IL-7 mice. Donor mouse ES cells comprising a humanized IL-7 locus are introduced into early stage mouse embryos by the VELOCIMOUSE® method (Poueymirou et al. (2007) F0 generation mice fully derived from gene-targeted embryonic stem cells allowing immediate phenotypic analyses, Nat Biotechnol 25:91-99). Four F0 mice fully derived from donor ES cells were obtained that were heterozygous for humanization of the endogenous mouse IL-7 locus. F0 mice are bred to homozygosity with respect to the humanization. Homozygous mice are genotyped to confirm homozygosity. All mouse studies were overseen and approved by Regeneron's Institutional Animal Care and Use Committee (IACUC).

Example 3

Expression of Human IL-7 in a Mouse

Mice humanized for the IL-7 gene and their non-humanized littermate controls were bled and serum concentrations of human IL-7 were measured using QuantikineHS Human IL-7 Immunoassay kit from R&D Systems, Inc. Data was analyzed using Microsoft Excel and plotted using Prism statistical analysis software. Mice heterozygous for the humanized IL-7 locus (designated MAID 5148 het) expressed human IL-7 in serum at a physiologically relevant concentration. This is in contrast to transgenic human IL-7 mice bearing lentivirally transduced human IL-7 in double knockout mice, which mice exhibit unphysiologically and potentially seriously detrimental high levels of human IL-7 in serum (10 to 100 pg/mL) (O'Connell, R. M. et al. (2010) Lentiviral Vector Delivery of Human Interleukin-7 (hIL-7) to Human Immune System (HIS) Mice Expands T Lymphocyte Populations, PLoS ONE 5(8):e12009). In contrast, mice heterozygous for a humanized endogenous IL-7 locus exhibited about 2.4 to about 3.2 pg/mL in serum (FIG. 2), reflecting normal, or physiologically appropriate, levels of IL-7.

What is claimed is:

1. A genetically modified mouse whose genome comprises a replacement of a genomic fragment of a mouse IL-7 gene at an endogenous mouse IL-7 locus with a genomic fragment comprising exons 2, 3, 4, 5 and 6 of a human IL-7 gene to form a humanized IL-7 gene at the endogenous mouse IL-7 locus, wherein the human IL-7 gene comprises the nucleotide sequence of SEQ ID NO: 3;

the resulting modified mouse IL-7 locus lacks mouse IL-7 exons 2, 3, 4 and 5;

the humanized IL-7 gene is under control of endogenous mouse IL-7 5' regulatory elements; and the IL-7 protein encoded by the humanized IL-7 gene is expressed in the serum of the genetically modified mouse.

2. The genetically modified mouse of claim 1, wherein the humanized IL-7 gene comprises the nucleotide sequence of SEQ ID NO: 4 at the mouse-human junction.

3. The genetically modified mouse of claim 1, wherein the humanized IL-7 gene comprises mouse IL-7 exon 1 and human IL-7 exons 2, 3, 4, 5 and 6.

4. The genetically modified mouse of claim 1, wherein said mouse is heterozygous with respect to said replacement.

5. The genetically modified mouse of claim 1, wherein said mouse is homozygous with respect to said replacement.

6. The genetically modified mouse of claim 1, wherein the mouse does not express an endogenous mouse IL-7.

* * * * *